US012702717B2

(12) United States Patent
Enomoto et al.

(10) Patent No.: US 12,702,717 B2
(45) Date of Patent: Aug. 11, 2026

(54) ANTI-MEFLIN ANTIBODY FOR USE IN TREATMENT OF CANCER IN SUBJECT HAVING CANCER, AND PHARMACEUTICAL COMPOSITION COMPRISING THE ANTIBODY

(71) Applicants: National University Corporation Tokai National Higher Education and Research System, Nagoya (JP); Sowakai Medical Foundation, Kurashiki (JP)

(72) Inventors: Atsushi Enomoto, Aichi (JP); Nobutoshi Esaki, Aichi (JP); Masahide Takahashi, Aichi (JP); Yuki Miyai, Aichi (JP); Ryota Ando, Aichi (JP); Yukihiro Shiraki, Aichi (JP); Yoshihiro Nishida, Aichi (JP); Makoto Matsuyama, Okayama (JP); Shino Manabe, Okayama (JP)

(73) Assignees: National University Corporation Tokai National Higher Education, Nagoya (JP); Sowakai Medical Foundation, Kurashiki (JP)

( * ) Notice: Subject to any disclaimer, the term of this patent is extended or adjusted under 35 U.S.C. 154(b) by 1044 days.

(21) Appl. No.: 17/759,952

(22) PCT Filed: Feb. 3, 2021

(86) PCT No.: PCT/JP2021/003851

§ 371 (c)(1),
(2) Date: Aug. 2, 2022

(87) PCT Pub. No.: WO2021/157601

PCT Pub. Date: Aug. 12, 2021

(65) Prior Publication Data

US 2023/0084099 A1 Mar. 16, 2023

(30) Foreign Application Priority Data

Feb. 3, 2020 (JP) ................................ 2020-016535

(51) Int. Cl.
*A61K 47/68* (2017.01)
*A61P 1/04* (2006.01)
(Continued)

(52) U.S. Cl.
CPC .... *A61K 47/6889* (2017.08); *A61K 47/68031* (2023.08); *A61K 47/6851* (2017.08);
(Continued)

(58) Field of Classification Search
IPC .................................................. A61K 47/6889
See application file for complete search history.

(56) References Cited

U.S. PATENT DOCUMENTS

2017/0151343 A1 6/2017 Gish et al.
2017/0151344 A1 6/2017 Gish et al.
2021/0002714 A1 1/2021 Miyai et al.

FOREIGN PATENT DOCUMENTS

JP 2019-500327 A 1/2019
JP 2019-501124 A 1/2019
(Continued)

OTHER PUBLICATIONS

International Search Report issued Mar. 23, 2021 in PCT/JP2021/003851 filed Feb. 3, 2021, 3 pages.
(Continued)

*Primary Examiner* — Karl J Puttlitz
(74) *Attorney, Agent, or Firm* — Oblon, McClelland, Maier & Neustadt, L.L.P.

(57) ABSTRACT

An anti-MEFLIN antibody and a pharmaceutical composition comprising the antibody is described. The pharmaceutical composition may comprise an antibody-drug conjugate (Continued)

(ADC) of the anti-MEFLIN antibody and a cytotoxic agent, which may be connected to each other by a linker. The pharmaceutical composition may be used in the treatment of a cancer in a subject.

15 Claims, 24 Drawing Sheets

Specification includes a Sequence Listing.

(51) Int. Cl.
*A61P 35/00* (2006.01)
*C07K 16/28* (2006.01)

(52) U.S. Cl.
CPC ................ *A61P 1/04* (2018.01); *A61P 35/00* (2018.01); *C07K 16/28* (2013.01)

(56) References Cited

FOREIGN PATENT DOCUMENTS

| | | |
|---|---|---|
| WO | WO 2017/022472 A1 | 2/2017 |
| WO | WO 2019/159825 A1 | 8/2019 |

OTHER PUBLICATIONS

Yasuyuki Mizutani, et al., "Meflin-Positive Cancer-Associated Fibroblasts Inhibit Pancreatic Carcinogenesis," Cancer Research, vol. 79, No. 20, Oct. 15, 2019, 66 pages.
Atsushi Enomoto, "Identification of "cancer-restraining fibroblasts" present in cancer stroma and their true nature," Programs and Abstracts of the 27th Annual Meeting of the Japanese Breast Cancer Society, col. WS-1-01-4, 2019, 4 pages (with English language translation).
James W. Purcell, et al., "LRRC15 Is a Novel Mesenchymal Protein and Stromal Target for Antibody-Drug Conjugates," Cancer Research, vol. 78, No. 14, Jul. 15, 2018, 15 pages.
Christopher Szot, et al., "Tumor stroma-targeted antibody-drug conjugate triggers localized anticancer drug release," The Journal of Clinical Investigation, vol. 128, No. 7, Jul. 2018, 18 pages.
Akemi Nagasawa, et al., "Cloning of the cDNA for a New Member of the Immunoglobulin Superfamily (ISLR) Containing Leucine-Rich Repeat (LRR)," Genomics, vol. 44, 1997, pp. 273-279.
Keiko Maeda, et al., "Identification of Meflin as a Potential Marker for Mesenchymal Stromal Cells," Scientific Reports, vol. 6, No. 22288, 2016, 15 pages.
Mihaela Crisan, et al., "A Perivascular Origin for Mesenchymal Stem Cells in Multiple Human Organs," Cell Stem Cell, vol. 3, Sep. 11, 2008, pp. 301-313.
Hiroki Kobayashi, et al., "Cancer- associated fibroblasts in gastrointestinal cancer," Nature Reviews, Gastroenterology & Hepatology, vol. 16, May 2019, pp. 282-295.
Akitoshi Hara, et al., "Roles of the Mesenchymal Stromal/Stem Cell Marker Meflin in Cardiac Tissue Repair and the Development of Diastolic Dysfunction," Circulation Research, vol. 125, Aug. 2, 2019, pp. 414-430.
Nicholas Schaum, et al., "Single-cell transcriptomics of 20 mouse organs creates a *Tabula muris*," Nature, vol. 562, Oct. 18, 2018, 25 pages.
Kobayashi, H. et al., "The Balance of Stromal BMP Signaling Mediated by GREM1 and ISLR Drives Colorectal Carcinogenesis", Gastroenterology, vol. 160, 2021, 48 pages.
Liu, S. et al., "Targeting TGGFB signal transduction for cancer therapy" Nature, Signal Transduction and Targeted Therapy, vol. 6, No. 8, 2021, pp. 1-20.

Clone #21-3

Clone #25-1

Clone #8-2

Clone #3-2
Clone #11-8
Clone #12-2
Clone #13-2
Clone #16-5
Clone #19-7
Clone #22-3
Clone #23-1
Clone #32-1

Tissue image

Tissue image

Tissue image

Tissue image

Tissue image

Stomach cancer (MKN45)

PBS
21-3 ADC 5mg/kg
25-1 ADC 5mg/kg
Cisplatin 2mg/kg

Tumor size (mm3)

0
500
1000
1500
2000

0 2 4 6 8 10 12 14 16 18 20 22 24 26 28 30 32 34 36 38 40 42 44

The number of elapsed days (d)

Tissue image

Pancreas

Blue (DAPI): Nucleus
Green (Alexa488): MEFLIN
Red (Alexa594): Cathepsin K

Tumor tissue image of BxPC-3 xenograft model

Blue (DAPI): Nucleus
Green (Alexa488): MEFLIN
Red (Alexa594): Cathepsin K

Tissue image

Tissue image

Tissue image

Tissue image

Tissue image

Tissue image

Immunohistochemical staining (IHC)

*In situ* hybridization (ISH)

ANTI-MEFLIN ANTIBODY FOR USE IN TREATMENT OF CANCER IN SUBJECT HAVING CANCER, AND PHARMACEUTICAL COMPOSITION COMPRISING THE ANTIBODY

CROSS-REFERENCE TO RELATED APPLICATIONS

The present application is a 35 U.S.C. § 371 national stage application of International patent application PCT/JP2021/003851, filed Feb. 3, 2021, which is based on and claims the benefit of priority to Japanese Application No. 2020-016535, filed Feb. 3, 2020. The entire contents of these applications are incorporated herein by reference.

TECHNICAL FIELD

The present invention relates to an anti-MEFLIN antibody for use in the treatment of a cancer in a subject having the cancer, and a pharmaceutical composition comprising the antibody.

BACKGROUND ART

MEFLIN is a membrane protein that is encoded by ISLR (immunoglobulin superfamily containing leucine-rich repeat) gene obtained from a library of human genes predominantly expressed in the retina compared with the brain, and contains leucine-rich repeats (LRR) and an immunoglobulin (Ig)-like domain (Non Patent Literatures 1 and 2). This protein is also known as the name ISLR, as in the gene name (Non Patent Literature 1). MEFLIN is GPI (glycosylphosphatidylinositol)-anchored on cell membrane surface and has also been reported to be cleaved near the cell membrane and secreted to the outside of the cell (Non Patent Literature 2).

MEFLIN is a protein specifically expressed in mesenchymal stem cells (Non Patent Literature 2). While many molecules such as CD105, CD73, CD90, CD146, and CD271 are known as markers of mesenchymal stem cells, MEFLIN has been reported to be the most specific marker molecule for the mesenchymal stem cells among them (Non Patent Literature 2 and Patent Literature 1).

A small number of mesenchymal stem cells expressing MEFLIN reside perivascularly in all organs or reside in connective tissues and have the ability to differentiate into osteoblasts, chondroblasts, lipoblasts, skeletal muscle cells, myofibroblasts, and nerve cells (Non Patent Literature 2). There is also a report stating that mesenchymal stem cells are cells almost identical to pericytes (vascular pericytes) or perivascular fibroblasts (Non Patent Literature 3).

In cancers, fibroblasts derived from mesenchymal stem cells are known to grow surrounding cancer cells and called cancer-associated fibroblasts (CAF) (Non Patent Literature 4). The cancer-associated fibroblasts are observed in tissues of almost all cancer types and known to exhibit marked growth, particularly, in intractable cancers such as pancreatic cancer, bile duct cancer, breast cancer, and poorly differentiated cancer of the gastrointestinal tract (Non Patent Literatures 4 and 5). MEFLIN is positive in the cancer-associated fibroblasts, and this can be examined by in situ hybridization which detects mRNA derived from the ISLR gene or by immunohistochemical staining using an antibody (Non Patent Literature 5). The in situ hybridization and the immunohistochemical staining employ biopsy materials or surgical materials derived from cancer patients. MEFLIN in cancer tissues is known to be specifically expressed in cancer-associated fibroblasts and is expressed in none of cancer cells, vascular endothelial cells, smooth muscle cells, hematopoietic cells, and nerve cells (Non Patent Literature 5).

There is a report stating that the number of MEFLIN-positive cancer-associated fibroblasts correlates with the prognosis of cancer patients and their response rates to therapy (Non Patent Literature 5 and Patent Literature 2). Specifically, a pancreatic cancer patient group with MEFLIN-positive cancer-associated fibroblasts accounting for 20% or more of all cancer-associated fibroblasts exhibits good prognosis as compared with a patient group with MEFLIN-positive cancer-associated fibroblasts accounting for less than 20% thereof (Non Patent Literature 5). Also, a patient group with MEFLIN-positive cancer-associated fibroblasts accounting for less than 20% of all cancer-associated fibroblasts has been reported to receive a low therapeutic effect (response rate) of immune checkpoint inhibitors (Patent Literature 2).

MEFLIN-positive mesenchymal stem cells or fibroblasts are known to be cells also important for the tissue repair of many organs. For example, in myocardial infarction models of mice, a high level of accumulation of MEFLIN-positive cells is observed at the acute phase after myocardial infarction (Non Patent Literature 6). The expression of MEFLIN in these fibroblasts is essential for myocardial repair, and heart rupture is observed in mice deficient in the ISLR gene (Non Patent Literature 6). There is also a report stating that MEFLIN-positive fibroblasts function to suppress fibrosis and tissue hardening after tissue repair (Non Patent Literature 6).

CITATION LIST

Patent Literature

[Patent Literature 1] WO2017/22472
[Patent Literature 2] WO2019/159825

Non Patent Literature

[Non Patent Literature 1] Nagasawa, A. et al., Genomics, 44: 273-279, 1977.
[Non Patent Literature 2] Maeda K., et al., Sci. Rep., 6: 22288, 2016
[Non Patent Literature 3] Crisan M. et al., Cell Stem Cell., 3: 301-313, 2008
[Non Patent Literature 4] Kobayashi H. et al., Nat Rev Gastroenterol Hepatol., 16: 282-295, 2019
[Non Patent Literature 5] Mizutani Y. et al., Cancer Res., 79: 5367-5381, 2019
[Non Patent Literature 6] Hara A. et al., Circ. Res., 125: 414-430, 2019
[Non Patent Literature 7] Schaum, N. et al., Nature, 562 (7727), 367-372, 2018

SUMMARY OF INVENTION

The present invention provides an anti-MEFLIN antibody for use in the treatment of a cancer in a subject having the cancer, and a pharmaceutical composition comprising the antibody. In the present invention, the cancer can be sarcoma or a MEFLIN-negative cancer.

The present inventors have found that an antibody-drug conjugate of an antibody that binds to MEFLIN protein and a cytotoxic agent exerts an antitumor effect on sarcoma. The present inventors have also found that: MEFLIN-positive cells reside in the stroma of a MEFLIN-negative cancer; and an antibody-drug conjugate of an antibody that binds to MEFLIN protein and a cytotoxic agent exerts an antitumor effect on the cancer. The present invention is based on these findings.

The present invention provides, for example, the following inventions.

[1] A pharmaceutical composition for use in the treatment of a cancer, comprising an antibody-drug conjugate (ADC) of an antibody that binds to MEFLIN and a cytotoxic agent.

[2] The pharmaceutical composition according to [1], wherein the antibody has internalization activity.

[3] The pharmaceutical composition according to [1] or [2], wherein the ADC is ADC in which the antibody and the drug are connected via a linker, wherein the linker has a cleavage site that is intracellularly cleaved.

[4] An antibody that binds to MEFLIN, the antibody being selected from the group consisting of the following antibodies:

(1A) an antibody having a heavy chain variable region comprising heavy chain CDR1 having the amino acid sequence set forth in SEQ ID NO: 1, heavy chain CDR2 having the amino acid sequence set forth in SEQ ID NO: 2, and heavy chain CDR3 having the amino acid sequence set forth in SEQ ID NO: 3, and a light chain variable region comprising light chain CDR1 having the amino acid sequence set forth in SEQ ID NO: 4, light chain CDR2 having the amino acid sequence set forth in SEQ ID NO: 5, and light chain CDR3 having the amino acid sequence set forth in SEQ ID NO: 6;

(1B) an antibody having a heavy chain variable region having the amino acid sequence set forth in SEQ ID NO: 7 and a light chain variable region having the amino acid sequence set forth in SEQ ID NO: 8;

(1C) an antibody that competes with the above-mentioned antibody (1B) for binding to the MEFLIN protein; and (1D) an antibody that binds to an epitope overlapping on the MEFLIN protein with that for the above-mentioned antibody (1B);

(2A) an antibody having a heavy chain variable region comprising the heavy chain CDR1 set forth in SEQ ID NO: 9, the heavy chain CDR2 set forth in SEQ ID NO: 10, and the heavy chain CDR3 set forth in SEQ ID NO: 11, and a light chain variable region comprising the light chain CDR1 set forth in SEQ ID NO: 12, the light chain CDR2 set forth in SEQ ID NO: 13, and the light chain CDR3 set forth in SEQ ID NO: 14;

(2B) an antibody having the heavy chain variable region set forth in SEQ ID NO: 15 and the light chain variable region set forth in SEQ ID NO: 16;

(2C) an antibody that competes with the above-mentioned antibody (2B) for binding to the MEFLIN protein; and (2D) an antibody that binds to an epitope overlapping on the MEFLIN protein with that for the above-mentioned antibody (2B);

(3A) an antibody having a heavy chain variable region comprising the heavy chain CDR1 set forth in SEQ ID NO: 17, the heavy chain CDR2 set forth in SEQ ID NO: 18, and the heavy chain CDR3 set forth in SEQ ID NO: 19, and a light chain variable region comprising the light chain CDR1 set forth in SEQ ID NO: 20, the light chain CDR2 set forth in SEQ ID NO: 21, and the light chain CDR3 set forth in SEQ ID NO: 22;

(3B) an antibody having the heavy chain variable region set forth in SEQ ID NO: 23 and the light chain variable region set forth in SEQ ID NO: 24;

(3C) an antibody that competes with the above-mentioned antibody (3B) for binding to the MEFLIN protein; and (3D) an antibody that binds to an epitope overlapping on the MEFLIN protein with that for the above-mentioned antibody (3B);

(4A) an antibody having a heavy chain variable region comprising the heavy chain CDR1 set forth in SEQ ID NO: 25, the heavy chain CDR2 set forth in SEQ ID NO: 26, and the heavy chain CDR3 set forth in SEQ ID NO: 27, and a light chain variable region comprising the light chain CDR1 set forth in SEQ ID NO: 28, the light chain CDR2 set forth in SEQ ID NO: 29, and the light chain CDR3 set forth in SEQ ID NO: 30;

(4B) an antibody having the heavy chain variable region set forth in SEQ ID NO: 31 and the light chain variable region set forth in SEQ ID NO: 32;

(4C) an antibody that competes with the above-mentioned antibody (4B) for binding to the MEFLIN protein; and (4D) an antibody that binds to an epitope overlapping on the MEFLIN protein with that for the above-mentioned antibody (4B);

(5A) an antibody having a heavy chain variable region comprising the heavy chain CDR1 set forth in SEQ ID NO: 33, the heavy chain CDR2 set forth in SEQ ID NO: 34, and the heavy chain CDR3 set forth in SEQ ID NO: 35, and a light chain variable region comprising the light chain CDR1 set forth in SEQ ID NO: 36, the light chain CDR2 set forth in SEQ ID NO: 37, and the light chain CDR3 set forth in SEQ ID NO: 38;

(5B) an antibody having the heavy chain variable region set forth in SEQ ID NO: 39 and the light chain variable region set forth in SEQ ID NO: 40;

(5C) an antibody that competes with the above-mentioned antibody (5B) for binding to the MEFLIN protein; and (5D) an antibody that binds to an epitope overlapping on the MEFLIN protein with that for the above-mentioned antibody (5B);

(6A) an antibody having a heavy chain variable region comprising the heavy chain CDR1 set forth in SEQ ID NO: 41, the heavy chain CDR2 set forth in SEQ ID NO: 42, and the heavy chain CDR3 set forth in SEQ ID NO: 43, and a light chain variable region comprising the light chain CDR1 set forth in SEQ ID NO: 44, the light chain CDR2 set forth in SEQ ID NO: 45, and the light chain CDR3 set forth in SEQ ID NO: 46;

(6B) an antibody having the heavy chain variable region set forth in SEQ ID NO: 47 and the light chain variable region set forth in SEQ ID NO: 48;

(6C) an antibody that competes with the above-mentioned antibody (6B) for binding to the MEFLIN protein; and (6D) an antibody that binds to an epitope overlapping on the MEFLIN protein with that for the above-mentioned antibody (6B);

(7A) an antibody having a heavy chain variable region comprising the heavy chain CDR1 set forth in SEQ ID NO: 49, the heavy chain CDR2 set forth in SEQ ID NO: 50, and the heavy chain CDR3 set forth in SEQ ID NO: 51, and a light chain variable region comprising the light chain CDR1 set forth in SEQ ID NO: 52, the light chain CDR2 set forth in SEQ ID NO: 53, and the light chain CDR3 set forth in SEQ ID NO: 54;

(7B) an antibody having the heavy chain variable region set forth in SEQ ID NO: 55 and the light chain variable region set forth in SEQ ID NO: 56;

(7C) an antibody that competes with the above-mentioned antibody (7B) for binding to the MEFLIN protein; and (7D) an antibody that binds to an epitope overlapping on the MEFLIN protein with that for the above-mentioned antibody (7B);

(8A) an antibody having a heavy chain variable region comprising the heavy chain CDR1 set forth in SEQ ID NO: 57, the heavy chain CDR2 set forth in SEQ ID NO: 58, and the heavy chain CDR3 set forth in SEQ ID NO: 59, and a light chain variable region comprising the light chain CDR1 set forth in SEQ ID NO: 60, the light chain CDR2 set forth in SEQ ID NO: 61, and the light chain CDR3 set forth in SEQ ID NO: 62;

(8B) an antibody having the heavy chain variable region set forth in SEQ ID NO: 63 and the light chain variable region set forth in SEQ ID NO: 64;

(8C) an antibody that competes with the above-mentioned antibody (8B) for binding to the MEFLIN protein; and (8D) an antibody that binds to an epitope overlapping on the MEFLIN protein with that for the above-mentioned antibody (8B);

(9A) an antibody having a heavy chain variable region comprising the heavy chain CDR1 set forth in SEQ ID NO: 65, the heavy chain CDR2 set forth in SEQ ID NO: 66, and the heavy chain CDR3 set forth in SEQ ID NO: 67, and a light chain variable region comprising the light chain CDR1 set forth in SEQ ID NO: 68, the light chain CDR2 set forth in SEQ ID NO: 69, and the light chain CDR3 set forth in SEQ ID NO: 70;

(9B) an antibody having the heavy chain variable region set forth in SEQ ID NO: 71 and the light chain variable region set forth in SEQ ID NO: 72;

(9C) an antibody that competes with the above-mentioned antibody (9B) for binding to the MEFLIN protein; and (9D) an antibody that binds to an epitope overlapping on the MEFLIN protein with that for the above-mentioned antibody (9B);

(10A) an antibody having a heavy chain variable region comprising the heavy chain CDR1 set forth in SEQ ID NO: 73, the heavy chain CDR2 set forth in SEQ ID NO: 74, and the heavy chain CDR3 set forth in SEQ ID NO: 75, and a light chain variable region comprising the light chain CDR1 set forth in SEQ ID NO: 76, the light chain CDR2 set forth in SEQ ID NO: 77, and the light chain CDR3 set forth in SEQ ID NO: 78;

(10B) an antibody having the heavy chain variable region set forth in SEQ ID NO: 79 and the light chain variable region set forth in SEQ ID NO: 80;

(10C) an antibody that competes with the above-mentioned antibody (10B) for binding to the MEFLIN protein; and (10D) an antibody that binds to an epitope overlapping on the MEFLIN protein with that for the above-mentioned antibody (10B);

(11A) an antibody having a heavy chain variable region comprising the heavy chain CDR1 set forth in SEQ ID NO: 81, the heavy chain CDR2 set forth in SEQ ID NO: 82, and the heavy chain CDR3 set forth in SEQ ID NO: 83, and a light chain variable region comprising the light chain CDR1 set forth in SEQ ID NO: 84, the light chain CDR2 set forth in SEQ ID NO: 85, and the light chain CDR3 set forth in SEQ ID NO: 86;

(11B) an antibody having the heavy chain variable region set forth in SEQ ID NO: 87 and the light chain variable region set forth in SEQ ID NO: 88;

(11C) an antibody that competes with the above-mentioned antibody (11B) for binding to the MEFLIN protein; and (11D) an antibody that binds to an epitope overlapping on the MEFLIN protein with that for the above-mentioned antibody (11B);

(12A) an antibody having a heavy chain variable region comprising the heavy chain CDR1 set forth in SEQ ID NO: 89, the heavy chain CDR2 set forth in SEQ ID NO: 90, and the heavy chain CDR3 set forth in SEQ ID NO: 91, and a light chain variable region comprising the light chain CDR1 set forth in SEQ ID NO: 92, the light chain CDR2 set forth in SEQ ID NO: 93, and the light chain CDR3 set forth in SEQ ID NO: 94;

(12B) an antibody having the heavy chain variable region set forth in SEQ ID NO: 95 and the light chain variable region set forth in SEQ ID NO: 96;

(12C) an antibody that competes with the above-mentioned antibody (12B) for binding to the MEFLIN protein; and (12D) an antibody that binds to an epitope overlapping on the MEFLIN protein with that for the above-mentioned antibody (12B);

(13A) an antibody having a heavy chain variable region comprising the heavy chain CDR1 set forth in SEQ ID NO: 97, the heavy chain CDR2 set forth in SEQ ID NO: 98, and the heavy chain CDR3 set forth in SEQ ID NO: 99, and a light chain variable region comprising the light chain CDR1 set forth in SEQ ID NO: 100, the light chain CDR2 set forth in SEQ ID NO: 101, and the light chain CDR3 set forth in SEQ ID NO: 102;

(13B) an antibody having the heavy chain variable region set forth in SEQ ID NO: 103 and the light chain variable region set forth in SEQ ID NO: 104;

(13C) an antibody that competes with the above-mentioned antibody (13B) for binding to the MEFLIN protein; and (13D) an antibody that binds to an epitope overlapping on the MEFLIN protein with that for the above-mentioned antibody (13B);

(14A) an antibody having a heavy chain variable region comprising the heavy chain CDR1 set forth in SEQ ID NO: 105, the heavy chain CDR2 set forth in SEQ ID NO: 106, and the heavy chain CDR3 set forth in SEQ ID NO: 107, and a light chain variable region comprising the light chain CDR1 set forth in SEQ ID NO: 108, the light chain CDR2 set forth in SEQ ID NO: 109, and the light chain CDR3 set forth in SEQ ID NO: 110;

(14B) an antibody having the heavy chain variable region set forth in SEQ ID NO: 111 and the light chain variable region set forth in SEQ ID NO: 112;

(14C) an antibody that competes with the above-mentioned antibody (14B) for binding to the MEFLIN protein; and (14D) an antibody that binds to an epitope overlapping on the MEFLIN protein with that for the above-mentioned antibody (14B);

(15A) an antibody having a heavy chain variable region comprising the heavy chain CDR1 set forth in SEQ ID NO: 113, the heavy chain CDR2 set forth in SEQ ID NO: 114, and the heavy chain CDR3 set forth in SEQ ID NO: 115, and a light chain variable region comprising the light chain CDR1 set forth in SEQ ID NO: 116, the light chain CDR2 set forth in SEQ ID NO: 117, and the light chain CDR3 set forth in SEQ ID NO: 118;

(15B) an antibody having the heavy chain variable region set forth in SEQ ID NO: 119 and the light chain variable region set forth in SEQ ID NO: 120;

(15C) an antibody that competes with the above-mentioned antibody (15B) for binding to the MEFLIN protein; and (15D) an antibody that binds to an epitope overlapping on the MEFLIN protein with that for the above-mentioned antibody (15B);

(16A) an antibody having a heavy chain variable region comprising the heavy chain CDR1 set forth in SEQ ID NO: 121, the heavy chain CDR2 set forth in SEQ ID NO: 122, and the heavy chain CDR3 set forth in SEQ ID NO: 123, and a light chain variable region comprising the light chain CDR1 set forth in SEQ ID NO: 124, the light chain CDR2 set forth in SEQ ID NO: 125, and the light chain CDR3 set forth in SEQ ID NO: 126;

(16B) an antibody having the heavy chain variable region set forth in SEQ ID NO: 127 and the light chain variable region set forth in SEQ ID NO: 128;

(16C) an antibody that competes with the above-mentioned antibody (16B) for binding to the MEFLIN protein; and (16D) an antibody that binds to an epitope overlapping on the MEFLIN protein with that for the above-mentioned antibody (16B); and (17A) an antibody having a heavy chain variable region comprising the heavy chain CDR1 set forth in SEQ ID NO: 129, the heavy chain CDR2 set forth in SEQ ID NO: 130, and the heavy chain CDR3 set forth in SEQ ID NO: 131, and a light chain variable region comprising the light chain CDR1 set forth in SEQ ID NO: 132, the light chain CDR2 set forth in SEQ ID NO: 133, and the light chain CDR3 set forth in SEQ ID NO: 134;

(17B) an antibody having the heavy chain variable region set forth in SEQ ID NO: 135 and the light chain variable region set forth in SEQ ID NO: 136;

(17C) an antibody that competes with the above-mentioned antibody (17B) for binding to the MEFLIN protein; and (17D) an antibody that binds to an epitope overlapping on the MEFLIN protein with that for the above-mentioned antibody (17B).

[5] A pharmaceutical composition comprising an antibody-drug conjugate (ADC) of an antibody according to [4] and a cytotoxic agent.

[6] The pharmaceutical composition according to [5] for use in the treatment of a cancer.

[7] The pharmaceutical composition according to any of [1] to [3] and [6], wherein the cancer is sarcoma.

[8] The pharmaceutical composition according to [7], wherein the cancer is MEFLIN-positive sarcoma.

[9] The pharmaceutical composition according to [7] or [8], wherein the sarcoma is sarcoma selected from the group consisting of myxofibrosarcoma, malignant fibrous histiocytoma, liposarcoma, leiomyosarcoma, rhabdomyosarcoma, neuroblastoma, malignant peripheral nerve sheath tumor, Ewing's sarcoma, epithelioid sarcoma, clear cell sarcoma, synovial sarcoma, and osteosarcoma.

[10] The pharmaceutical composition according to any of [1] to [3] and [6], wherein the cancer is carcinoma.

[11] The pharmaceutical composition according to [10], wherein the cancer is a cancer selected from the group consisting of breast cancer, pancreatic cancer, lung cancer, colorectal cancer, stomach cancer, bile duct cancer, ovary cancer, bladder cancer, and esophageal cancer.

[12] The pharmaceutical composition according to any of [1] to [3], [6], [10], and [11], wherein the cancer is MEFLIN-negative, and the stroma surrounding the cancer contains MEFLIN-positive cells.

[13] The pharmaceutical composition according to any of [10] to [12], wherein the antibody has no internalization activity.

[14] The pharmaceutical composition according to any of [7] to [9], wherein the antibody has internalization activity.

[15] The pharmaceutical composition according to [13], wherein the ADC is ADC in which the antibody and the drug are connected via a linker, wherein the linker is a cleavable linker.

[16] The pharmaceutical composition according to [15], wherein the linker is a cleavable linker that is cleaved by cathepsin K.

[17] The pharmaceutical composition according to [16], wherein the linker comprises a valine-citrulline dipeptide and is cleaved in the presence of cathepsin K.

[18] The pharmaceutical composition according to any of the above aspects, wherein the linker is a non-cleavable linker.

BRIEF DESCRIPTION OF DRAWINGS

FIG. 1 depicts clone names and information on MEFLIN fragments (the regions of the fragments are represented by amino acid numbers).

FIG. 2 depicts clone names and information on MEFLIN fragments (the regions of the fragments are represented by amino acid numbers).

FIG. 6 also shows results of FACS analysis on an anti-MEFLIN monoclonal antibody-treated group and an untreated group (negative control) of the cells (HEK293 cells) overexpressing human MEFLIN protein. The abscissa depicts the expression level of the MEFLIN protein, and the ordinate depicts the frequency of the cells.

FIG. 7 also shows results of FACS analysis on an anti-MEFLIN monoclonal antibody-treated group and an untreated group (negative control) of the human rhabdomyosarcoma cell line (KYM-1 cells) used. The abscissa depicts the expression level of the MEFLIN protein, and the ordinate depicts the frequency of the cells.

FIG. 8 also shows the expression of human MEFLIN in tissues of the transplanted rhabdomyosarcoma.

FIG. 9 also shows the expression of human MEFLIN in tissues of the transplanted osteosarcoma.

FIG. 10 also shows the expression of mouse MEFLIN in tissues of the transplanted pancreatic cancer and the stroma.

FIG. 11 also shows the expression of mouse MEFLIN in tissues of the transplanted lung cancer and the stroma.

FIG. 12 also shows the expression of human MEFLIN in tissues of the transplanted neuroblastoma.

FIG. 13 also shows the expression of mouse MEFLIN in tissues of the transplanted colorectal cancer and the stroma.

FIG. 14 also shows the expression of mouse MEFLIN in tissues of the transplanted stomach cancer and the stroma.

FIG. 20 also shows the expression of mouse MEFLIN in tissues of the transplanted bile duct cancer and the stroma.

FIG. 21 also shows the expression of mouse MEFLIN in tissues of the transplanted bladder cancer and the stroma.

FIG. 22 also shows the expression of mouse MEFLIN in tissues of the transplanted ovary cancer and the stroma.

FIG. 23 also shows the expression of mouse MEFLIN in tissues of the transplanted esophageal cancer and the stroma.

FIG. 25 also shows the expression of mouse MEFLIN in tissues of the transplanted breast cancer and the stroma.

DESCRIPTION OF EMBODIMENT

Figure 1:
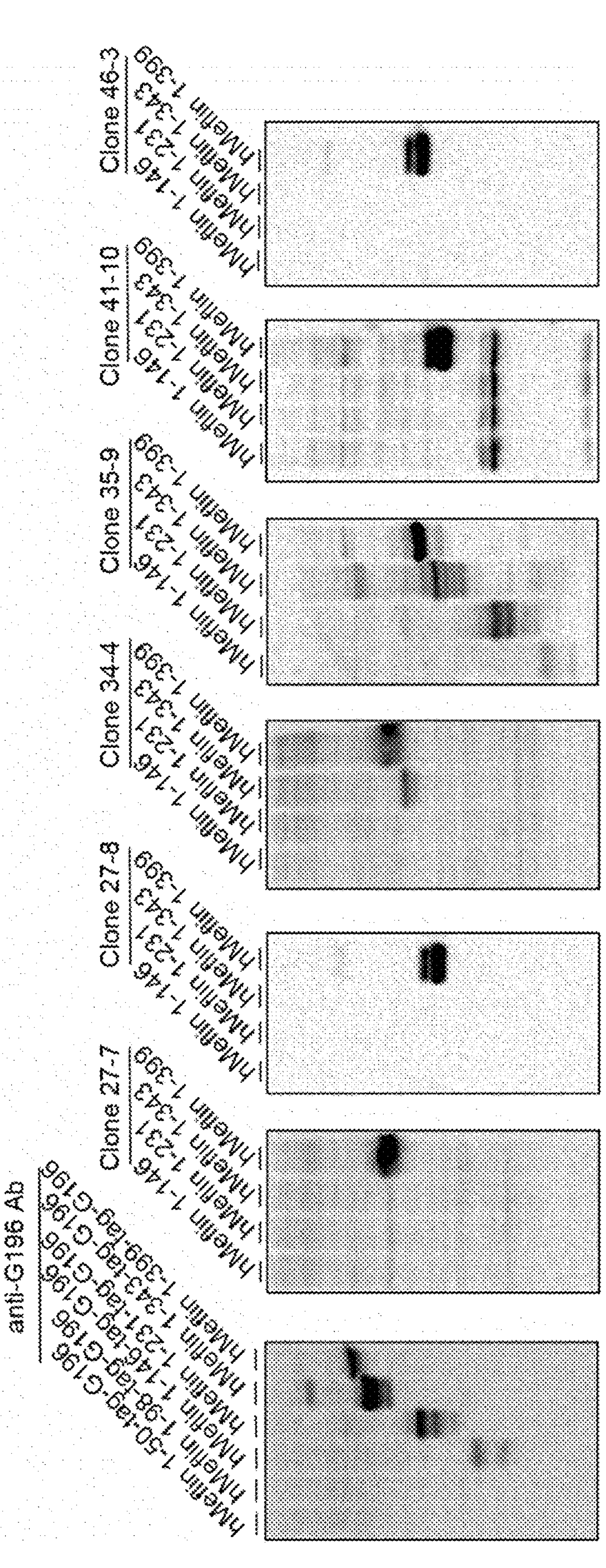
FIG. 1 shows results of Western blotting showing the binding property of a monoclonal antibody obtained from each clone against human MEFLIN protein.

As used herein, the term "subject" means a mammal and can be, particularly, a human.

The term "treatment" is used herein in the meaning including therapy (therapeutic treatment) and prevention (prophylactic treatment). As used herein, the term "therapy" means the therapy, cure, prevention, or improved remission of a disease or a disorder, or reduction in the rate of progression of a disease or a disorder. As used herein, the term "prevention" means decrease in the possibility of onset of a disease or a pathological condition, or delay of the onset of a disease or a pathological condition.

As used herein, the term "disease" means a symptom which would benefit from the therapy. As used herein, the "cancer" means malignant tumor.

As used herein, the term "antibody" means an immunoglobulin and includes a polyclonal antibody and a monoclonal antibody. The antibody is preferably a monoclonal antibody. The origin of the antibody is not particularly limited, but examples thereof include non-human animal antibodies, non-human mammalian antibodies, and human antibodies. The antibody may be a chimeric antibody, a humanized antibody, or a human antibody. The antibody may be a bispecific antibody. For use as a medicament, the antibody can be preferably a chimeric antibody, more preferably a humanized antibody, and further preferably a human antibody. The bispecific antibody can be a monoclonal antibody, preferably a chimeric antibody, more preferably a humanized antibody, and further preferably a human antibody.

As used herein, the term "therapeutically effective amount" means an amount of an agent effective for the treatment (prevention or therapy) of a disease or a state. The therapeutically effective amount of an agent is capable of decreasing the rate of aggravation of a symptom of a disease or a state, stopping the aggravation of the symptom, ameliorating the symptom, curing the symptom, or suppressing the onset or advancement of the symptom.

As used herein, the term "competing" means striving for binding to an antigen against another binding antibody. The competition can occur when the binding sites of two antibodies share a certain antigen. Such antibodies can be obtained by immunization using an epitope as described above, and/or can be obtained by confirming whether or not one antibody decreases the binding of the other antibody to the antigen by competitive assay.

As used herein, the term "antibody-drug conjugate" (hereinafter, also referred to as "ADC") means a substance in which an antibody and a cytotoxic agent are connected. In the ADC, the antibody and the cytotoxic agent can be connected via a suitable linker. A chemotherapeutic agent, a radioisotope, and a toxin can be used as the cytotoxic agent. The ADC also includes a conjugate of an antigen binding fragment of the antibody and a drug.

As used herein, the term "antigen binding fragment" means a portion of an antibody that maintains binding activity against the antigen. The antigen binding fragment can comprise a heavy chain variable region or a light chain variable region, or both, of the antibody of the present invention. The antigen binding fragment may be chimerized or humanized. Examples of the antigen binding fragment include Fab, Fab', $F(ab')_2$, Fv, scFv (single-chain Fv), diabody, and $sc(Fv)_2$ (single-chain $(Fv)_2$). Such a fragment of the antibody can be obtained, for example, by treating the antibody with an enzyme, without particular limitations. For example, Fab can be obtained by digesting the antibody with papain. Alternatively, $F(ab')_2$ can be obtained by digesting the antibody with pepsin, and Fab' can be obtained by further reducing this fragment. In the present invention, such an antigen binding fragment of the antibody can be used.

As used herein, the term "MEFLIN" or "Meflin" is a protein also called immunoglobulin superfamily containing leucine-rich repeat (ISLR). Human MEFLIN can have an amino acid sequence registered under GenBank accession No. BAA85970.1. MEFLIN can be MEFLIN (e.g., human MEFLIN) having an amino acid sequence corresponding to the amino acid sequence registered under GenBank accession No. BAA85970.1. If it is desired to identify the animal species of the origin, MEFLIN is described as human MEFLIN (or hMEFLIN) and mouse MEFLIN (mMEFLIN), etc.

In the present invention, the antibody and the cytotoxic agent in the antibody-drug conjugate (ADC) are connected via a linker. Examples of the cytotoxic agent include chemotherapeutic agents (e.g., anticancer agents such as commercially available anticancer agents, for example, auristatin (auristatin E, auristatin F phenylenediamine (AFP), monomethyl auristatin E, and monomethyl auristatin F, and their derivatives), maytansinoids DM1 and DM4, and their derivatives), camptothecin (SN-38, irinotecan, lurtotecan, DB67, BMP1350, ST1481, CKD602, topotecan and exatecan, and their derivatives), DNA minor groove binding agents (enediyne, lexitropsin, and duocarmycin, and their derivatives), taxane (paclitaxel and docetaxel, and their derivatives), polyketide (discodermolide and its derivatives), anthraquinones (mitoxantrone and its derivatives), benzodiazepine (pyrrolobenzodiazepine, indolinobenzodiazepine, and oxazolidinobenzodiazepine, and their derivatives), vinca alkaloid (vincristine, vinblastine, vindesine, and vinorelbine, and their derivatives), doxorubicin (doxorubicin, morpholino-doxorubicin, and cyanomorpholino-doxorubicin, and their derivatives), cardiac glycoside (digitoxin and its derivatives), calicheamicin, epothilone, cryptophycin, cemadotin, cemadotin, rhizoxin, netropsin, combretastatin, eleutherobin, etoposide, T67 (Tularik Inc.), and nocodazole), radioisotopes (e.g., $^{32}P$, $^{60}C$, $^{90}Y$, $^{111}In$, $^{131}I$, $^{125}I$, $^{153}Sm$, $^{186}Re$, $^{188}Re$, and $^{212}Bi$), and toxins (e.g., diphtheria toxin A, Pseudomonas endotoxin, ricin, and saporin etc.), which can be used as the cytotoxic agent in the ADC of the present invention. Preferably, for example, camptothecin, particularly, SN-38, or exatecan can be used as the cytotoxic agent in the ADC of the present invention. Any of cytotoxic agents for use in therapy of a cancer can be used. Pharmaceutically acceptable salts, solvates (e.g., hydrates), esters, or prodrugs of these cytotoxic agents may be used as the cytotoxic agent.

In the present invention, the linker of the ADC may be a non-cleavable linker or a cleavable linker. Such a linker can be appropriately selected and synthesized by those skilled in the art in the preparation of the ADC. Examples of the cleavable linker include linkers having a degradable bond such as an ester bond. Examples of the cleavable linker include linkers having a protease cleavage site such as a cleavable moiety of a peptide consisting of valine-citrulline or valine-alanine. The peptide region consisting of valine-citrulline can be cleaved by protease such as cathepsin B. In a certain aspect, in the linker, for example, a first spacer may be introduced between the antibody and the cleavable moiety. For example, polyethylene glycol (PEG), for example, PEG having approximately 5 to 40 repeat units per molecule, can be used as the first spacer. A second spacer may be introduced between the cleavable moiety and the cytotoxic agent. For example, p-aminobenzyloxycarbonyl (PABC) can be used as the second spacer. The cleavable linker is physiologically stable at sites other than the site that is cleaved in cancer tissues (particularly, physiologically stable until reaching cancer tissues).

In a certain aspect, the linker comprises the first spacer and the cleavable moiety. In a certain aspect, the linker comprises the first spacer, the cleavable moiety, and the second spacer. For a certain subject, the linker comprises PEG, the cleavable moiety, and PABC.

For the attachment between the antibody and the linker, for example, a sulfhydryl group of the antibody can be connected via a maleimido group.

In a certain aspect, the antibody is connected via its sulfhydryl group to an anticancer agent through a linker having a maleimide-PEG-cleavable moiety. In a certain aspect, the antibody is connected via its sulfhydryl group to an anticancer agent through a linker having a maleimide-PEG-cleavable moiety-PABC.

In a certain aspect, the ADC can have a structure represented by the formula (II) given below.

The ADC of the present invention is considered to be useful as a therapeutic drug for a cancer.

The present invention provides an antibody having the amino acid sequences of heavy chain CDR1 to CDR3 and light chain CDR1 to CDR3 of an antibody produced from a clone selected from clones given below. The antibody is preferably a human chimeric antibody and can be preferably a humanized antibody. In this aspect, the present invention can provide an antibody having the amino acid sequences of a heavy chain variable region and a light chain variable region of an antibody produced from a clone selected from clones given below. The antibody can be preferably a human chimeric antibody.

TABLE 1

Amino acid sequences of CDR1 to CDR3 of heavy chain variable reqion (VH) of antibody produced by rat hybridoma clone

| | VH | | |
|---|---|---|---|
| Clone name | CDR1 | CDR2 | CDR3 |
| 27-7 | KYWMD (SEQ ID NO: 1) | EINTDGSKTNYA PSIKD (SEQ ID NO: 2) | WEDY (SEQ ID NO: 3) |
| 34-4 | GFSLTSYD (SEQ ID NO: 9) | IWGNGNT (SEQ ID NO: 10) | TGGYPY (SEQ ID NO: 11) |
| 27-8 | GYTITSGY (SEQ ID NO: 17) | ITYSGST (SEQ ID NO: 18) | SRDIAAIS FAY (SEQ ID NO: 19) |
| 46-3 | GYTITSGY (SEQ ID NO: 25) | ITYSGST (SEQ ID NO: 26) | ARDFSGIS FAY (SEQ ID NO: 27) |
| 21-3 | GFTFSNYG (SEQ ID NO: 33) | INYDGSST (SEQ ID NO: 34) | ARVEYRFS PFDY (SEQ ID NO: 35) |
| 25-1 | GFDFKTYA (SEQ ID NO: 41) | ISIKTQNYPT (SEQ ID NO: 42) | TVGARY (SEQ ID NO: 43) |
| 41-10 | GFSLTSYD (SEQ ID NO: 49) | IWGNGNT (SEQ ID NO: 50) | TRSLGVG (SEQ ID NO: 51) |
| 35-9 | GFSLSSYG (SEQ ID NO: 57) | IWGNGNT (SEQ ID NO: 58) | ARWESGDY (SEQ ID NO: 59) |

TABLE 2

Amino acid sequences of CDR1 to CDR3 of liqht chain variable reqion (VL) of antibody produced by rat hybridoma clone

| | VL | | |
|---|---|---|---|
| Clone name | CDR1 | CDR2 | CDR3 |
| 27-7 | KSSQSLVYSDG KTYLH (SEQ ID NO: 4) | QVSNLDS (SEQ ID NO: 5) | AQTTHFPYT (SEQ ID NO: 6) |
| 34-4 | QSLVGTGGKTY (SEQ ID NO: 12) | LVS (SEQ ID NO: 13) | LQGTHFPFT (SEQ ID NO: 14) |
| 27-8 | QSLVHSNGNTY (SEQ ID NO: 20) | KVS (SEQ ID NO: 21) | FQATHVPLT (SEQ ID NO: 22) |
| 46-3 | QSLVHSNGNTY (SEQ ID NO: 28) | KVS (SEQ ID NO: 29) | FQATHDPLT (SEQ ID NO: 30) |

TABLE 2-continued

Amino acid sequences of CDR1 to CDR3 of light chain variable region (VL) of antibody produced by rat hybridoma clone

| | VL | | |
|---|---|---|---|
| Clone name | CDR1 | CDR2 | CDR3 |
| 21-3 | QNINKY (SEQ ID NO: 36) | NTN (SEQ ID NO: 37) | LQRNSWLT (SEQ ID NO: 38) |
| 25-1 | QSLLHSNGNTY (SEQ ID NO: 44) | LVS (SEQ ID NO: 45) | VQSTHAPLT (SEQ ID NO: 46) |
| 41-10 | QDIGDY (SEQ ID NO: 52) | GAT (SEQ ID NO: 53) | LQSKESPCSR (SEQ ID NO: 54) |
| 35-9 | QSLVGSGGKTY (SEQ ID NO: 60) | LVS (SEQ ID NO: 61) | LQGTHF PWT (SEQ ID NO: 62) |

TABLE 3

Amino acid sequence of heavy chain variable region (VH) of antibody produced by rat hybridoma clone

| Clone name | VH |
|---|---|
| 27-7 | EVQLVESGGSLVQPGGSLKLSCVASGYTPSKYWMDWVRQTPGKSLEWIGEINTDGSKTNYAPSIKDRFTISRDNAKSTLYLQMSNVKSDDTAIYYCTNWEDYWGQGVMVTVSS (SEQ ID NO: 7) |
| 34-4 | QVQLMESGPGLVQPSQTLSLTCTVSGFSLTSYDMHWVRQPPGKGLEWMGVIWGNGNTHYNSALKSRLSISRDTSKSQVFLKMNSLQTENTAIYFCTGGYFYWGQGVTVTVSS (SEQ ID NO: 15) |
| 27-8 | VQLTESGPGLVKPSQSLSLTCSVTGYTITSGYDWSWIRKFPGNKMEWMGYITYSGSTNYNPSLKSRISITRDTSKNQFFLQLNSVTTEDTATYYCSRDIAAISFAYWGQGTLVTVSS (SEQ ID NO: 23) |
| 46-3 | VQLKESGPGLVKPSQSLSLTCSVTGYTITSGYDWSWIRKFPGNKMEWMGFITYSGSTHHNPSLKSRISITRDTSRNQFFLQLNSVTTEDSATYYCARDPSGISPAYWGQGTLVSVSS (SEQ ID NO: 31) |
| 21-3 | VQLMESGGGLVQPGRSLKLSCAASGPTPSNYGMAWVRQAPTKGLEWVATINYDGSSTYYRDSVKGRFTISRDNAKSTLYLQMDSLRSEDTATYYCARVEYRFSPFDYWGQGVTATVSS (SEQ ID NO: 39) |
| 25-1 | EVQLVESGGGLVQPKGSLKLSCAASGFDFKTYAMSWVRQAPGKGLDWVASISIKTQNYPTLYADSVKERPTISRDDSQSMVYLHMNN1KTEDTALYYCTVGARYWGQGVMTTVSS (SEQ ID NO: 47) |
| 41-10 | QVQLTESGPGLVQPSQTLSLTCTVSGFSLTSYDMHWVRQPPGKGLEWMGVIWGNGNTHYNSALKSRLSISRDTSKRQVFLKMNSLQTEDTAIYFCTRSLGVGWGQGVMIIVSS (SEQ ID NO: 55) |
| 35-9 | QVQLTESGPGLVQPSQTLSLTCTVSGFSLSSYGVIWVRQPPGKGLEWMGVIWGNGNTNYNSTLKSRLSISRDTSKSQVPLKMNILQTEDTAMYFCARWESGDYWGQGVTVTVSS (SEQ ID NO: 63) |

TABLE 4

Amino acid sequence of light chain variable region (VL) of antibody produced by rat hybridoma clone

| Clone name | VL |
|---|---|
| 27-7 | DVVMTQTPPSLSVAIGQSVSISCKSSQSLVYSDGKTYLHWLLQSSGRSPKRLIYQVSNLDSGVPDRFSGTGSQKDFTLKISRVEAKDLGVYYCAQTTHFPYTFGAGTKLELK (SEQ ID NO: 8) |
| 34-4 | DVVMTQTPVSLSVAIGHPASISCKSSQSLVGTGGKTYLSWLLQRPGQSPKRLIYLVSKLDSGIPDRFSGSGSETDFTLKISRVEADDLGVYYCLQGTHFPFTPGSGTQLEMK (SEQ ID NO: 16) |
| 27-8 | DVVMTQTPVAQPVTLGDQASISCRSSQSLVHSNGNTYLEWYLQKPGQSPQLLIYKVSNRFSGVPDRFIGSGSGSDFTLKISRVEPEDLGVYYCFQATHVPLTFGSGTKLEIK (SEQ ID NO: 24) |
| 46-3 | DVVLTQTPVAQPVTLGDQVSISCRSSQSLVHSNGNTYLEWYLQKPGQSPQLLIYKVSNRFSGVPDRFIGSGSGSDPTLKISRVEPEDLGIYYCFQATHDPLTFGSGTKLEIK (SEQ ID NO: 32) |
| 21-3 | DVQLTQSPSFLSASVGERVTLSCKASQNINKYLDWYQQKLGEAPKLLIYNTNNLHTGIPSRFSGSGSGTDYTLTISSLQPEDVATYFCLQRNSWLTFGSGTKLEIK (SEQ ID NO: 40) |
| 25-1 | DVVMTQTPPTLSATIGQSVSISCRSSQSLLHSNGNTYLNWLLQRPGQPPQVLIYLVSRLESGVPNRFSGSGSGTDFTLKISGVEAEDLGVYYCVQSTHAPLTPGSGTKLEIK (SEQ ID NO: 48) |
| 41-10 | VQMTQAPSSLPASLGDRVTITCRASQDIGDYLRWRQQKPGKSPRLMIYGATNLAAGVPSRFSGSRSGSDYSLTISSLESEDMADYYCLQSKESPCSRSVLGPNWRSN (SEQ ID NO: 56) |
| 35-9 | DVVMTQTPVSLSVAVGQPASISCTSSQSLVGSGGKTYLNWFLQRPGQSPKRLISLVSKLDSGIPDRFSGSGSETDFTLKISRVEADDLGVYYCLQGTHFPWTFGGGTKQELK (SEQ ID NO: 64) |

TABLE 5

Amino acid sequences of CDR1 to CDR3 of heavy chain variable region (VH) of antibody produced by mouse hybridoma clone

| | VH | | |
|---|---|---|---|
| Clone name | CDR1 | CDR2 | CDR3 |
| 3-2 | GFTFSDYG (SEQ ID NO: 65) | ISSLAYTV (SEQ ID NO: 66) | ARFPVEAMDY (SEQ ID NO: 67) |
| 11-8 | GYSFTDYI (SEQ ID NO: 73) | INPYSGNT (SEQ ID NO: 74) | ARDGDDYAMDY (SEQ ID NO: 75) |
| 16-5 | GFTFSDYG (SEQ ID NO: 81) | ISSLAYTV (SEQ ID NO: 82) | ARFPVEAMDY (SEQ ID NO: 83) |
| 19-7 | GYTFTSYW (SEQ ID NO: 89) | IYPCNGRT (SEQ ID NO: 90) | ARWDWVFDY (SEQ ID NO: 91) |
| 22-3 | GFTFSDYG (SEQ ID NO: 97) | 1SSLAYTV (SEQ ID NO: 98) | ARFPVEAMDY (SEQ ID NO: 99) |
| 23-1 | GYSFTDY1 (SEQ ID NO: 105) | INPYYGST (SEQ ID NO: 106) | ARDGTDYAMDY (SEQ ID NO: 107) |
| 8-2 | GYTITDYY (SEQ ID NO: 113) | INPYNGGT (SEQ ID NO: 114) | ARSRTGGNGMDY (SEQ ID NO: 115) |
| 13-1 | GYSFTGYF (SEQ ID NO: 121) | INPYNGDT (SEQ ID NO: 122) | AKWDLYDGYFRDY (SEQ ID NO: 123) |
| 32-1 | GFTFSSYG (SEQ ID NO: 129) | ISGGSYT (SEQ ID NO: 130) | VIDYDVMDY (SEQ ID NO: 131) |

TABLE 6

Amino acid sequences of CDR1 to CDR3 of light chain variable region (VL) of antibody produced by mouse hybridoma clone

| Clone | VL | | |
|---|---|---|---|
| name | CDR1 | CDR2 | CDR3 |
| 3-2 | ESVDNYGISF (SEQ ID NO: 68) | AAS SEQ ID NO: 69) | QQSKEVPPT (SEQ ID NO: 70) |
| 11-8 | QSIVHSNGNTY (SEQ ID NO: 76) | KVS (SEQ ID NO: 77) | FQGSHVPWT (SEQ ID NO: 78) |
| 16-5 | QSLVHSNGNTY (SEQ ID NO: 84) | KVS (SEQ ID NO: 85) | SQSTHFLT (SEQ ID NO: 86) |
| 19-7 | KSVSTSGYSY (SEQ ID NO: 92) | LVS (SEQ ID NO: 93) | QHIRELTR (SEQ ID NO: 94) |
| 22-3 | KSVSTSGYSY (SEQ ID NO: 100) | LVS (SEQ ID NO: 101) | QHIRELTR (SEQ ID NO: 102) |
| 23-1 | KSVSTSGYSY (SEQ ID NO: 108) | LVS (SEQ ID NO: 109) | QHIRELTR (SEQ ID NO: 110) |
| 8-2 | KSVSTSGYSY (SEQ ID NO: 116) | LVS (SEQ ID NO: 117) | QHIRELTR (SEQ ID NO: 118) |
| 13-1 | KSVSTSGYSY (SEQ ID NO: 124) | LVS (SEQ ID NO: 125) | QHIRELTR (SEQ ID NO: 126) |
| 32-1 | QSLLNSRTRKNY (SEQ ID NO: 132) | WAS (SEQ ID NO: 133) | KQSYNLRT (SEQ ID NO: 134) |

TABLE 7

Amino acid sequence of heavy chain variable region (VH) of antibody produced by mouse hybridoma clone

| Clone name | VH |
|---|---|
| 3-2 | VQLQESGGGLVQPGGSRKLSCAASGFTFSDYGMA<br>WVRQAPGKGPEWVAFISSLAYTVYYADTVTGRFT<br>ISRENAKNTLFLEMSSLRSEDTAMYYCARFPVEA<br>MDYWGQGTSVTVSS<br>(SEQ ID NO: 71) |
| 11-8 | VQLQESGPELVKPGASVKISCKASGYSFTDYIIL<br>WVKQSHGKSLEWIGNINPYSGNTRYNLKFKGKAT<br>LTVDKSSSTAYMQLNSLTSEDSAVYYCARDGDDY<br>AMDYWGQGTSVTVSS<br>(SEQ ID NO: 79) |
| 16-5 | VKLQQSGGGLVQPGGSRKLSCAASGFTPSDYGMA<br>WVRQAPGKGPEWVAFISSLAYTVYYADTVTGRFT<br>ISRENAKNTLFLEMSSLRSEDTAMYYCARFPVEA<br>MDYWGQGTSVTVSS<br>(SEQ ID NO: 87) |
| 19-7 | QVKLQESGAELVKPGASVKLSCKASGYTFTSYWM<br>HWVKQRPGQGLDWIGEIYPCNGRTNYNEKPKSKA<br>TLTVDKSSSTAYMQLSSLTSEDSAVYYCARWDWV<br>FDYWGQGTTLTVSS<br>(SEQ ID NO: 95) |
| 22-3 | VKLQESGGGLVQPGGSRKLSCAASGFTFSDYGMA<br>WVRQAPGKGPEWVAFISSLAYTVYYADTVTGRFT<br>ISRENAKNTLFLEMSSLRSEDTAMYYCARFPVEA<br>MDYWGQGTSVTVSS<br>(SEQ ID NO: 103) |
| 23-1 | VQLQESGPELVKPGASVKISCKASGYSFTDYIML<br>WLKQSHGKSLEWIGNINPYYGSTRYNLKFKGKAT<br>LTVDKSSSTAYMQLNSLTSEDSAVYYCARDGTDY<br>AMDYWGQGTSVTVSS<br>(SEQ ID NO: 111) |
| 8-2 | VQLQESGPVLVKPGASVKMSCKASGYTITDYYMN<br>WVKQSHGKSLEWIGVINPYNGGTSYNQKFKGKAT<br>LTVDKSSSTAYMELNSLTSEDSAVYYCARSRTGG<br>NGMDYWGQGTSVTVSS<br>(SEQ ID NO: 119) |
| 13-1 | VKLQESGPELVKPGASVKISCKASGYSFTGYFMN<br>WVMQSHGKSLEWIGRINPYNGDTFYNQKFKGKAT<br>LTVDKSSSTAHMELRSLASEDSAVYYCAKWDLYD<br>GYFRDYWGQGTTLTVSS<br>(SEQ ID NO: 127) |
| 32-1 | VQLQQSGGDLVKPGGSLKLSCAASGFTFSSYGMS<br>WVRQTPDKRLEWVATISSGGSYTYYPDSVKGRFT<br>ISRDNAKNTLYLQMSSLKSEDTAMYYCVIDYDVM<br>DYWGQGTSVTVSS<br>(SEQ ID NO: 135) |

TABLE 8

Amino acid sequence of light chain variable region (VL) of antibody produced by mouse hybridoma clone

| Clone name | VL |
|---|---|
| 3-2 | IGQRATISCRASESVDNYGISFMNWFQQKPGQP<br>PKLLIYAASNQGSGVPARFSGSGSGTDFSLNIH<br>PMEEDDTAMYFCQQSKEVPPTFGGGTKLEIK<br>(SEQ ID NO: 72) |
| 11-8 | DIVITQTPLSLPVSLGDQASISCRSSQSIVHSN<br>GNTYLEWYLQKPGQSPRLLIYKVSNRFSGVPDR<br>FSGSGSGTDFTLKISRVETEDLGVYYCFQGSHV<br>PWTFGGGTKLEIK<br>(SEQ ID NO: 80) |
| 16-5 | DIVMTQTPLSLPVSLGDQASISCRSSQSLVHSN<br>GNTYLHWYLQKPGQSPKLLIYKVSNRFSGVPDR<br>FSGSGSGTDFTLKISRVEAEDLGVYFCSQSTHF<br>LTFGSGTKLEIK<br>(SEQ ID NO: 88) |
| 19-7 | RASKSVSTSGYSYMHWNQQKPGQPPRLLIYLVS<br>NPESGVPARFSGSGSGTDFTLNIHPVEEEDAAT<br>YYCQHIRELTRSEGGPSWK<br>(SEQ ID NO: 96) |
| 22-3 | RASKSVSTSGYSYMHWNQQKPGQPPRLLIYLVS<br>NLESGVPARFSGSGSGTDFTLNIHPVEEEDAAT<br>YYCQHIRELTRSEGGPSWK<br>(SEQ ID NO: 104) |
| 23-1 | RASKSVSTSGYSYMHWNQQKPGQPPRLLIYLVS<br>NLESGVPARFSGSGSGTDFTLNIHPVEEEDAAT<br>YYCQHIRELTRSEGGPSWK<br>(SEQ ID NO: 112) |
| 8-2 | DIVLTQSPASLAVSLGQRATISYRASKSVSTSG<br>YSYMHWNQQKPGQPPRLLIYLVSNLESGVPARF<br>SGSGSGTDFTLNIHPVEEEDAATYYCQHIRELT<br>RSEGGPSWK<br>(SEQ ID NO: 120) |
| 13-1 | DIVMTQSPASLAVSLGQRATISYRASKSVSTSG<br>YSYMHWNQQKPGQPPRLLIYLVSNLESGVPARF<br>SGSGSGTDFTLNIHPVEEEDAATYYCQHIRELT<br>RSEGGPSWK<br>(SEQ ID NO: 128) |
| 32-1 | DIVMTQTPSSLAVSAGEKVTMSCKSSQSLLNSR<br>TRKNYLAWYQQKPGQSPKLLIYWASTRESGVPD<br>RFTGSGSGTDFTLTISSVQAEDLAVYYCKQSYN<br>LRTFGGGTKLEIK<br>(SEQ ID NO: 136) |

The present invention provides an antibody that binds to the MEFLIN protein, the antibody being any of:

(1A) an antibody having a heavy chain variable region comprising the heavy chain CDR1 set forth in SEQ ID NO: 1, the heavy chain CDR2 set forth in SEQ ID NO: 2, and the heavy chain CDR3 set forth in SEQ ID NO: 3, and a light chain variable region comprising the light chain CDR1 set forth in SEQ ID NO: 4, the light chain CDR2 set forth in SEQ ID NO: 5, and the light chain CDR3 set forth in SEQ ID NO: 4;

(1B) an antibody having a heavy chain variable region set forth in SEQ ID NO: 7 and a light chain variable region set forth in SEQ ID NO: 8;

(1C) an antibody that competes with the above-mentioned antibody (1B) for binding to the MEFLIN protein; and (1D) an antibody that binds to an epitope overlapping on the MEFLIN protein with that for the above-mentioned antibody (1B).

The antibody is preferably a human chimeric antibody and can be preferably a humanized antibody.

The present invention provides an antibody that binds to the MEFLIN protein, the antibody being any of:

(2A) an antibody having a heavy chain variable region comprising the heavy chain CDR1 set forth in SEQ ID NO: 9, the heavy chain CDR2 set forth in SEQ ID NO: 10, and the heavy chain CDR3 set forth in SEQ ID NO: 11, and a light chain variable region comprising the light chain CDR1 set forth in SEQ ID NO: 12, the light chain CDR2 set forth in SEQ ID NO: 13, and the light chain CDR3 set forth in SEQ ID NO: 14;

(2B) an antibody having the heavy chain variable region set forth in SEQ ID NO: 15 and the light chain variable region set forth in SEQ ID NO: 16;

(2C) an antibody that competes with the above-mentioned antibody (2B) for binding to the MEFLIN protein; and (2D) an antibody that binds to an epitope overlapping on the MEFLIN protein with that for the above-mentioned antibody (2B).

The antibody is preferably a human chimeric antibody and can be preferably a humanized antibody.

The present invention provides an antibody that binds to the MEFLIN protein, the antibody being any of:

(3A) an antibody having a heavy chain variable region comprising the heavy chain CDR1 set forth in SEQ ID NO: 17, the heavy chain CDR2 set forth in SEQ ID NO: 18, and the heavy chain CDR3 set forth in SEQ ID NO: 19, and a light chain variable region comprising the light chain CDR1 set forth in SEQ ID NO: 20, the light chain CDR2 set forth in SEQ ID NO: 21, and the light chain CDR3 set forth in SEQ ID NO: 22;

(3B) an antibody having the heavy chain variable region set forth in SEQ ID NO: 23 and the light chain variable region set forth in SEQ ID NO: 24;

(3C) an antibody that competes with the above-mentioned antibody (3B) for binding to the MEFLIN protein; and (3D) an antibody that binds to an epitope overlapping on the MEFLIN protein with that for the above-mentioned antibody (3B).

The antibody is preferably a human chimeric antibody and can be preferably a humanized antibody.

The present invention provides an antibody that binds to the MEFLIN protein, the antibody being any of:

(4A) an antibody having a heavy chain variable region comprising the heavy chain CDR1 set forth in SEQ ID NO: 25, the heavy chain CDR2 set forth in SEQ ID NO: 26, and the heavy chain CDR3 set forth in SEQ ID NO: 27, and a light chain variable region comprising the light chain CDR1 set forth in SEQ ID NO: 28, the light chain CDR2 set forth in SEQ ID NO: 29, and the light chain CDR3 set forth in SEQ ID NO: 30;

(4B) an antibody having the heavy chain variable region set forth in SEQ ID NO: 31 and the light chain variable region set forth in SEQ ID NO: 32;

(4C) an antibody that competes with the above-mentioned antibody (4B) for binding to the MEFLIN protein; and (4D) an antibody that binds to an epitope overlapping on the MEFLIN protein with that for the above-mentioned antibody (4B).

The antibody is preferably a human chimeric antibody and can be preferably a humanized antibody.

The present invention provides an antibody that binds to the MEFLIN protein, the antibody being any of:

(5A) an antibody having a heavy chain variable region comprising the heavy chain CDR1 set forth in SEQ ID NO: 33, the heavy chain CDR2 set forth in SEQ ID NO: 34, and the heavy chain CDR3 set forth in SEQ ID NO: 35, and a light chain variable region comprising the light chain CDR1 set forth in SEQ ID NO: 36, the light chain CDR2 set forth in SEQ ID NO: 37, and the light chain CDR3 set forth in SEQ ID NO: 38;

(5B) an antibody having the heavy chain variable region set forth in SEQ ID NO: 39 and the light chain variable region set forth in SEQ ID NO: 40;

(5C) an antibody that competes with the above-mentioned antibody (5B) for binding to the MEFLIN protein; and (5D) an antibody that binds to an epitope overlapping on the MEFLIN protein with that for the above-mentioned antibody (5B).

The antibody is preferably a human chimeric antibody and can be preferably a humanized antibody.

The present invention provides an antibody that binds to the MEFLIN protein, the antibody being any of:

(6A) an antibody having a heavy chain variable region comprising the heavy chain CDR1 set forth in SEQ ID NO: 41, the heavy chain CDR2 set forth in SEQ ID NO: 42, and the heavy chain CDR3 set forth in SEQ ID NO: 43, and a light chain variable region comprising the light chain CDR1 set forth in SEQ ID NO: 44, the light chain CDR2 set forth in SEQ ID NO: 45, and the light chain CDR3 set forth in SEQ ID NO: 46;

(6B) an antibody having the heavy chain variable region set forth in SEQ ID NO: 47 and the light chain variable region set forth in SEQ ID NO: 48;

(6C) an antibody that competes with the above-mentioned antibody (6B) for binding to the MEFLIN protein; and (6D) an antibody that binds to an epitope overlapping on the MEFLIN protein with that for the above-mentioned antibody (6B).

The antibody is preferably a human chimeric antibody and can be preferably a humanized antibody.

The present invention provides an antibody that binds to the MEFLIN protein, the antibody being any of:

(7A) an antibody having a heavy chain variable region comprising the heavy chain CDR1 set forth in SEQ ID NO: 49, the heavy chain CDR2 set forth in SEQ ID NO: 50, and the heavy chain CDR3 set forth in SEQ ID NO: 51, and a light chain variable region comprising the light chain CDR1 set forth in SEQ ID NO: 52, the light chain CDR2 set forth in SEQ ID NO: 53, and the light chain CDR3 set forth in SEQ ID NO: 54;

(7B) an antibody having the heavy chain variable region set forth in SEQ ID NO: 55 and the light chain variable region set forth in SEQ ID NO: 56;

(7C) an antibody that competes with the above-mentioned antibody (7B) for binding to the MEFLIN protein; and (7D) an antibody that binds to an epitope overlapping on the MEFLIN protein with that for the above-mentioned antibody (7B).

The antibody is preferably a human chimeric antibody and can be preferably a humanized antibody.

The present invention provides an antibody that binds to the MEFLIN protein, the antibody being any of:

(8A) an antibody having a heavy chain variable region comprising the heavy chain CDR1 set forth in SEQ ID NO: 57, the heavy chain CDR2 set forth in SEQ ID NO: 58, and the heavy chain CDR3 set forth in SEQ ID NO: 59, and a light chain variable region comprising the light chain CDR1 set forth in SEQ ID NO: 60, the light chain CDR2 set forth in SEQ ID NO: 61, and the light chain CDR3 set forth in SEQ ID NO: 62;

(8B) an antibody having the heavy chain variable region set forth in SEQ ID NO: 63 and the light chain variable region set forth in SEQ ID NO: 64;

(8C) an antibody that competes with the above-mentioned antibody (8B) for binding to the MEFLIN protein; and (8D) an antibody that binds to an epitope overlapping on the MEFLIN protein with that for the above-mentioned antibody (8B).

The antibody is preferably a human chimeric antibody and can be preferably a humanized antibody.

The present invention provides an antibody that binds to the MEFLIN protein, the antibody being any of:

(9A) an antibody having a heavy chain variable region comprising the heavy chain CDR1 set forth in SEQ ID NO: 65, the heavy chain CDR2 set forth in SEQ ID NO: 66, and the heavy chain CDR3 set forth in SEQ ID NO: 67, and a light chain variable region comprising the light chain CDR1 set forth in SEQ ID NO: 68, the light chain CDR2 set forth in SEQ ID NO: 69, and the light chain CDR3 set forth in SEQ ID NO: 70;

(9B) an antibody having the heavy chain variable region set forth in SEQ ID NO: 71 and the light chain variable region set forth in SEQ ID NO: 72;

(9C) an antibody that competes with the above-mentioned antibody (9B) for binding to the MEFLIN protein; and (9D) an antibody that binds to an epitope overlapping on the MEFLIN protein with that for the above-mentioned antibody (9B).

The antibody is preferably a human chimeric antibody and can be preferably a humanized antibody.

The present invention provides an antibody that binds to the MEFLIN protein, the antibody being any of:

(10A) an antibody having a heavy chain variable region comprising the heavy chain CDR1 set forth in SEQ ID NO: 73, the heavy chain CDR2 set forth in SEQ ID NO: 74, and the heavy chain CDR3 set forth in SEQ ID NO: 75, and a light chain variable region comprising the light chain CDR1 set forth in SEQ ID NO: 76, the light chain CDR2 set forth in SEQ ID NO: 77, and the light chain CDR3 set forth in SEQ ID NO: 78;

(10B) an antibody having the heavy chain variable region set forth in SEQ ID NO: 79 and the light chain variable region set forth in SEQ ID NO: 80;

(10C) an antibody that competes with the above-mentioned antibody (10B) for binding to the MEFLIN protein; and (10D) an antibody that binds to an epitope overlapping on the MEFLIN protein with that for the above-mentioned antibody (10B).

The antibody is preferably a human chimeric antibody and can be preferably a humanized antibody.

The present invention provides an antibody that binds to the MEFLIN protein, the antibody being any of:

(11A) an antibody having a heavy chain variable region comprising the heavy chain CDR1 set forth in SEQ ID NO: 81, the heavy chain CDR2 set forth in SEQ ID NO: 82, and the heavy chain CDR3 set forth in SEQ ID NO: 83, and a light chain variable region comprising the light chain CDR1 set forth in SEQ ID NO: 84, the light chain CDR2 set forth in SEQ ID NO: 85, and the light chain CDR3 set forth in SEQ ID NO: 86;

(11B) an antibody having the heavy chain variable region set forth in SEQ ID NO: 87 and the light chain variable region set forth in SEQ ID NO: 88;

(11C) an antibody that competes with the above-mentioned antibody (11B) for binding to the MEFLIN protein; and (11D) an antibody that binds to an epitope overlapping on the MEFLIN protein with that for the above-mentioned antibody (11B).

The antibody is preferably a human chimeric antibody and can be preferably a humanized antibody.

The present invention provides an antibody that binds to the MEFLIN protein, the antibody being any of:

(12A) an antibody having a heavy chain variable region comprising the heavy chain CDR1 set forth in SEQ ID NO: 89, the heavy chain CDR2 set forth in SEQ ID NO: 90, and the heavy chain CDR3 set forth in SEQ ID NO: 91, and a light chain variable region comprising the light chain CDR1 set forth in SEQ ID NO: 92, the light chain CDR2 set forth in SEQ ID NO: 93, and the light chain CDR3 set forth in SEQ ID NO: 94;

(12B) an antibody having the heavy chain variable region set forth in SEQ ID NO: 95 and the light chain variable region set forth in SEQ ID NO: 96;

(12C) an antibody that competes with the above-mentioned antibody (12B) for binding to the MEFLIN protein; and (12D) an antibody that binds to an epitope overlapping on the MEFLIN protein with that for the above-mentioned antibody (12B).

The antibody is preferably a human chimeric antibody and can be preferably a humanized antibody.

The present invention provides an antibody that binds to the MEFLIN protein, the antibody being any of:

(13A) an antibody having a heavy chain variable region comprising the heavy chain CDR1 set forth in SEQ ID NO: 97, the heavy chain CDR2 set forth in SEQ ID NO: 98, and the heavy chain CDR3 set forth in SEQ ID NO: 99, and a light chain variable region comprising the light chain CDR1 set forth in SEQ ID NO: 100, the light chain CDR2 set forth in SEQ ID NO: 101, and the light chain CDR3 set forth in SEQ ID NO: 102;

(13B) an antibody having the heavy chain variable region set forth in SEQ ID NO: 103 and the light chain variable region set forth in SEQ ID NO: 104;

(13C) an antibody that competes with the above-mentioned antibody (13B) for binding to the MEFLIN protein; and (13D) an antibody that binds to an epitope overlapping on the MEFLIN protein with that for the above-mentioned antibody (13B).

The antibody is preferably a human chimeric antibody and can be preferably a humanized antibody.

The present invention provides an antibody that binds to the MEFLIN protein, the antibody being any of:

(14A) an antibody having a heavy chain variable region comprising the heavy chain CDR1 set forth in SEQ ID NO: 105, the heavy chain CDR2 set forth in SEQ ID NO: 106, and the heavy chain CDR3 set forth in SEQ ID NO: 107, and a light chain variable region comprising the light chain CDR1 set forth in SEQ ID NO: 108, the light chain CDR2 set forth in SEQ ID NO: 109, and the light chain CDR3 set forth in SEQ ID NO: 110;

(14B) an antibody having the heavy chain variable region set forth in SEQ ID NO: 111 and the light chain variable region set forth in SEQ ID NO: 112;

(14C) an antibody that competes with the above-mentioned antibody (14B) for binding to the MEFLIN protein; and (14D) an antibody that binds to an epitope overlapping on the MEFLIN protein with that for the above-mentioned antibody (14B).

The antibody is preferably a human chimeric antibody and can be preferably a humanized antibody.

The present invention provides an antibody that binds to the MEFLIN protein, the antibody being any of:

(15A) an antibody having a heavy chain variable region comprising the heavy chain CDR1 set forth in SEQ ID NO: 113, the heavy chain CDR2 set forth in SEQ ID NO: 114, and the heavy chain CDR3 set forth in SEQ ID NO: 115, and a light chain variable region comprising the light chain CDR1 set forth in SEQ ID NO: 116, the light chain CDR2 set forth in SEQ ID NO: 117, and the light chain CDR3 set forth in SEQ ID NO: 118;

(15B) an antibody having the heavy chain variable region set forth in SEQ ID NO: 119 and the light chain variable region set forth in SEQ ID NO: 120;

(15C) an antibody that competes with the above-mentioned antibody (15B) for binding to the MEFLIN protein; and (15D) an antibody that binds to an epitope overlapping on the MEFLIN protein with that for the above-mentioned antibody (15B).

The antibody is preferably a human chimeric antibody and can be preferably a humanized antibody.

The present invention provides an antibody that binds to the MEFLIN protein, the antibody being any of:

(16A) an antibody having a heavy chain variable region comprising the heavy chain CDR1 set forth in SEQ ID NO: 121, the heavy chain CDR2 set forth in SEQ ID NO: 122, and the heavy chain CDR3 set forth in SEQ ID NO: 123, and a light chain variable region comprising the light chain CDR1 set forth in SEQ ID NO: 124, the light chain CDR2 set forth in SEQ ID NO: 125, and the light chain CDR3 set forth in SEQ ID NO: 126;

(16B) an antibody having the heavy chain variable region set forth in SEQ ID NO: 127 and the light chain variable region set forth in SEQ ID NO: 128;

(16C) an antibody that competes with the above-mentioned antibody (16B) for binding to the MEFLIN protein; and (16D) an antibody that binds to an epitope overlapping on the MEFLIN protein with that for the above-mentioned antibody (16B).

The antibody is preferably a human chimeric antibody and can be preferably a humanized antibody.

The present invention provides an antibody that binds to the MEFLIN protein, the antibody being any of:

(17A) an antibody having a heavy chain variable region comprising the heavy chain CDR1 set forth in SEQ ID NO: 129, the heavy chain CDR2 set forth in SEQ ID NO: 130, and the heavy chain CDR3 set forth in SEQ ID NO: 131, and a light chain variable region comprising the light chain CDR1 set forth in SEQ ID NO: 132, the light chain CDR2 set forth in SEQ ID NO: 133, and the light chain CDR3 set forth in SEQ ID NO: 134;

(17B) an antibody having the heavy chain variable region set forth in SEQ ID NO: 135 and the light chain variable region set forth in SEQ ID NO: 136;

(17C) an antibody that competes with the above-mentioned antibody (17B) for binding to the MEFLIN protein; and (17D) an antibody that binds to an epitope overlapping on the MEFLIN protein with that for the above-mentioned antibody (17B).

The antibody is preferably a human chimeric antibody and can be preferably a humanized antibody.

In a certain aspect of the present invention, the antibody that binds to the MEFLIN protein binds to human MEFLIN protein. In a certain aspect of the present invention, the antibody that binds to the MEFLIN protein specifically binds to human MEFLIN protein. The term "specifically bind" means binding to the MEFLIN protein with stronger affinity than to at least another protein. The term "specifically bind" includes binding to the human MEFLIN protein with stronger affinity than to mouse MEFLIN protein.

Whether or not antibodies compete with each other can be confirmed by in-vitro competitive assay. In the competitive assay, the antibodies can be regarded as antibodies competing with each other for binding to the same antigen when the binding of the desired antibody can be blocked by, for example, at least 20%, preferably at least 20 to 50%, more preferably at least 50%. The competitive antibody can be confirmed by cross-blocking assay, preferably competitive ELISA assay. In the cross-blocking assay, for example, a microtiter plate is coated with the antigen, and a candidate competitive antibody is added thereto. The plate is incubated to form the binding between the antigen and the candidate antibody. Then, the desired antibody is labeled and then added to wells, and the plate is incubated and washed. The amount of the desired antibody bound can be quantified to determine the presence or absence of the competition between the antibodies. In the presence of competition, the amount of the label remaining in the wells should be decreased.

Whether or not antibodies bind to overlapping epitopes on the binding partner protein can be confirmed depending on whether or not their interaction faces overlap with each other. For example, hydrogen/deuterium exchange mass spectrometry (HDX-MS) is known as a method for determining epitopes. In the HDX-MS, the exchange of hydrogen of an amide proton of a protein complex for deuterium can be detected in the presence of deuterated water. In the presence of deuterated water, the amide proton on the interaction face of the protein complex is difficult to exchange for deuterium (or the rate of exchange is slow), while the amide proton of a region exposed to the surface is easily exchanged for deuterium (or the rate of exchange is fast). Thus, through the use of this phenomenon, a region found to have decrease in the rate of exchange of hydrogen for deuterium can be considered as a region bound to an antibody. The interaction face (epitope region) on the binding partner can thereby be determined for the antibody. The respective epitope regions for two antibodies can be determined by the method for determining whether or not the epitope regions overlap with each other. The exchange of hydrogen for deuterium can be detected by those skilled in the art using mass spectrometry.

In a certain aspect of the present invention, the antibody that binds to the MEFLIN protein is an antibody having internalization activity into cells. In a certain aspect of the present invention, the antibody that binds to the MEFLIN protein is an antibody having no internalization activity into cells. In a certain aspect of the present invention, cancer cells are MEFLIN protein-positive, and the antibody that binds to the MEFLIN protein is an antibody having internalization activity into cells. In a certain aspect of the present invention, cancer cells are MEFLIN protein-positive, and the antibody that binds to the MEFLIN protein is an antibody having no internalization activity into cells. In a certain aspect of the present invention, stromal cells of a cancer are MEFLIN protein-positive, and the antibody that binds to the MEFLIN protein is an antibody having internalization activity into cells. In a certain aspect of the present invention, stromal cells of a cancer are MEFLIN protein-positive, and the antibody that binds to the MEFLIN protein is an antibody having no internalization activity into cells. In these aspects, the ADC may have a cleavable linker. In these aspects, the ADC may have a non-cleavable linker. In the case of preparing a prodrug such that the payload of the ADC exerts cytotoxicity only after linker cleavage, the linker is preferably a cleavable linker. In a certain aspect, the ADC of the present invention has internalization activity and has a cleavable linker that is intracellularly cleaved. In a certain aspect, the ADC of the present invention has no internalization activity and has a cleavable linker that is extracellularly cleaved.

Whether or not an antibody has internalization activity can be confirmed by an in-vitro test. For example, the antibody that binds to the MEFLIN protein is contacted with cells having the MEFLIN protein on the cell surface and incubated for a time sufficient (e.g., approximately 15 minutes) for the internalization of the antibody. Then, an antibody in a culture solution and an antibody bound to the cell surface are washed off (e.g., using an aqueous solution containing 0.5 M NaCl and 3% by volume of acetic acid). Then, the antibody internalized into the cell can be confirmed by staining. The staining of the antibody internalized into the cell can be carried out in the same manner as in the staining of intracellular proteins. The staining of the antibody internalized into the cell can be detected, for example, on the basis of a label using a labeled secondary antibody.

Cancer tissues contain cancer cells (i.e., malignant tumor cells) and stromal cells of the cancer. MEFLIN is expressed in both malignant tumor (sarcoma) and benign tumor derived from mesenchymal stem cells or cells similar thereto. Specifically, this protein was confirmed to be expressed on cancer cells in almost all non-epithelial tumor cases such as osteosarcoma, chondrosarcoma, liposarcoma, rhabdomyosarcoma, undifferentiated pleomorphic sarcoma, desmoid tumor, and meningioma. Thus, the ADC of the present invention can be used in the treatment of malignant tumor (sarcoma) derived from mesenchymal stem cells or cells similar thereto. The ADC of the present invention can also be used in the treatment of benign tumor. In cancers (carcinoma) developed from epithelial cells, the MEFLIN protein was expressed in stromal cells (e.g., CAF) of almost all the cancers even when cancer cells themselves are MEFLIN protein-negative. Thus, the ADC of the present invention can be used in the treatment of carcinoma by targeting stromal cells of the carcinoma. The expression of MEFLIN can be examined by, for example, in situ hybridization or by immunohistochemical staining using an antibody and may be examined by other methods, for example, RT-PCR, Western blot, DNA microarray method, and RNA sequencing analysis method.

Examples of the cancer to be subjected to therapy with the ADC or the pharmaceutical composition of the present invention include, but are not particularly limited to, cancers, for example, cancers (carcinoma) developed from epithelial cells, such as lung cancer, pancreatic cancer, head and neck cancer, prostate cancer, bladder cancer, breast cancer, esophageal cancer, stomach cancer, colorectal cancer, uterine cancer, ovary cancer, skin cancer, thyroid gland cancer, thymic cancer, kidney cancer, testis cancer, penis cancer, liver cancer, bile duct cancer, and biliary tract cancer, and their metastatic cancers (or cancer cells). Examples of the cancer to be subjected to therapy with the ADC or the pharmaceutical composition of the present invention also include retroperitoneal tumor, angiosarcoma, and lymphangiosarcoma, and their metastatic cancers (or cancer cells). Further examples of the cancer to be subjected to therapy with the ADC or the pharmaceutical composition of the present invention include brain tumor and bone and soft tissue tumor. Cancer cells of these cancers are MEFLIN protein-positive, or the stroma of the cancers contains MEFLIN protein-positive cells even if the cancer cells are MEFLIN protein-negative. According to the present invention, MEFLIN protein-positive cells are recruited into the stroma of the above-mentioned cancers. Thus, according to the present invention, the cancer (or cancer cells) to be subjected to therapy with the ADC or the pharmaceutical composition of the present invention may be MEFLIN-negative. MEFLIN protein-positive cells are recruited into the stroma of a MEFLIN protein-negative cancer, and the ADC of the present invention targets the MEFLIN protein-positive cells recruited into the stroma and is capable of exerting antitumor activity against the cancer, irrespective of the cancer (or cancer cells) itself being MEFLIN protein-positive or -negative. This can be explained by a bystander effect. The presence or absence of MEFLIN protein-positive cells in the stroma of a cancer may be confirmed by testing the expression of the MEFLIN protein in a tissue specimen. In a certain aspect of the present invention, the cancer to be subjected to the therapy is MEFLIN protein-negative and is a cancer in which MEFLIN protein-positive cells reside in the stroma of the cancer. According to the present invention, the cancer to be subjected to therapy with the ADC or the pharmaceutical composition of the present invention may be a MEFLIN protein-positive cancer (e.g., sarcoma, for example, myxofibrosarcoma, malignant fibrous histiocytoma, liposarcoma, leiomyosarcoma, rhabdomyosarcoma, malignant peripheral nerve sheath tumor, Ewing's sarcoma, epithelioid sarcoma, clear cell sarcoma, synovial sarcoma, and osteosarcoma). In a certain aspect of the present invention, the cancer to be subjected to the therapy is MEFLIN protein-positive and is a cancer in which MEFLIN protein-positive cells reside in the stroma of the cancer. In a certain aspect of the present invention, the cancer to be subjected to the therapy is MEFLIN protein-positive and is a cancer in which no MEFLIN protein-positive cell is detected in the stroma of the cancer. In a certain aspect, the cancer to be subjected to the therapy can be a cancer evaluated or predicted to be MEFLIN-positive, or a cancer evaluated or predicted to contain MEFLIN-positive cells in the stroma though the cancer cells themselves are MEFLIN-negative.

The bispecific antibody can be, for example, an antibody having binding affinity for each of a cancer cell and an immunocyte. The bispecific antibody can be, for example, an antibody that binds to the MEFLIN protein and a T cell surface antigen such as CD3 protein. The bispecific antibody can be of IgG type and of diabody type. This aspect can be effective for, for example, MEFLIN protein-positive cancer cells.

In a certain aspect of the present invention, the pharmaceutical composition comprises the ADC of the present invention and an excipient. The pharmaceutical composition of the present invention can be administered by an administration method such as intravenous administration, subcutaneous administration, intratumoral administration, intraperitoneal administration, intracerebroventricular administration, or intramuscular administration. The dose can be appropriately determined by a physician in consideration of the age, sex, body weight, disease severity, etc. of a patient.

The present invention provides use of the ADC of the present invention in the production of a medicament for use in therapy of a cancer.

The present invention provides a method for therapy of a cancer in a subject in need thereof, the method comprising administering a therapeutically effective amount of the ADC of the present invention to the subject. In this aspect, the cancer to be subjected to the therapy is MEFLIN protein-negative and can be a cancer (e.g., carcinoma) in which MEFLIN protein-positive cells reside in the stroma of the cancer. In a certain aspect, the cancer can be a MEFLIN protein-positive cancer (e.g., sarcoma). Such a subject can be identified or selected by the detection of MEFLIN mRNA by immunohistochemical staining using an anti-MEFLIN antibody or by in situ hybridization in a tissue specimen obtained from the subject or a tissue section thereof.

The present invention provides use of the ADC of the present invention in a method for therapy of a cancer. The present invention can provide the ADC of the present invention for use in a method for therapy of a cancer.

EXAMPLES

Example 1: Preparation of Antibody and Characterization of Obtained Monoclonal Antibody In this Example, a monoclonal antibody that recognizes the human MEFLIN protein was prepared, and the binding characteristics of the antibody were confirmed by various assays.

[Preparation of Cell]

A human embryonic kidney (HEK293) cell line stably expressing mouse Meflin (hereinafter, referred to as a mMeflin HEK293 cell line) and a Chinese hamster ovary (CHO) cell line stably expressing mouse Meflin (hereinafter, referred to as a "mMeflin CHO cell line") were established using Flp-In™ system (Thermo Fisher Scientific, Inc.). Likewise, a human embryonic kidney (HEK293) cell line stably expressing human MEFLIN (hereinafter, referred to as a hMeflin HEK293 cell line) and a Chinese hamster ovary (CHO) cell line stably expressing human MEFLIN (hereinafter, referred to as a "hMEFLIN CHO cell line") were established.

[Preparation of Rat Anti-Human MEFLIN Monoclonal Antibody]

In animal immunization for preparing an antibody against human MEFLIN, a human MEFLIN recombinant protein was used as an antigen. The human MEFLIN recombinant protein was obtained using a mammalian cell expression system. For example, the human MEFLIN gene was introduced into a human embryonic kidney-derived cell line (Expi293F cells, Thermo Fisher Scientific, Inc.) acclimatized in suspension culture by lipofection (lipofectamine 2000, Invitrogen Corp.). In order to enable later purification, the carboxyl-terminal GPI anchor sequence of the MEFLIN gene was removed, and a histidine tag was introduced thereto. The cell culture solution 5 to 8 days after gene introduction was recovered, treated through a filter (0.22 micrometers), and then applied to a column filled with a support (Ni Excel, GE Healthcare Japan Corp.) that specifically bind to a histidine-tagged protein so that the MEFLIN protein in the culture solution was attached thereto. After washing of the column, the attached MEFLIN protein was competitively eluted using a buffer solution containing imidazole (500 mM). Imidazole was removed from the eluate containing the MEFLIN protein by ultrafiltration (dialysis using a phosphate buffer solution) to obtain a final human MEFLIN recombinant protein. The purity of the purified human MEFLIN recombinant protein was measured by subjecting the protein to SDS-PAGE electrophoresis and subsequent Coomassie Brilliant Blue staining method.

The sole of a WKY rat hindlimb was immunized once with 100 μg of the recombinant human MEFLIN protein (degree of purification: 95%). Two weeks later, plasma cells residing in iliac lymph nodes were electrically fused with a myeloma (SP2/0) cell line to prepare hybridomas. The culture medium used was HAT medium (MPB) and BM condimed H1 (Roche) supplemented with High glucose DMEM (Nacalai Tesque, Inc.), and the hybridomas were screened.

[Preparation of Mouse Anti-Human MEFLIN Monoclonal Antibody]

A monoclonal antibody was prepared in the same manner as in the preparation of the rat anti-human MEFLIN monoclonal antibody except that the muscle of a C57BL/6 mouse tail root was immunized once with 50 μg of the recombinant human MEFLIN protein (degree of purification: 95%).

[Screening of Hybridoma]

A hybridoma producing the monoclonal antibody that recognizes the antigen was screened for by each method of ELISA using the recombinant human MEFLIN protein, immunofluorescence staining (IF) using the hMEFLIN CHO cell line, flow cytometry using the hMEFLIN CHO cell line, and immunoprecipitation and Western blotting using a cell lysate prepared from the hMeflin HEK293 cell line.

[Western Blotting]

The human embryonic kidney (HEK293) cell line was allowed to transiently express pRP-CMV vector having an insert of DNA encoding the human MEFLIN protein or a fragment thereof by lipofection, and a cell lysate was prepared. The fragment used was the fragments shown in FIG. 1 or 2 and had a C-terminal G196 tag and His tag. SDS-PAGE was performed using the cell lysate, and the electrophoresed protein was transferred to a PVDF membrane. The PVDF membrane was reacted at ordinary temperature for 1 hour using 5% skimmed milk/PBS. The primary antibody used was a culture supernatant of each hybridoma clone diluted 50-fold with PBS. For a positive subject, an anti-G196 antibody was used as a primary antibody. The PVDF membrane was reacted overnight at 4° C. in the presence of the primary antibody. Then, the PVDF membrane was washed with 0.05% Tween/PBS. The secondary antibody used was an anti-rat or anti-mouse antibody-horseradish peroxidase (HRP) conjugate. The secondary antibody was diluted 1000-fold with PBS and reacted with the PVDF membrane at ordinary temperature for 45 minutes. After washing with 0.05% Tween/PBS, the HRP label on the antibody was allowed to emit light using ECL (GE Healthcare Japan Corp.), and an image was captured into a computer using a CCD imager (Las 4000, GE Healthcare Japan Corp.).

[Analysis of Internalization Activity of Monoclonal Antibody]

The hMeflin CHO cell line or the mMeflin CHO cell line was cultured at 37° C. for 3 hours under 5% $CO_2$ in an assay solution of F-12 Glutamax culture medium (Gibco) supplemented with 20 mM HEPS and 0.1% BSA. Each hybridoma supernatant was diluted 10-fold with the assay solution and added to the CHO cell line, followed by culture for 15 minutes. The CHO cell line was washed with PBS (4° C.), and an antibody bound on the cell membrane was washed off with a washing solution (MilliQ-$H_2O$ containing 0.5 M NaCl and 3% acetic acid). The CHO cell line was fixed in 4% paraformaldehyde (PFA) through reaction for 10 minutes and then reacted with 0.1% Triton X-100 for 5 minutes for cell membrane permeation treatment. The secondary antibody used was an anti-rat or anti-mouse antibody-Alexa 488 conjugate. The secondary antibody was diluted 400-fold with PBS and reacted with the cells treated by cell membrane permeation at ordinary temperature for 30 minutes. After washing with PBS, the cells were reacted with DAPI at ordinary temperature for 5 minutes and washed with PBS, and an image was obtained using a confocal microscope (LSM700, Carl Zeiss AG).

[In Situ Hybridization]

A region richest in tumor components was microscopically selected from a pathological tissue preparation obtained from a sarcoma patient or a carcinoma patient, and examined for the expression of MEFLIN (also referred to as "ISLR") by in situ hybridization (hereinafter, referred to as the "ISH staining method") (see WO2017/22472). Among the examined tissues, which were observed in a field of view with a medium magnification (20× objective lens), sarcoma tissues were grouped into ISLR-positive tumor tissues when 20% or more of cells having the morphology of tumor cells were ISLR-positive and into ISLR-negative tumor tissues when the percentage of the cells was less than this. Likewise, carcinoma tissues were grouped into ISLR-positive tumor tissues when 20% or more of cells infiltrating into the cancer stroma and having fibroblast-like morphology were ISLR-positive and into ISLR-negative tumor tissues when the percentage of the cells was less than this. Tissues were regarded as being ISLR-positive when signals were observed in at least a portion of the cytoplasm.

[Histological Immunofluorescence Double Staining Method]

Tumor tissues were sampled from cancer-bearing mouse models in which an osteosarcoma cell line (HsOs1) or a pancreatic cancer cell line (BxPC-3) was subcutaneously transplanted. The tissue samples were fixed in 10% formalin and then embedded in paraffin. The samples were sliced into a thickness of 2 μm, and the paraffin-embedded tissues were left standing on glass slides and deparaffinized with xylene and ethanol, followed by the activation of the antigen with an antigen activation solution of pH 6.0 (Leica Camera AG). After subsequent blocking, the immunofluorescence double staining method was performed using an anti-MEFLIN monoclonal antibody and an anti-cathepsin K antibody (ab37259, Abcam plc) as primary antibodies and an anti-rat antibody-Alexa 488 conjugate and an anti-mouse antibody-Alexa 594 conjugate as secondary antibodies (Invitrogen Corp.). The intracellular nuclei were stained with DAPI. The colors were green for MEFLIN, red for cathepsin K, and blue for the nuclei. An image was obtained using a confocal microscope (LSM700, Carl Zeiss AG).

[Immunohistochemical Staining Method]

A region richest in tumor components was microscopically selected from a pathological tissue preparation obtained from a carcinoma patient, and examined for the expression of MEFLIN (also referred to as "ISLR") by the immunohistochemical staining method (hereinafter, referred to as the "IHC staining method"). The examined tissues, which were observed in a field of view with a medium magnification (20× objective lens), were grouped into ISLR-positive tumor tissues when 20% or more of cells infiltrating into the cancer stroma and having fibroblast-like morphology were ISLR-positive and into ISLR-negative tumor tissues when the percentage of the cells was less than this. Tissues were regarded as being ISLR-positive when signals were observed in at least a portion of the cytoplasm. An anti-rat or anti-mouse antibody-horseradish peroxidase (HRP) conjugate was used as a secondary antibody (ImmPRESS, Vector Laboratories).

[Results]

Figures 2, 3:
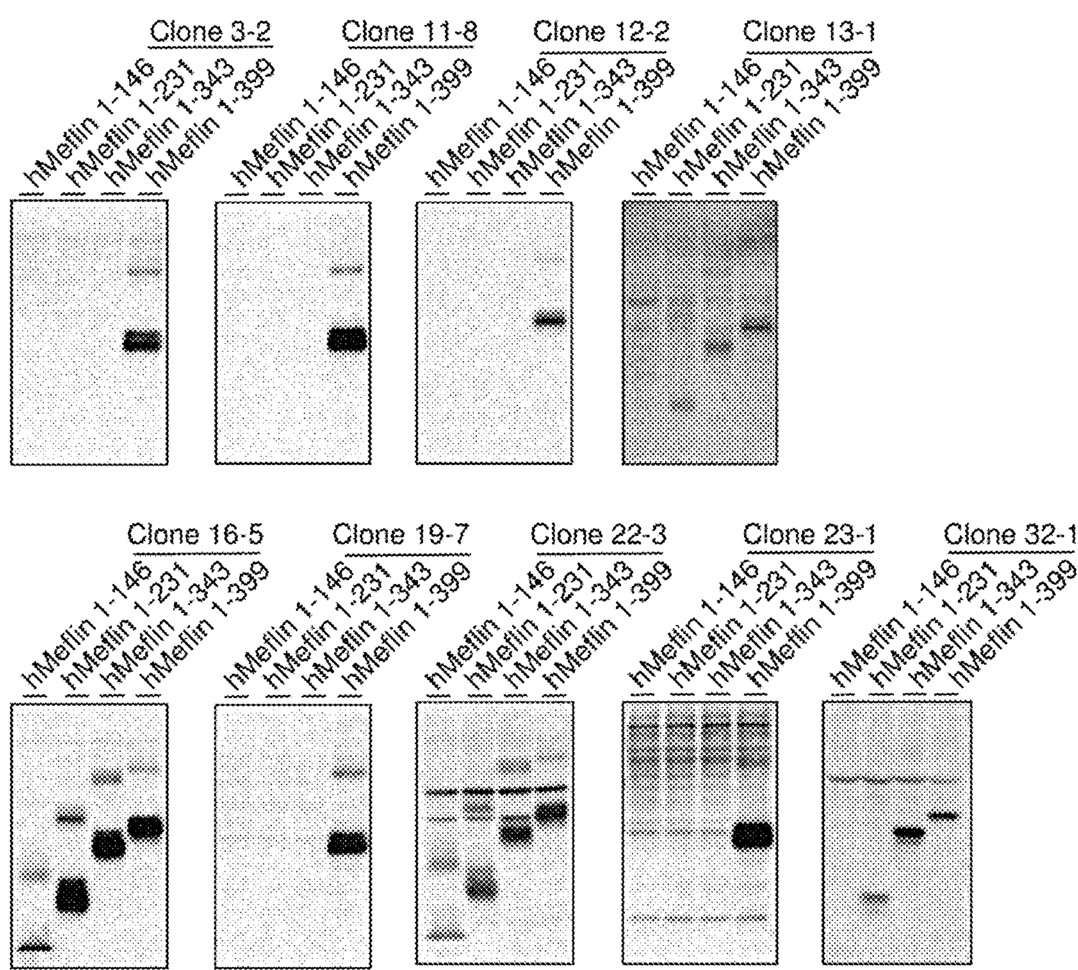
FIG. 2 shows results of Western blotting showing the binding property of a monoclonal antibody obtained from each clone against human MEFLIN protein.
FIG. 3 shows a fluorescence microscope image showing the intracellular uptake (internalization) activity of a monoclonal antibody obtained from each clone into cells. The cell nuclei were stained with DAPI, and the antibody was detected with an Alexa 488-labeled antibody.

Results of examining the binding of each monoclonal antibody to each human MEFLIN protein fragment by Western blotting was as shown in FIG. 1. As shown in FIG. 1, a rat- or mouse-derived monoclonal antibody produced from clone 27-7 (hereinafter, simply referred to as the "27-7 antibody") bound to an amino acid region from positions 1 to 399 of human MEFLIN without binding to an amino acid region from positions 1 to 343. This suggested that the 27-7 antibody binds to an amino acid region from positions 344 to 399 of human MEFLIN. Likewise, FIG. 1 suggested that: the 34-4 antibody binds to an amino acid region from positions 232 to 343; the 35-9 antibody binds to an amino acid region from positions 1 to 146; and the 27-8 antibody, the 41-10 antibody, and the 46-3 antibody bind to an amino acid region from positions 344 to 399 of human MEFLIN. As shown in FIG. 2, it was suggested that: the 3-2 antibody, the 11-8 antibody, the 12-2 antibody, the 19-7 antibody, and the 23-1 antibody bind to an amino acid region from positions 344 to 399 of human MEFLIN; the 13-1 antibody binds to an amino acid region from positions 147 to 231; and the 16-5 antibody, the 22-3 antibody, and the 32-1 antibody bind to an amino acid region from positions 1 to 146.

Figure 4:
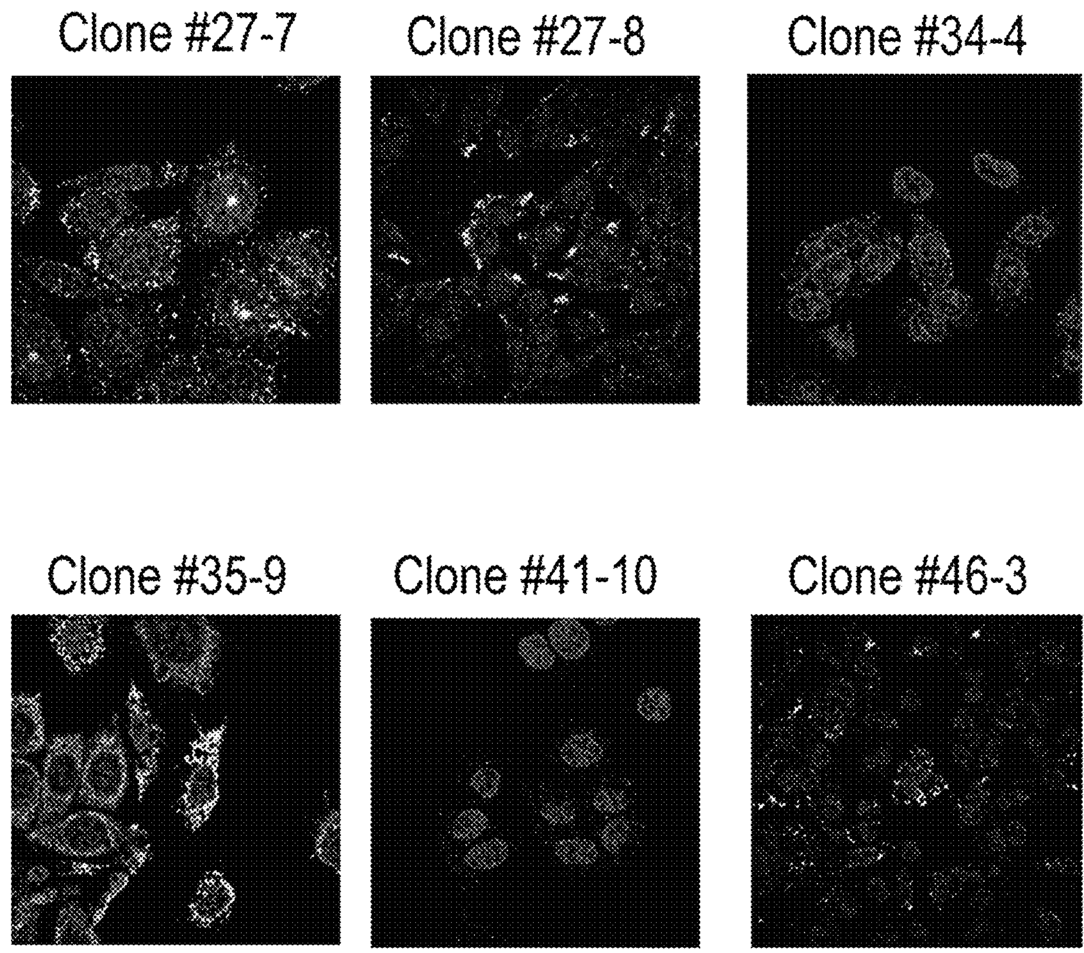
FIG. 4 shows a fluorescence microscope image showing the intracellular uptake (internalization) activity of a monoclonal antibody obtained from each clone into cells. The cell nuclei were stained with DAPI, and the antibody was detected with an Alexa 488-labeled antibody.
Figure 5:
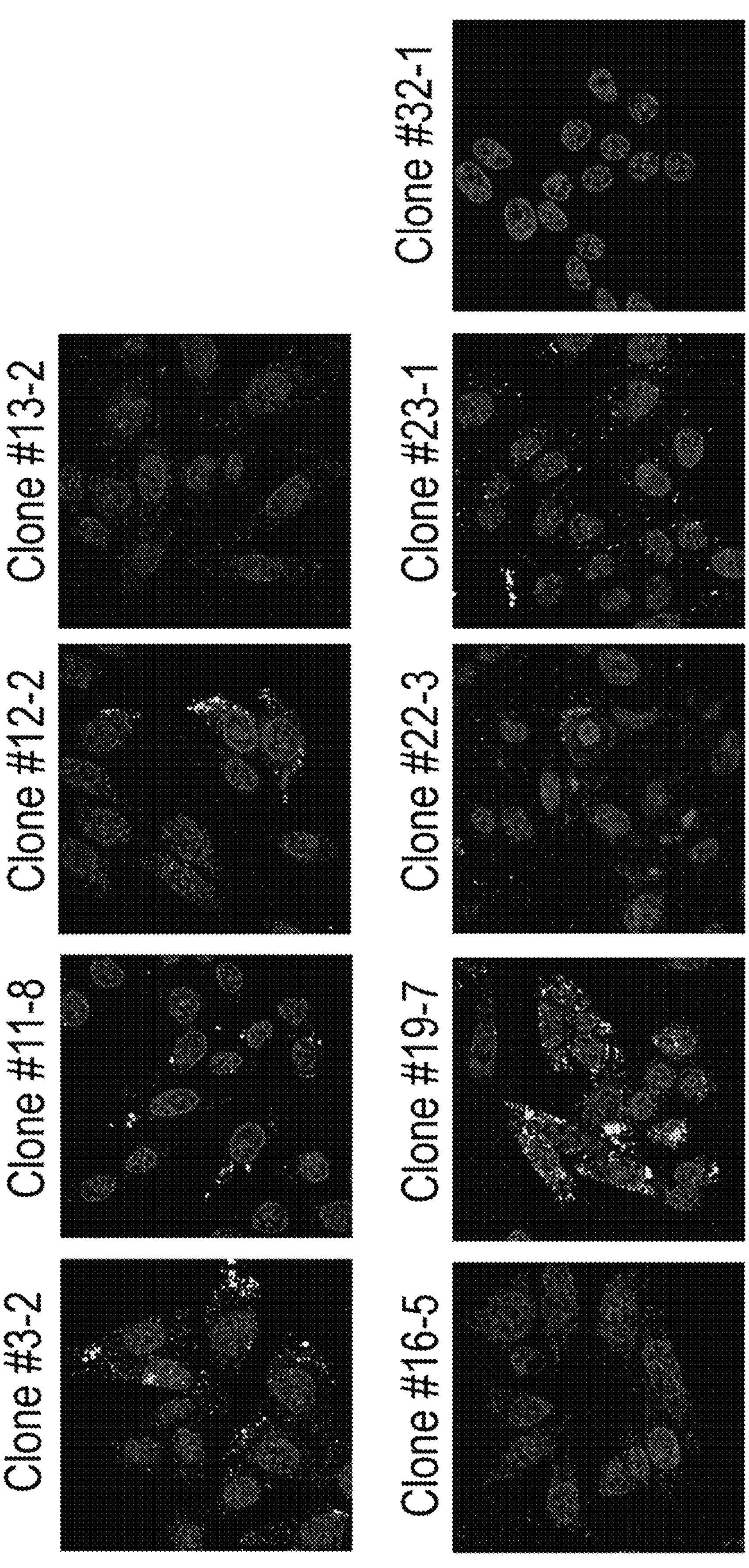
FIG. 5 shows a fluorescence microscope image showing the intracellular uptake (internalization) activity of a monoclonal antibody obtained from each clone into cells. The cell nuclei were stained with DAPI, and the antibody was detected with an Alexa 488-labeled antibody.

The internalization activity of each antibody clone was confirmed. The results were as shown in FIGS. 3 to 5. As shown in FIGS. 3 to 5, strong intracellular signals derived from the antibody were observed for the 21-3 antibody, the 25-1 antibody, the 8-2 antibody, the 27-7 antibody, the 27-8 antibody, the 34-4 antibody, the 35-9 antibody, the 46-3 antibody, the 3-2 antibody, the 11-8 antibody, the 12-2 antibody, the 16-5 antibody, the 19-7 antibody, the 22-3 antibody, the 23-1 antibody and the 32-1 antibody.

The results were as shown in Table 9.

TABLE 9

List of characteristics of each monoclonal antibody

| Clone name | Host | Internalization | Epitope |
|---|---|---|---|
| 21-3 | Rat | S | ? |
| 25-1 | Rat | M | ? |
| 8-2 | Mouse | S | ? |
| 27-7 | Rat | S | 344-399 |
| 27-8 | Rat | S | 344-399 |
| 34-4 | Rat | M | 232-343 |
| 35-9 | Rat | S | 1-146 |
| 41-10 | Rat | N | 344-399 |
| 46-3 | Rat | S | 344-399 |
| 3-2 | Mouse | M | 344-399 |
| 11-8 | Mouse | M | 344-399 |
| 12-2 | Mouse | M | 344-399 |
| 13-1 | Mouse | N | 147-231 |
| 16-5 | Mouse | N | 1-146 |
| 19-7 | Mouse | S | 344-399 |
| 22-3 | Mouse | M | 1-146 |
| 23-1 | Mouse | M | 344-399 |
| 32-1 | Mouse | N | 1-146 |

In Table 9, the symbol "S" represents that strong internalization activity was found, the symbol "M" represents that moderate internalization activity was found, and the symbol "N" represents that no internalization activity was detected. In the table, "?" means undetermined. In Table 9, "Host" represents that the species from which the antibody was derived was a rat or a mouse. In Table 9, the 21-3 antibody, the 25-1 antibody and the 8-2 antibody bound to the mouse MEFLIN protein, and the other antibodies were antibodies that bind to the human MEFLIN protein.

The expression of the MEFLIN protein in various cancer tissues was as shown in Table 10. Table 10 shows the number of tissues samples assayed, the number of positive samples among them, and a positive ratio (%).

TABLE 10

Expression of human MEFLIN (ISLR) in tumor cells

| Tumor type | | ≥ISLR (+) 20% tumor cells | Positive % |
|---|---|---|---|
| Osteosarcoma | | 8/34 | 23.5% |
| Soft sarcoma | Rhabdomyosarcoma | 6/10 | 60.0% |
| | Desmoid sarcoma | 9/54 | 16.7% |
| | Liposarcoma | 10/44 | 22.7% |
| | Chondrosarcoma | 7/35 | 20.0% |

The expression of human MEFLIN (ISLR) in the tumor stroma was as shown in Table 11. Table 11 shows the number of tissues samples assayed, the number of positive samples among them, and a positive ratio (%). Two out of seven stomach cancer cases were positive.

TABLE 11

Expression of human MEFLIN (ISLR) in tumor stroma

| Tumor type | ≥ISLR (+) 20% stromal cells | Positive % |
|---|---|---|
| Pancreatic cancer | 47/71 | 66.2% |
| Lung cancer | 103/180 | 57.2% |
| Breast cancer | 34/71 | 47.9% |
| Colorectal cancer | 29/53 | 54.7% |
| Bile duct cancer | 20/47 | 42.6% |
| Ovary cancer | 43/48 | 89.6% |
| Bladder cancer | 18/35 | 51.4% |
| Esophageal cancer | 44/69 | 63.8% |

The tumor cells of pancreatic cancer, lung cancer, breast cancer, colorectal cancer, stomach cancer, bile duct cancer, ovary cancer, bladder cancer and esophageal cancer were negative for the expression of human MEFLIN.

Example 2: Preparation of Antibody-Drug Conjugate (ADC) and In-Vivo Drug Efficacy Test Thereof In this Example, a conjugate of each antibody prepared in Example 1 and a cytotoxic agent was prepared. The prepared conjugate was administered to cancer-bearing mouse models, and its antitumor effect was confirmed.

[Preparation of ADC]

An antibody was purified using Mono Spin™ L ProG (GL Sciences Inc.) from an antibody-containing hybridoma supernatant enriched by the high-density culture of the hybridoma. The disulfide bonds of the antibody were cleaved by reduction treatment with 1.0 mM DTT at 25° C. for 30 minutes, and VcMMAE (mc-vc-PAB-MMAE, MedChemExpress) or mc-$PEG_{12}$-vc-PABC-MMAE was added to the exposed thiol groups at ordinary temperature, followed by purification by ultrafiltration. The VcMMAE is a compound registered under CAS No. 646502-53-6. The VcMMAE is composed of monomethyl auristatin E (MMAE) attached to a valine-citrulline linker via p-aminobenzoyloxycarbonyl (PBAC) and is configured to release MMAE upon cleavage of valine-citrulline by protease such as cathepsin B. The valine-citrulline linker is modified with a maleimidocaproyl group and can be reacted with a thiol group of cysteine of an antibody via the maleimido group. The mc-$PEG_{12}$-vc-PABC-MMAE is the same as VcMMAE except that PEG is interposed. Its mechanism of MMAE release is also the same as that of VcMMAE. The drug-antibody ratio (the number of molecules of the cytotoxic agent conjugated with one molecule of the antibody; DAR) was determined by calculating the difference between the number of thiol groups of the antibody after reduction treatment and the number of thiol groups after addition of VcMMAE to the antibody. Specifically, the exposed thiol groups are reacted with 5,5'-dithiobis(2-nitrobenzoic acid, Dojindo Laboratories) to form stable 5-mercapto-2-nitrobenzoic acid. The thiol groups are quantified from the absorbance ($\lambda_{max}$=412 nm, $\varepsilon$=1.55×$10^4$) of this formed thiol.

The mc-vc-PAB-MMAE has a structure of the following formula (I):

[Formula 1]

(I)

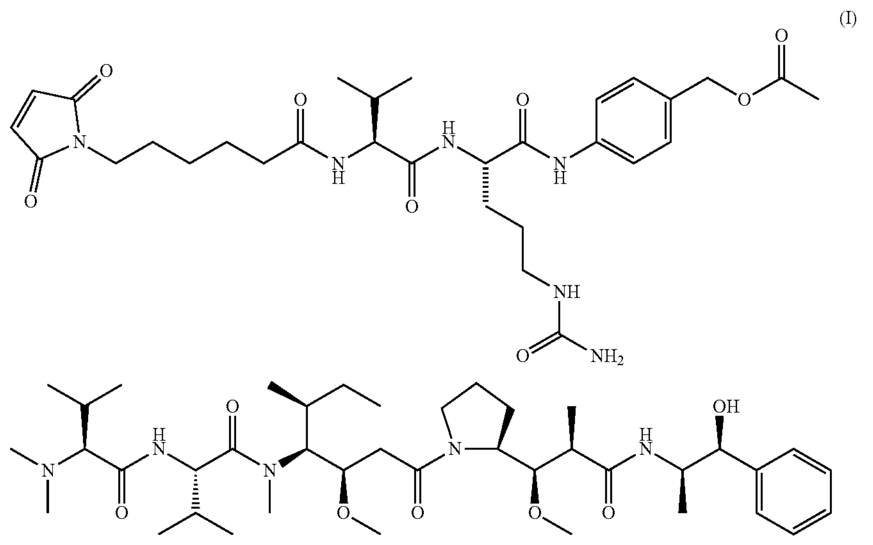

The obtained ADC can have a structure of the following formula (II):
[Formula 2]
(II)
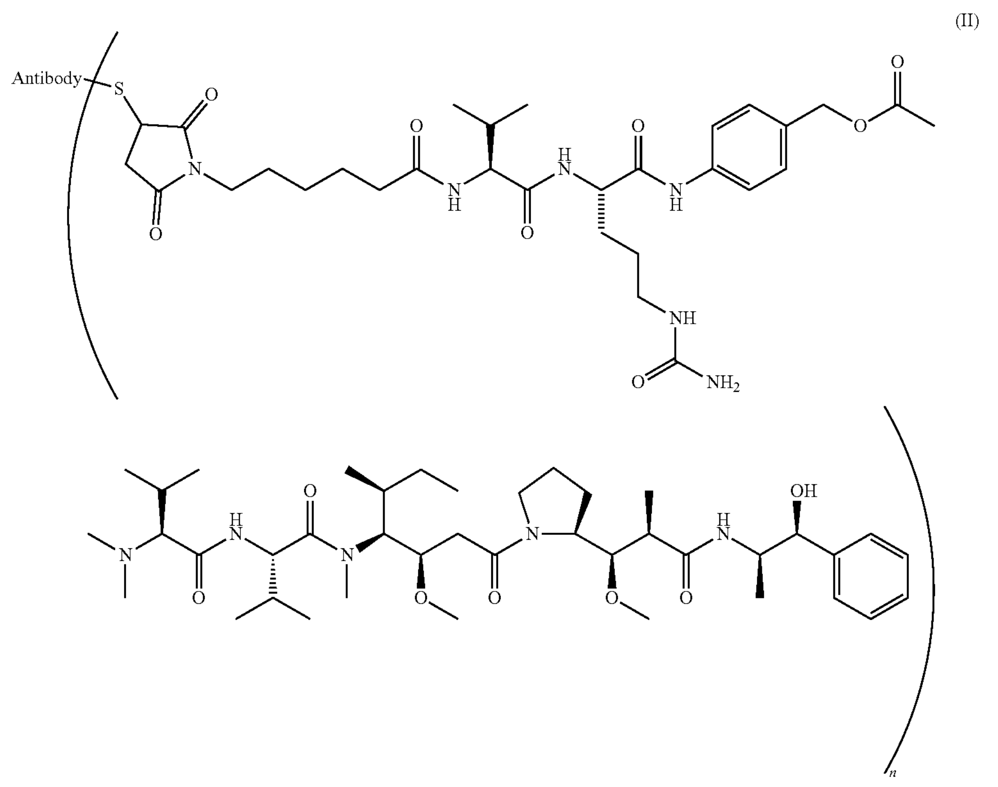
wherein n is any natural number of 1 to 8.
The mc-$PEG_{12}$-vc-PABC-MMAE has a structure of the following formula (III):
[Formula 3]
(III)
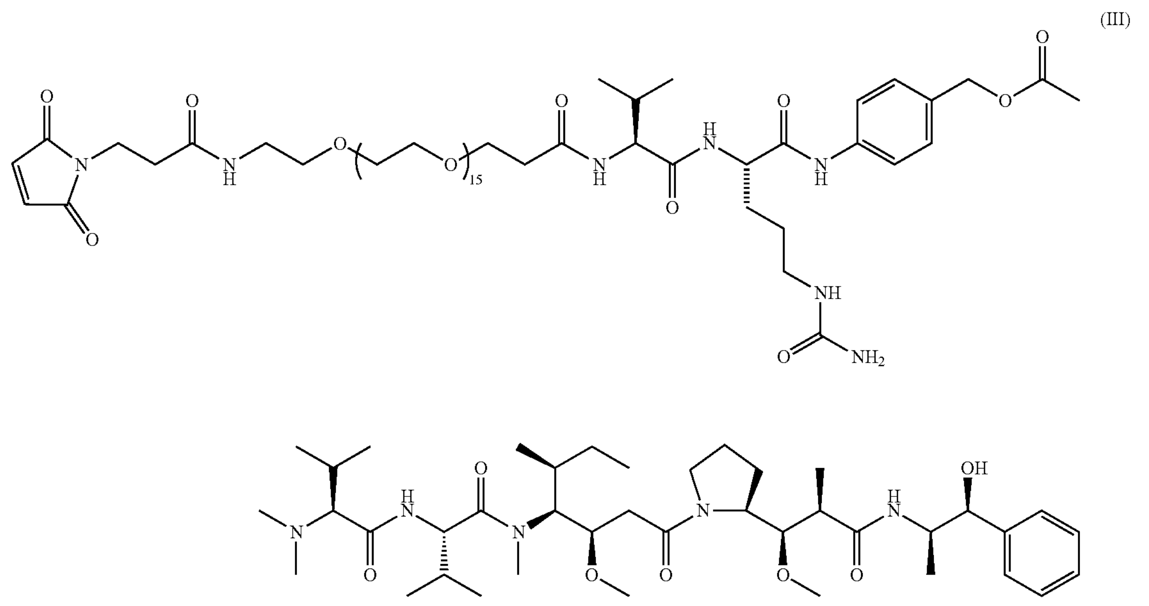

The prepared ADC was used to test cytotoxicity to various cells.

Cytotoxicity of ADC to HEK293 Cell Expressing Human MEFLIN

First, the cytotoxicity of ADC to HEK293 cells expressing human MEFLIN was tested. Specifically, the hMeflin HEK293 cell line was inoculated at $1.0\times10^4$ cells/well to a plate and cultured at 37° C. for 1 day under 5% $CO_2$. Next, each concentration of ADC was added thereto, and the cells were cultured for 2 days and evaluated for the ability of the cells to proliferate by the MTT test. The ability of the cells to proliferate was evaluated by measuring the absorbance of a sample at a wavelength of 590 nm using an absorption spectrometer (POWERSCAN 4, DS Pharma Biomedical Co., Ltd.) in the MMT test. Also, the Meflin expression level of the hMeflin HEK293 cell line was evaluated by FACS analysis. Hereinafter, a clone number simply described in a drawing means that the monoclonal antibody itself was used; a clone number described immediately before or immediately after ADC means that ADC in which the antibody was the clone was used; and CTL ADC or isotype control IgG ADC means that ADC in which the antibody was an isotype control IgG antibody was used. The isotype control antibody used was rat IgG2a (BioLegend, Inc.).

Figure 6:
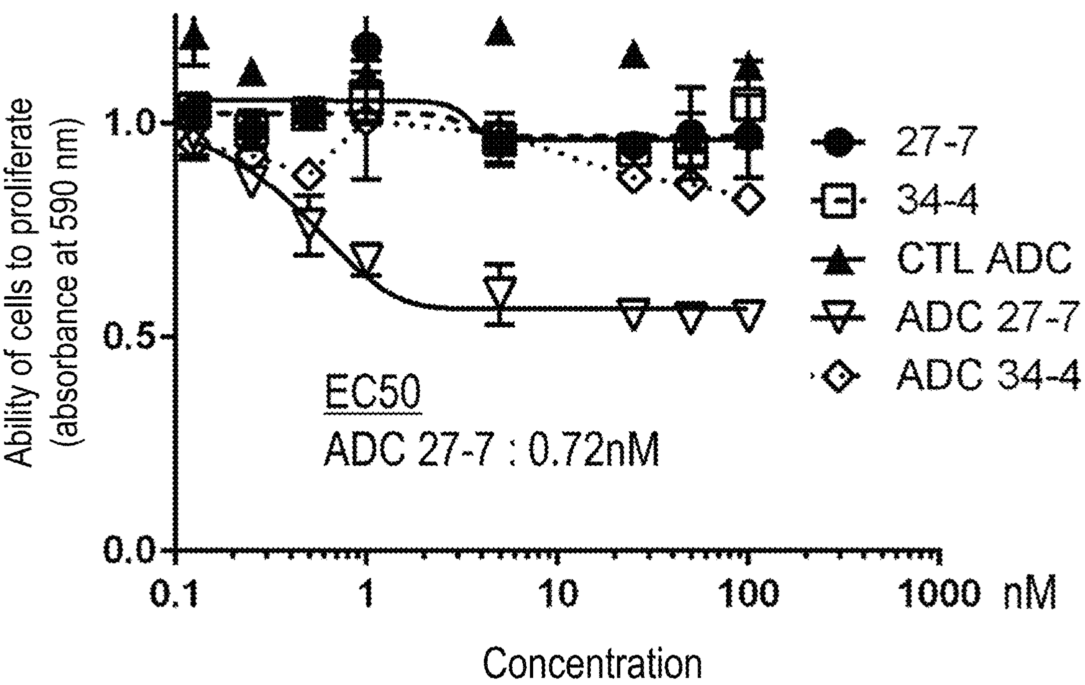
FIG. 6 shows the in-vitro cell proliferation inhibitory activity of a prepared antibody-drug conjugate (ADC) against cells (HEK293 cells) overexpressing human MEFLIN protein.
Figure 6:
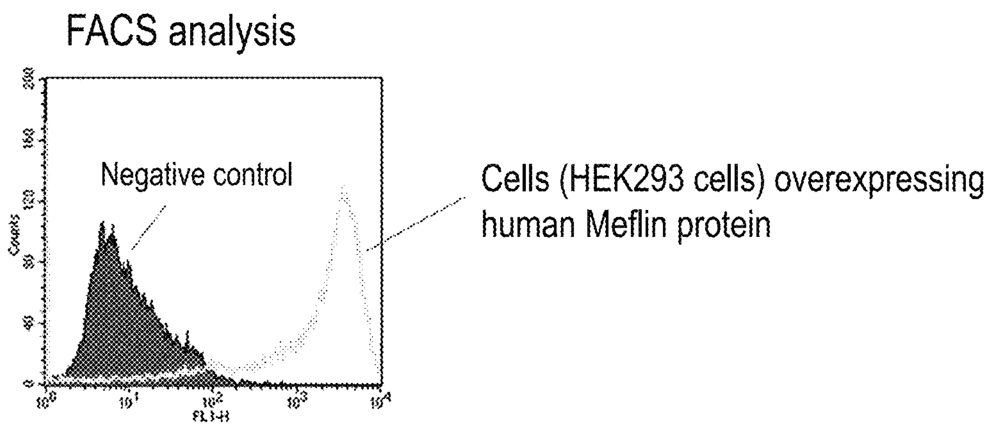

The results were as shown in FIG. 6. As shown in FIG. 6, the FACS analysis revealed that the HEK293 cells expressing human MEFLIN strongly expressed the human MEFLIN protein. ADC27-7 (drug-antibody ratio (DAR)=2.4) significantly reduced the proliferation of the HEK293 cells expressing the human MEFLIN protein. $EC_{50}$ of ADC27-7 was 0.72 nM. ADC34-4 (DAR=3.4) having moderate internalization activity against the hMEFLIN CHO cells had weak inhibitory activity against cell proliferation.

Cytotoxicity of ADC to Human Rhabdomyosarcoma Cell Line

Figure 7:
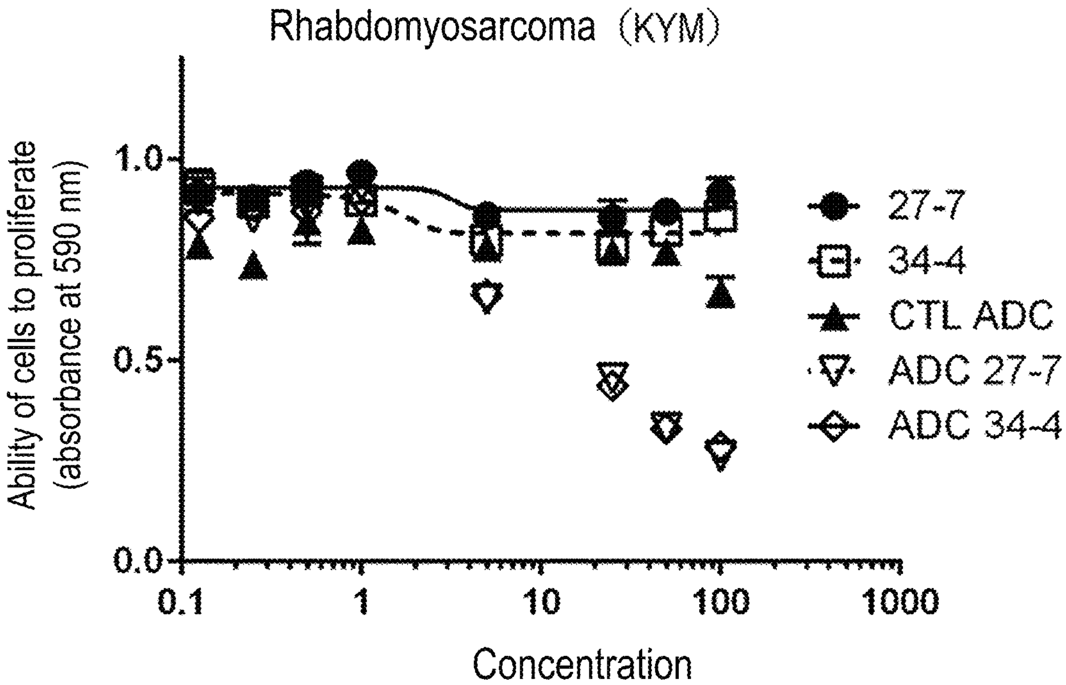
FIG. 7 shows the in-vitro cell proliferation inhibitory activity of ADC against a human rhabdomyosarcoma cell line (KYM-1 cells).
Figure 7:
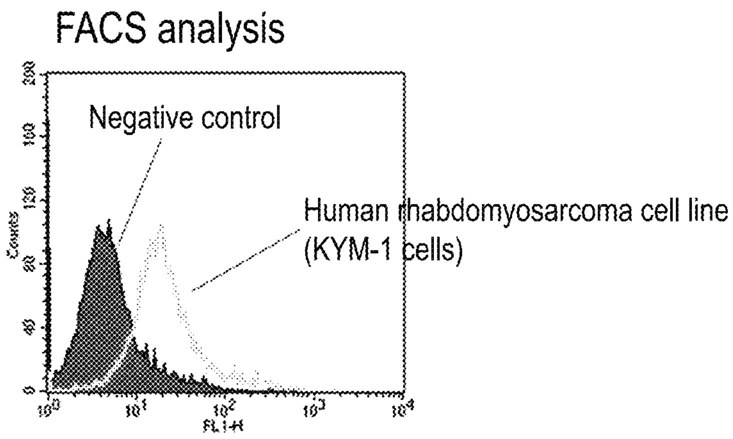

The cytotoxicity of ADC to a rhabdomyosarcoma (KYM-1) cell line was tested in the same manner as above. The results were as shown in FIG. 7. As shown in FIG. 7, the FACS analysis revealed that the rhabdomyosarcoma cell line strongly expressed the human MEFLIN protein. ADC27-7 and ADC34-4 significantly reduced the proliferation of the KYM-1 cell line.

Cytotoxicity of ADC in Model with Subcutaneously Transplanted Rhabdomyosarcoma Cell Line Next, the cytotoxicity of ADC was tested in vivo using cancer-bearing mouse models. $1.0\times10^7$ cells of a KYM-1 cell line were subcutaneously transplanted to the back of each female NOD SCID mouse (n=5 per group). ADC was intraperitoneally administered to the mouse having a tumor volume of approximately 100 $mm^3$ (5 mg/kg body weight; a total of 5 doses were administered at 4-day intervals). The length (L) and width (W) of tumor were measured using electric calipers, and the volume was calculated according to $V=L\times W^2\times0.52$. The tumor formed by the transplantation of the KYM cell line was subjected to ISH staining.

Figure 8:
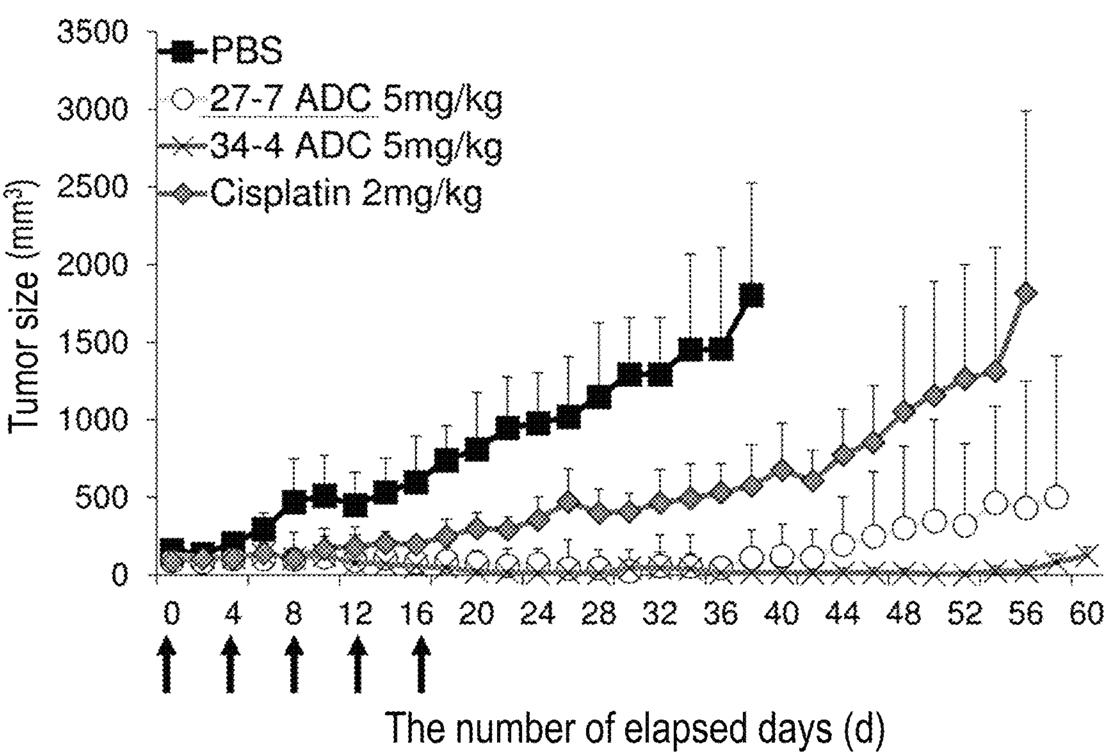
FIG. 8 shows the in-vivo antitumor effect of ADC against cancer-bearing mouse models in which a rhabdomyosarcoma cell line (KYM-1) was subcutaneously transplanted. The arrows in the graph depict the timings of administration.
Figure 8:
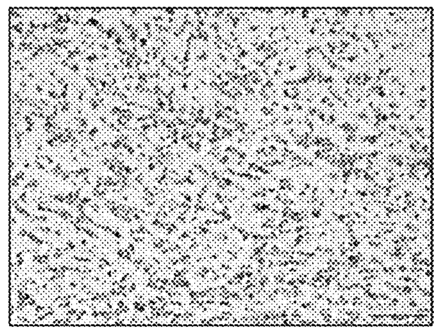

The results were as shown in FIG. 8. As shown in FIG. 8, 27-7ADC and 34-4ADC were found to exert potent antitumor activity against rhabdomyosarcoma. As is evident from the tissue image, the tumor strongly expressed human MEFLIN.

Cytotoxicity of ADC in Model with Subcutaneously Transplanted Osteosarcoma Cell Line $1.0\times10^7$ cells of an endogenous Meflin-positive osteosarcoma (HsOs1) cell line were subcutaneously transplanted to the back of each female NOD SCID mouse (n=5 per group). ADC was intraperitoneally administered to the mouse having a tumor volume of approximately 75 $mm^3$ (5 mg/kg body weight; a total of 5 doses were administered at 4-day intervals). The length (L) and width (W) of tumor were measured using electric calipers, and the volume was calculated according to $V=L\times W^2\times0.52$. The tumor formed by the transplantation of the HsOs1 cell line was subjected to ISH staining.

Figure 9:
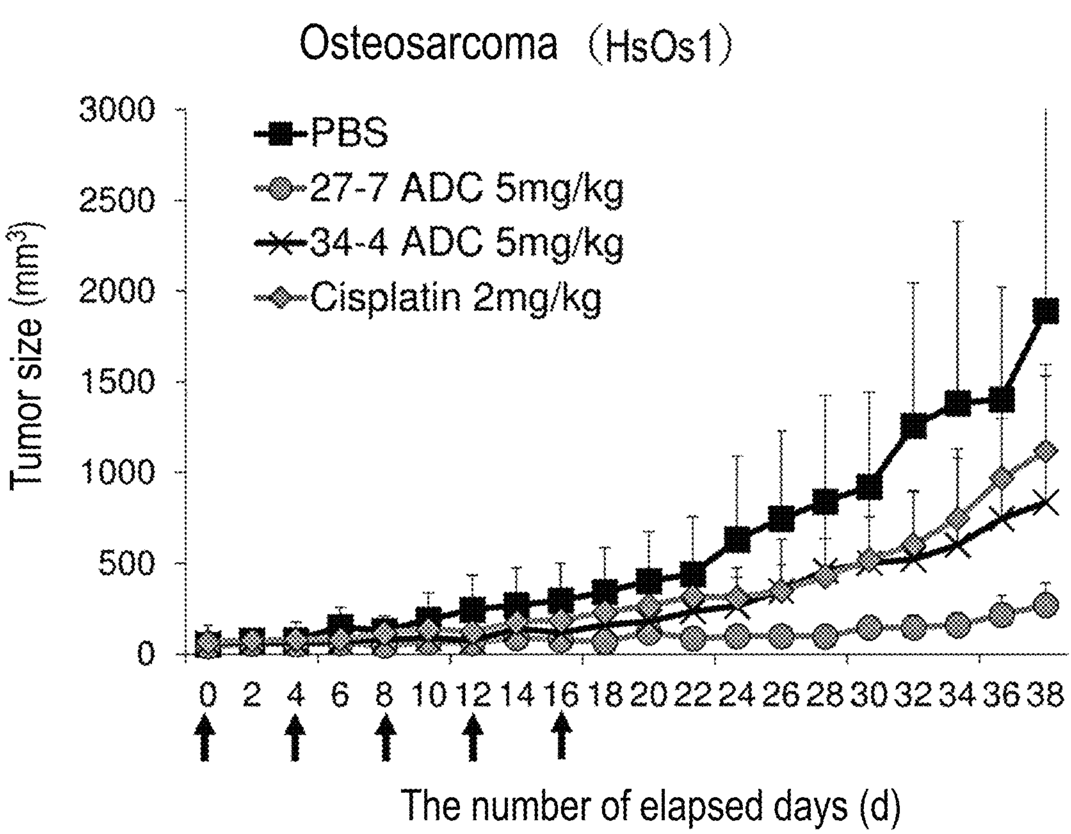
FIG. 9 shows the in-vivo antitumor effect of ADC against cancer-bearing mouse models in which an osteosarcoma cell line (HsOs1) was subcutaneously transplanted. The arrows in the graph depict the timings of administration.
Figure 9:
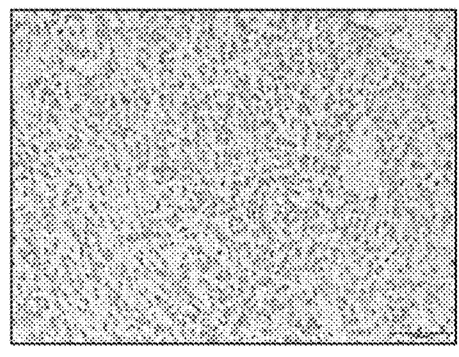

The results were as shown in FIG. 9. As shown in FIG. 9, 27-7ADC and 34-4ADC were found to exert potent antitumor activity against osteosarcoma. As is evident from the tissue image, the tumor moderately expressed human MEFLIN.

Cytotoxicity of ADC in model with subcutaneously transplanted pancreatic cancer cell line $1.0\times10^7$ cells of an endogenous Meflin-negative human pancreatic cancer (BxPC-3) cell line were subcutaneously transplanted to the back of each female nude mouse (BALB/cS1c nu/nu) (n=5 per group). ADC was intraperitoneally administered to the mouse having a tumor volume of approximately 150 $mm^3$ (5 mg/kg body weight; a total of 5 doses were administered at 4-day intervals). The length (L) and width (W) of tumor were measured using electric calipers, and the volume was calculated according to $V=L\times W^2\times0.52$. The tumor formed by the transplantation of the BxPC-3 cell line was subjected to ISH staining.

Figure 10:
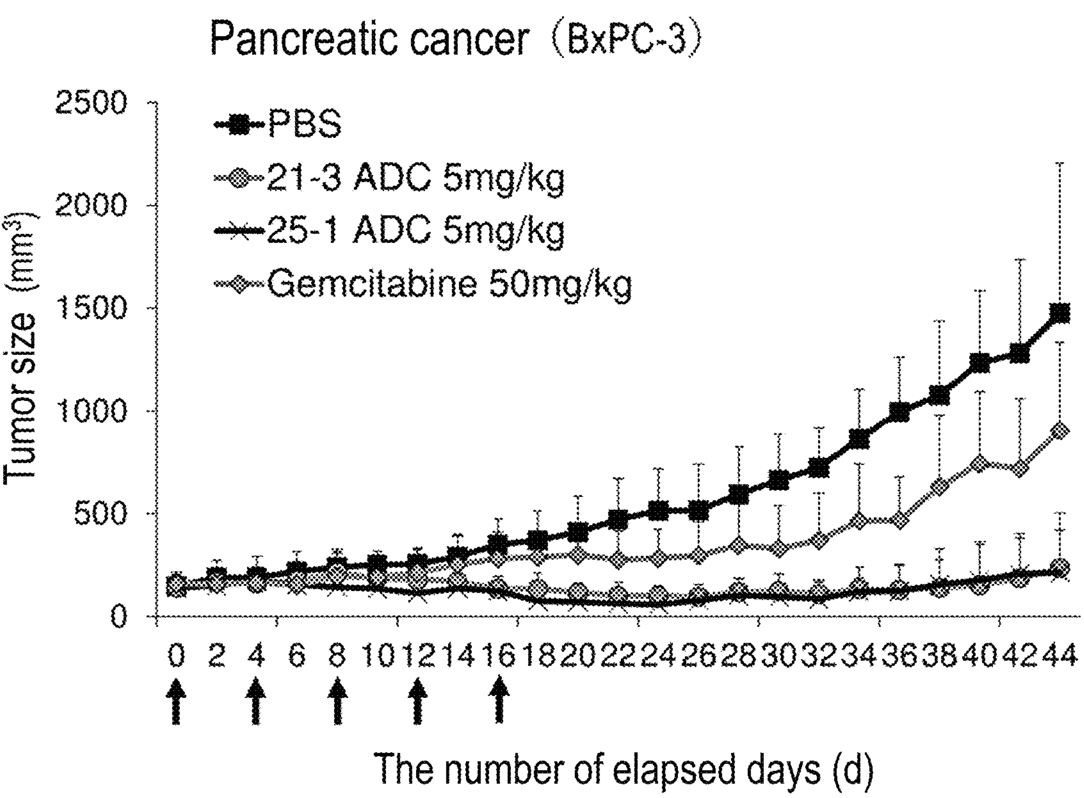
FIG. 10 shows the in-vivo antitumor effect of ADC against cancer-bearing mouse models in which a pancreatic cancer cell line (BxPC-3) was subcutaneously transplanted. The arrows in the graph depict the timings of administration.
Figure 10:
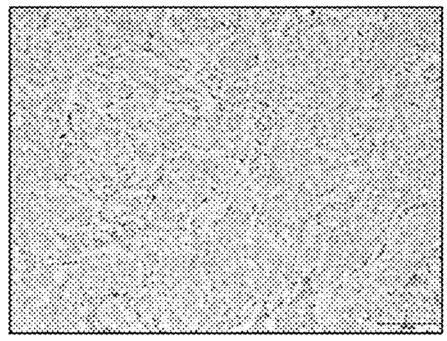

The results were as shown in FIG. 10. As shown in the tissue image of FIG. 10, mouse MEFLIN-positive cells were found in the stromal cells of the tumor though the pancreatic cancer cells themselves were MEFLIN-negative. 21-3ADC and 25-1ADC were found to exert potent antitumor activity against pancreatic cancer. The original tissues were MEFLIN-negative, demonstrating that the MEFLIN-positive cells were recruited to the vicinity of the tumor. It was also suggested that the ADC exerted antitumor activity against the tumor.

Cytotoxicity of ADC in Model with Subcutaneously Transplanted Lung Cancer Cell Line $1.0\times10^7$ cells of an endogenous Meflin-negative human lung cancer (A549) cell line were subcutaneously transplanted to the back of each female nude mouse (BALB/cS1c nu/nu) (n=5 per group). ADC was intraperitoneally administered to the mouse having a tumor volume of approximately 100 $mm^3$ (5 mg/kg body weight; a total of 5 doses were administered at 4-day intervals). The length (L) and width (W) of tumor were measured using electric calipers, and the volume was calculated according to $V=L\times W^2\times0.52$. The tumor formed by the transplantation of the A549 cell line was subjected to ISH staining.

Figure 11:
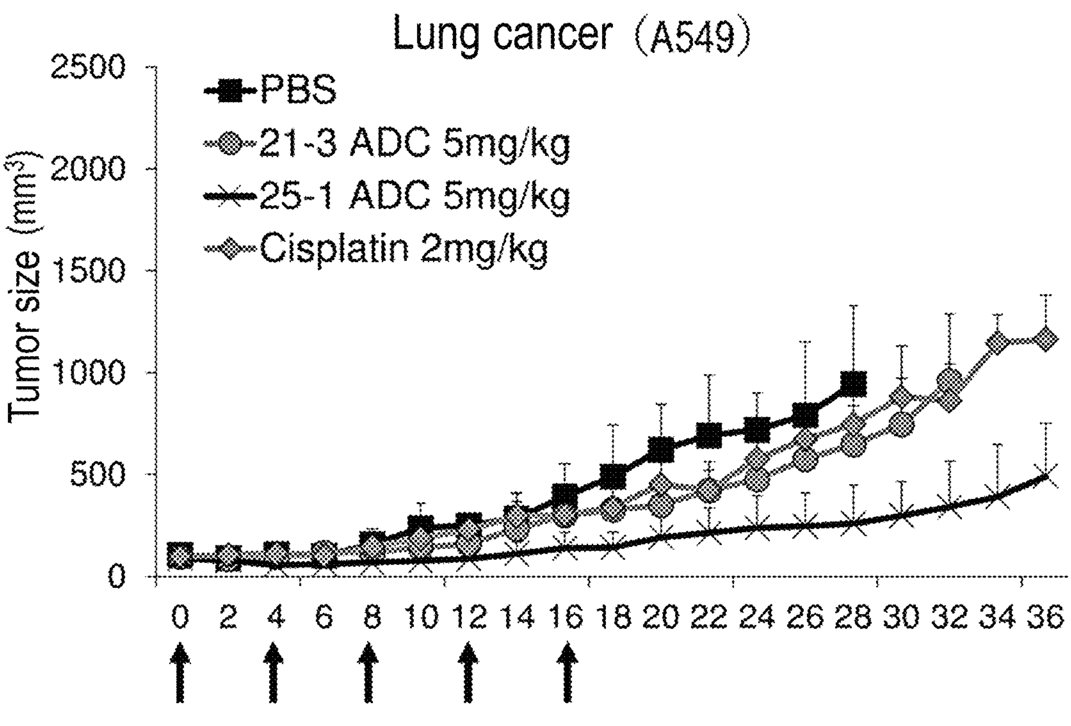
FIG. 11 shows the in-vivo antitumor effect of ADC against cancer-bearing mouse models in which a lung cancer cell line (A549) was subcutaneously transplanted. The arrows in the graph depict the timings of administration.
Figure 11:
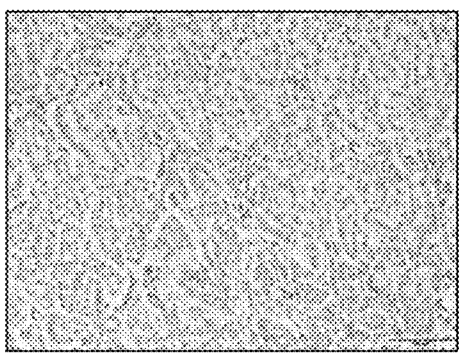
Figure 25:
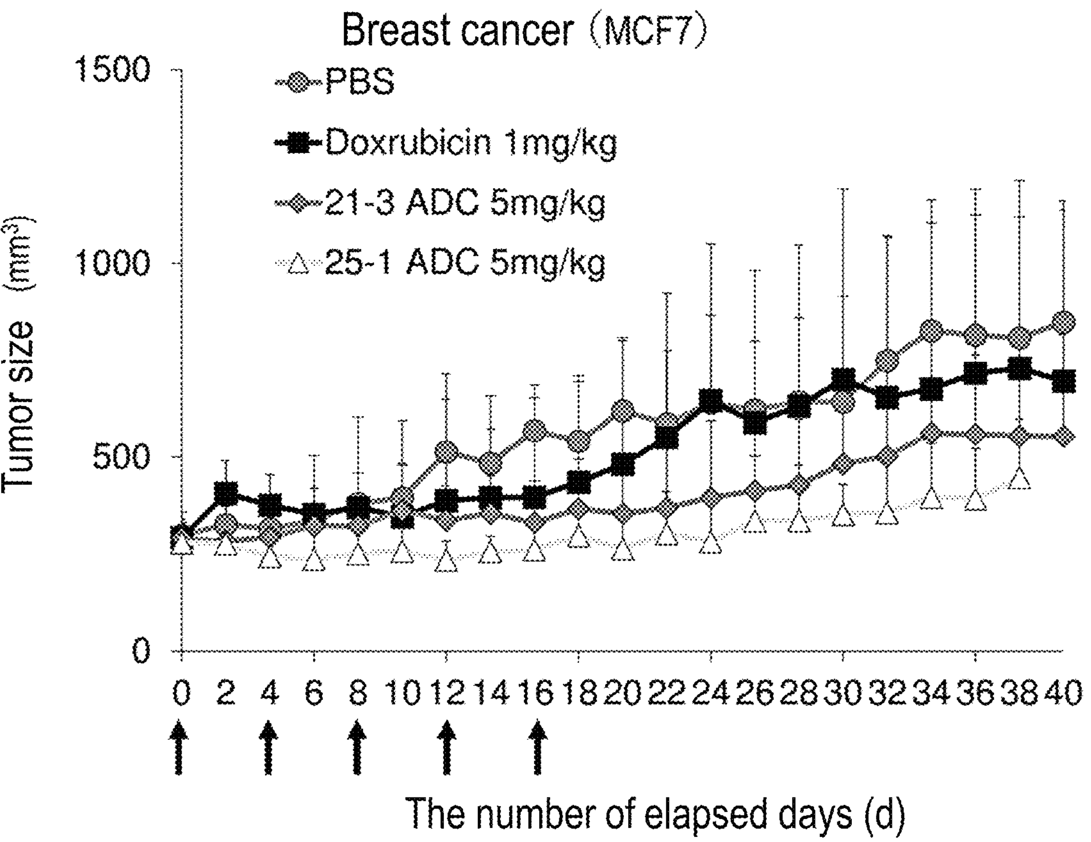
FIG. 25 shows the in-vivo antitumor effect of ADC against the tumor tissues of cancer-bearing mouse models in which a breast cancer cell line (MCF7) was subcutaneously transplanted. The arrows in the graph depict the timings of administration.
Figure 25:
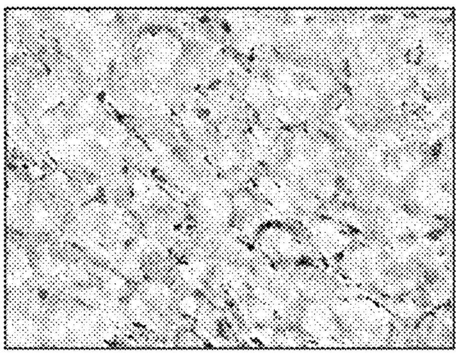

The results were as shown in FIG. 11. As shown in FIG. 11, 25-1ADC was found to exert strong antitumor activity against lung cancer while 21-3ADC was found to exert weak antitumor activity thereagainst. As is evident from the tissue image, mouse MEFLIN-positive cells were found in the stromal cells of the tumor though the lung cancer cells themselves were human MEFLIN-negative. The original tissues were MEFLIN-negative, demonstrating that the MEFLIN-positive cells were recruited to the vicinity of the tumor. It was also suggested that the ADC exerted antitumor activity against the tumor.

Cytotoxicity of ADC in Model with Subcutaneously Transplanted Neuroblastoma Cell Line $1.0\times10^7$ cells of an endogenous Meflin-positive neuroblastoma (NB-1) cell line were subcutaneously transplanted to the back of each female NOD SCID mouse (n=5 per group). ADC was intraperitoneally administered to the mouse having a tumor volume of approximately 250 $mm^3$ (5 mg/kg body weight; a total of 5 doses were administered at 4-day intervals). The length (L) and width (W) of tumor were measured using electric calipers, and the volume was calculated according to $V=L\times W^2\times 0.52$. The tumor formed by the transplantation of the NB-1 cell line was subjected to ISH staining.

Figure 12:
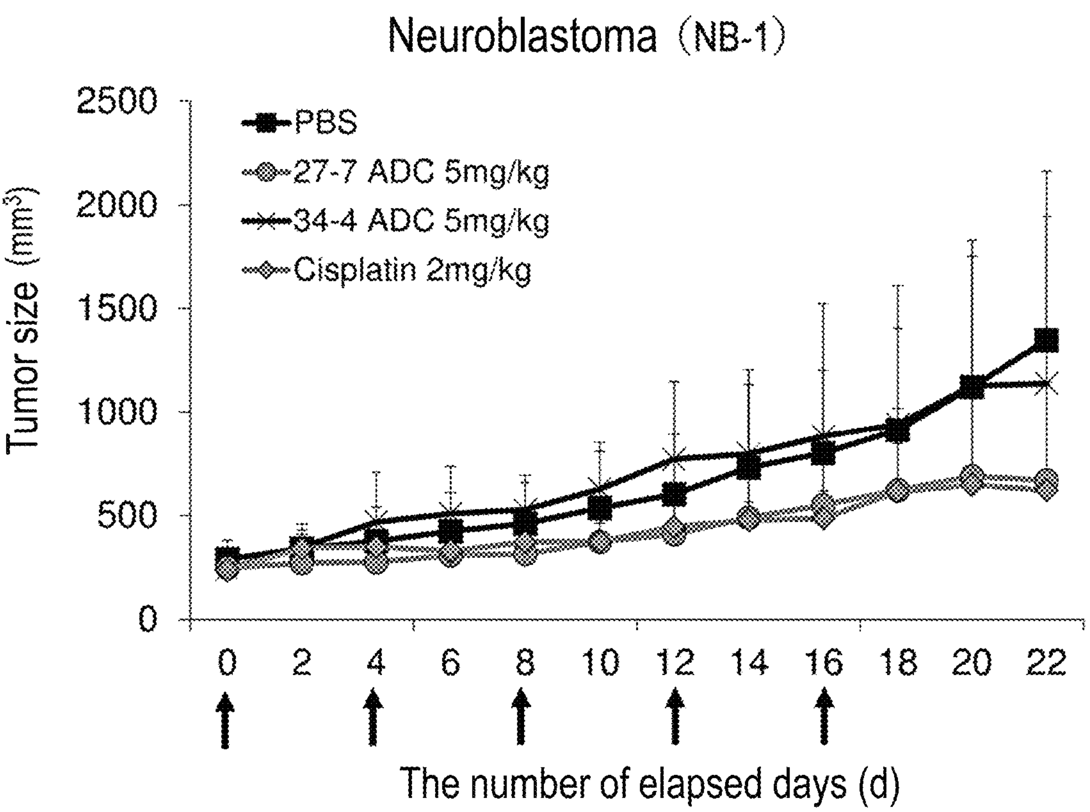
FIG. 12 shows the in-vivo antitumor effect of ADC against cancer-bearing mouse models in which a neuroblastoma cell line (NB-1) was subcutaneously transplanted. The arrows in the graph depict the timings of administration.
Figure 12:
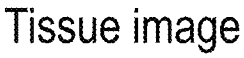
Figure 12:
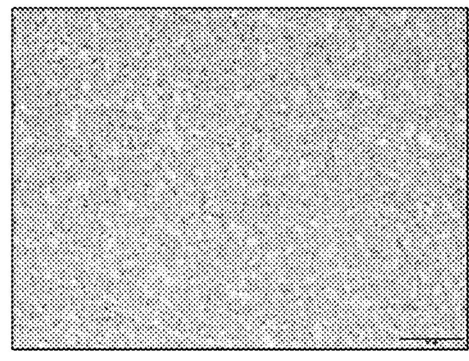

The results were as shown in FIG. 12. As shown in FIG. 12, 27-7ADC and 34-4ADC were found to exert antitumor activity, albeit weak, against neuroblastoma. As is evident from the tissue image, the tumor moderately expressed human MEFLIN.

Cytotoxicity of ADC in Model with Subcutaneously Transplanted Colorectal Cancer Cell Line $1.0\times 10^7$ cells of an endogenous Meflin-negative human colorectal cancer (DLD-1) cell line were subcutaneously transplanted to the back of each female nude mouse (BALB/cS1c nu/nu) (n=5 per group). ADC was intraperitoneally administered to the mouse having a tumor volume of approximately 200 $mm^3$ (5 mg/kg body weight; a total of 5 doses were administered at 4-day intervals). The length (L) and width (W) of tumor were measured using electric calipers, and the volume was calculated according to $V=L\times W^2\times 0.52$. The tumor formed by the transplantation of the DLD-1 cell line was subjected to ISH staining.

Figure 13:
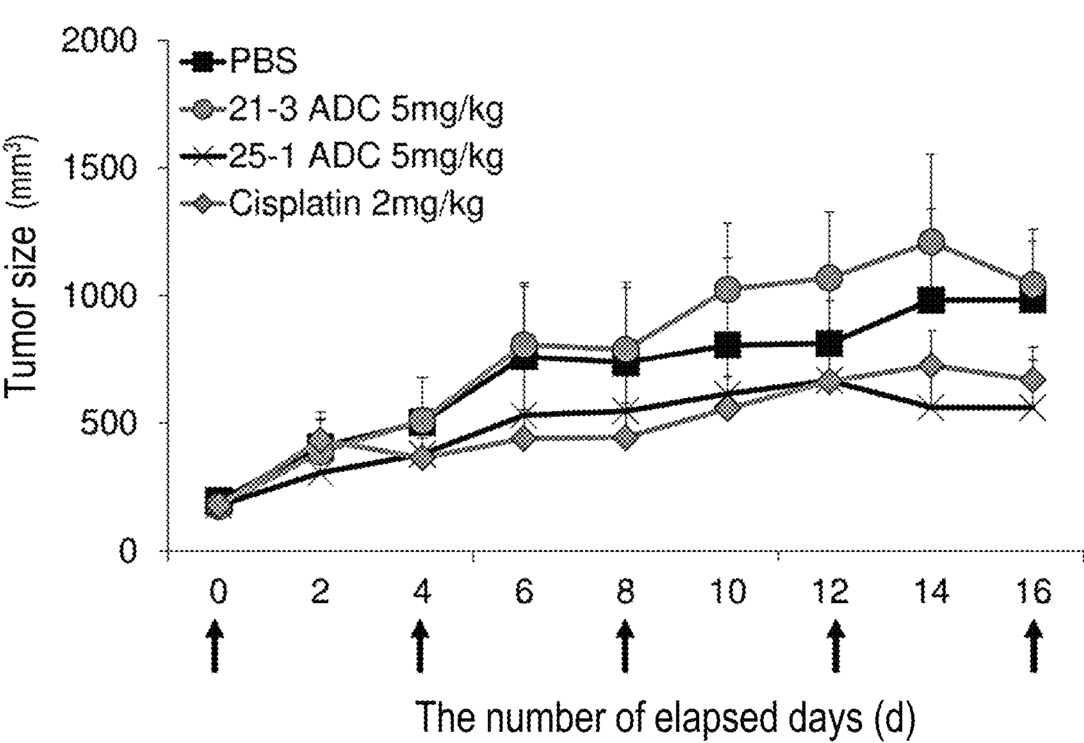
FIG. 13 shows the in-vivo antitumor effect of ADC against cancer-bearing mouse models in which a colorectal cancer cell line (DLD-1) was subcutaneously transplanted. The arrows in the graph depict the timings of administration.
Figure 13:
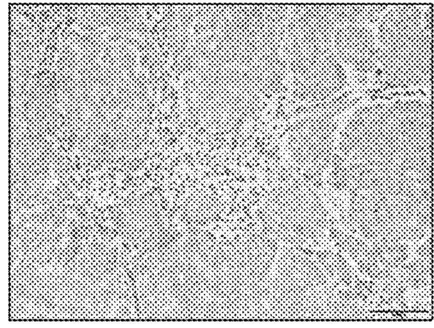

The results were as shown in FIG. 13. As shown in FIG. 13, 25-1ADC was found to exert weak antitumor activity against colorectal cancer while 21-3ADC was found to exhibit no antitumor activity thereagainst. As is evident from the tissue image, mouse MEFLIN-positive cells were found in the stromal cells of the tumor though the colorectal cancer cells themselves were human MEFLIN-negative. The original tissues were MEFLIN-negative, demonstrating that the MEFLIN-positive cells were recruited to the vicinity of the tumor. It was also suggested that the ADC exerted antitumor activity against the tumor.

Cytotoxicity of ADC in Model with Subcutaneously Transplanted Stomach Cancer Cell Line $1.0\times 10^7$ cells of an endogenous Meflin-negative human stomach cancer (MKN45) cell line were subcutaneously transplanted to the back of each female nude mouse (BALB/cS1c nu/nu) (n=5 per group). ADC was intraperitoneally administered to the mouse having a tumor volume of approximately 200 $mm^3$ (5 mg/kg body weight; a total of 5 doses were administered at 4-day intervals). The length (L) and width (W) of tumor were measured using electric calipers, and the volume was calculated according to $V=L\times W^2\times 0.52$. The tumor formed by the transplantation of the MKN45 cell line was subjected to ISH staining.

Figure 14:
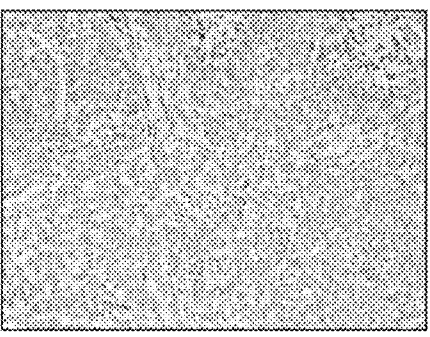
FIG. 14 shows the in-vivo antitumor effect of ADC against cancer-bearing mouse models in which a stomach cancer cell line (MKN45) was subcutaneously transplanted. The arrows in the graph depict the timings of administration.
Figure 21:
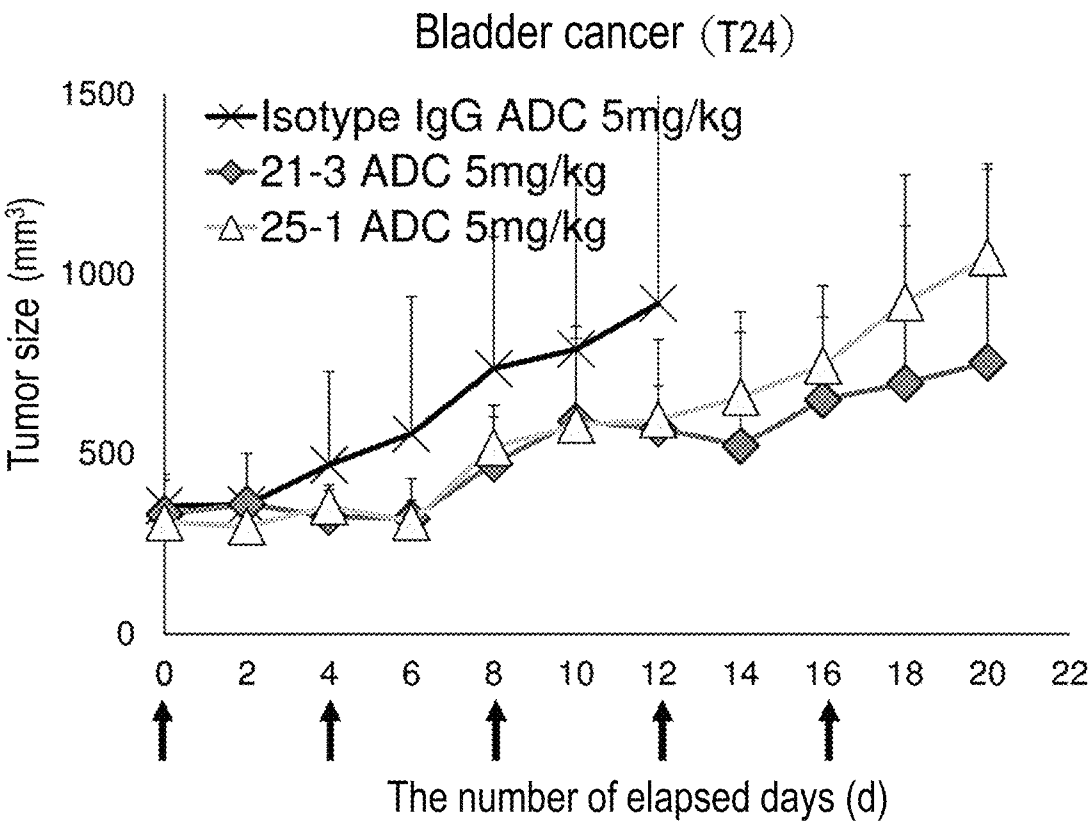
FIG. 21 shows the in-vivo antitumor effect of ADC against the tumor tissues of cancer-bearing mouse models in which a bladder cancer cell line (T24) was subcutaneously transplanted. The arrows in the graph depict the timings of administration.
Figure 21:
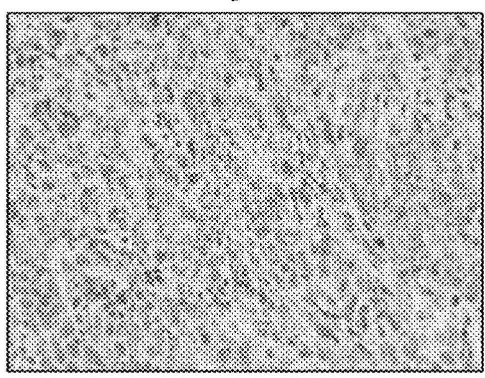

The results were as shown in FIG. 14. As shown in FIG. 14, 21-3ADC and 25-1ADC were found to exert strong antitumor activity against stomach cancer. As is evident from the tissue image, mouse MEFLIN-positive cells were found in the stromal cells of the tumor though the stomach cancer cells themselves were human MEFLIN-negative. The original tissues were MEFLIN-negative, demonstrating that the MEFLIN-positive cells were recruited to the vicinity of the tumor. It was also suggested that the ADC exerted antitumor activity against the tumor.

Single-Cell Analysis in Mouse Pancreas

Figure 15:
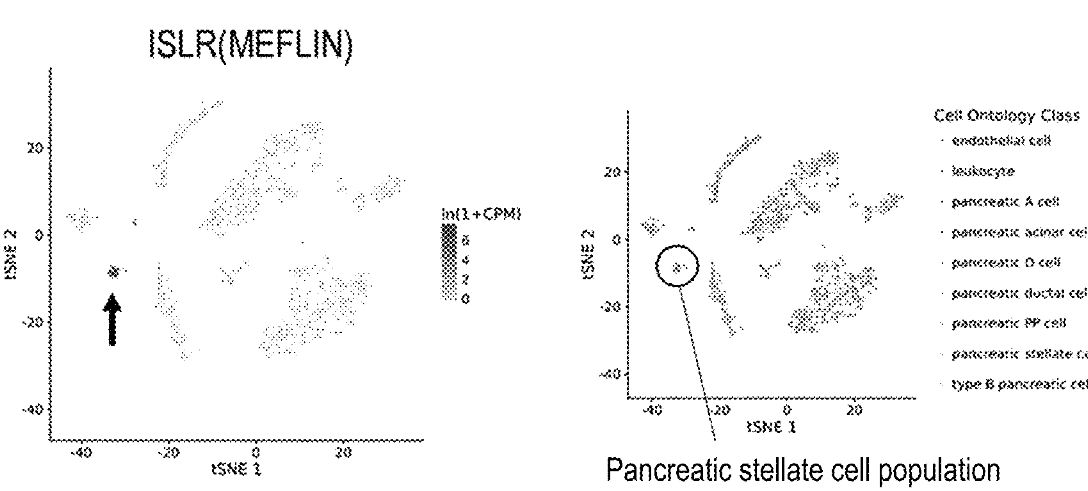
FIG. 15 shows results of analyzing single-cell RNA sequencing data (Tabula Muris) using the mouse pancreas deposited on the internet. It is shown that a MEFLIN-positive cell population in the mouse pancreas corresponds to a cathepsin K-positive cell population (arrows).
Figure 15:
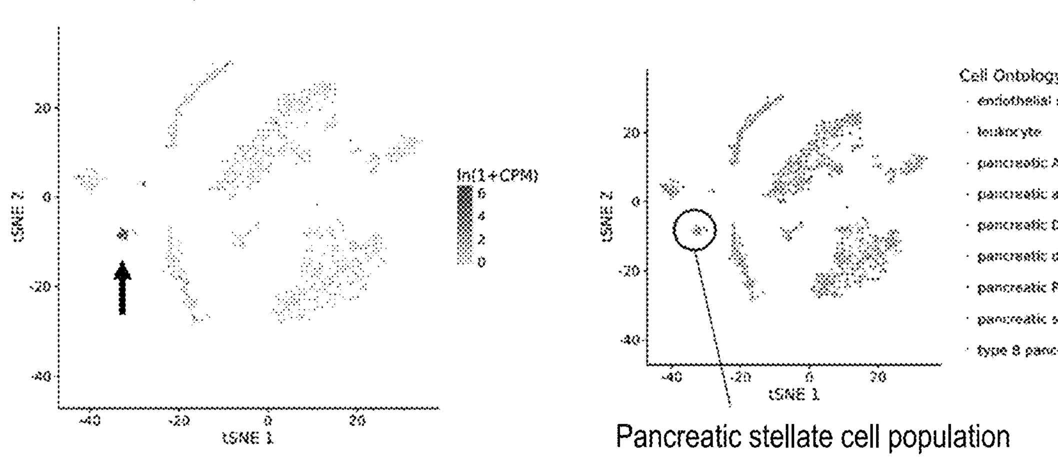

In FIG. 15, single-cell RNA sequencing data (Tabula Muris) (see Non Patent Literature 7) was analyzed on cell populations derived from the mouse pancreas published on the internet. tSNE (t-distributed stochastic neighbor embedding) depicted on each of the ordinate and the abscissa represents a numeric value that indicates multidimensional data constituted by a large amount of RNA expression level data which was compressed into one dimension by non-linear conversion. Specifically, according to FIG. 15, a large amount of RNA expression level data on individual expressing cells can be projected onto a two-dimensional plane using tSNE1 and tSNE2 so that cells can be clustered on the basis of gene expression profiles. This approach helps people understand, for example, what cell cluster is formed by individual cells indicated by circle marks. As a result, the clustering approach enables confirmation of whether a group of cells expressing a particular factor corresponds to a group of cells expressing another particular factor and additionally enables determination of cell types to which the cell groups correspond. FIG. 15 shows that pancreatic stellate cells of the mouse pancreas express both MEFLIN and cathepsin K, and shows that in the mouse pancreas, the MEFLIN-positive cell population corresponds to the cathepsin K-positive cell population (see the arrows in the drawing).

Single-Cell Analysis in Mouse Lung

Figure 16:
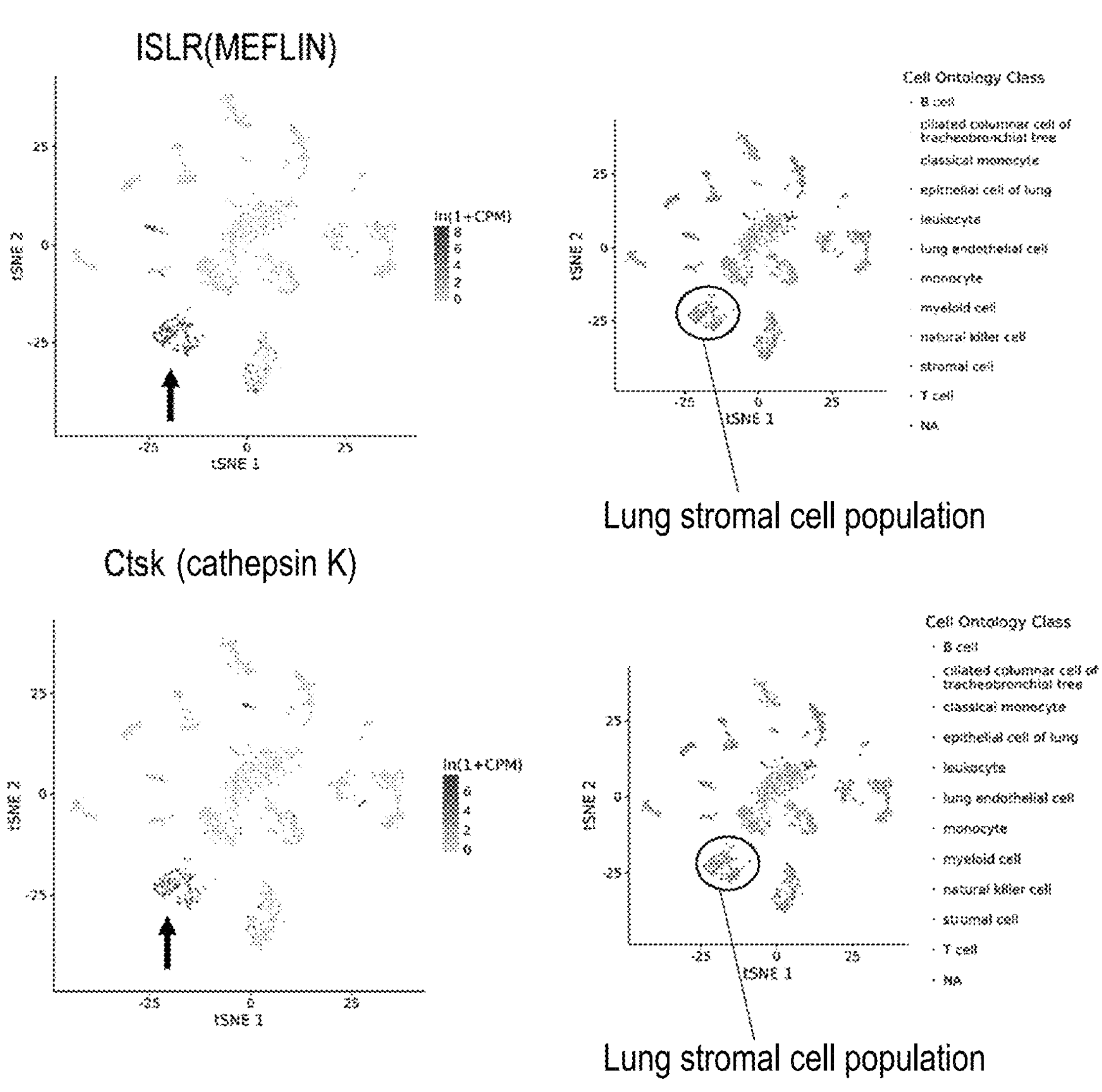
FIG. 16 shows results of analyzing single-cell RNA sequencing data (Tabula Muris) using the mouse lung deposited on the internet. It is shown that a MEFLIN-positive cell population in the mouse lung corresponds to a cathepsin K-positive cell population (arrows).

In FIG. 16, single-cell RNA sequencing data (Tabula Muris) (see Non Patent Literature 7) was analyzed on cell populations derived from the mouse lung published on the internet. This drawing shows that stromal cells of the mouse lung express both MEFLIN and cathepsin K, and shows that in the mouse lung, the MEFLIN-positive cell population corresponds to the cathepsin K-positive cell population (see the arrows in the drawing). (see the arrows in the drawing).

Figure 17:
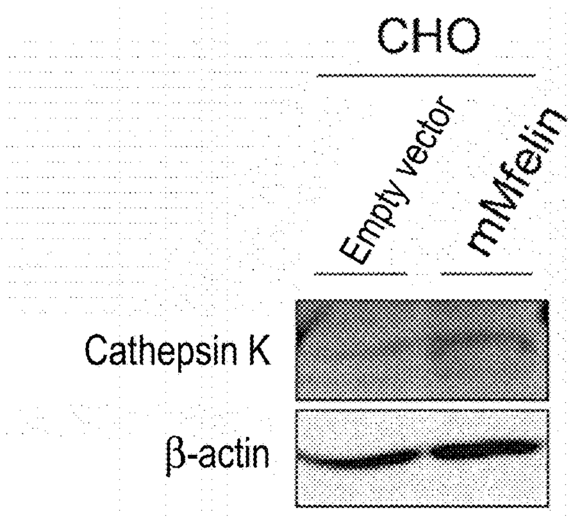
FIG. 17 shows the expression of cathepsin K in a CHO cell line expressing exogenous mouse MEFLIN.

CHO cells were allowed to express the full-length mouse MEFLIN protein, and Western blotting was attempted on a cell lysate thereof. The results were as shown in FIG. 17. As shown in FIG. 17, the expression of endogenous cathepsin K was elevated by allowing the CHO cells to express the full-length mouse MEFLIN protein.

Immunofluorescence Double Staining Method of Osteosarcoma Tissue

Figure 18:
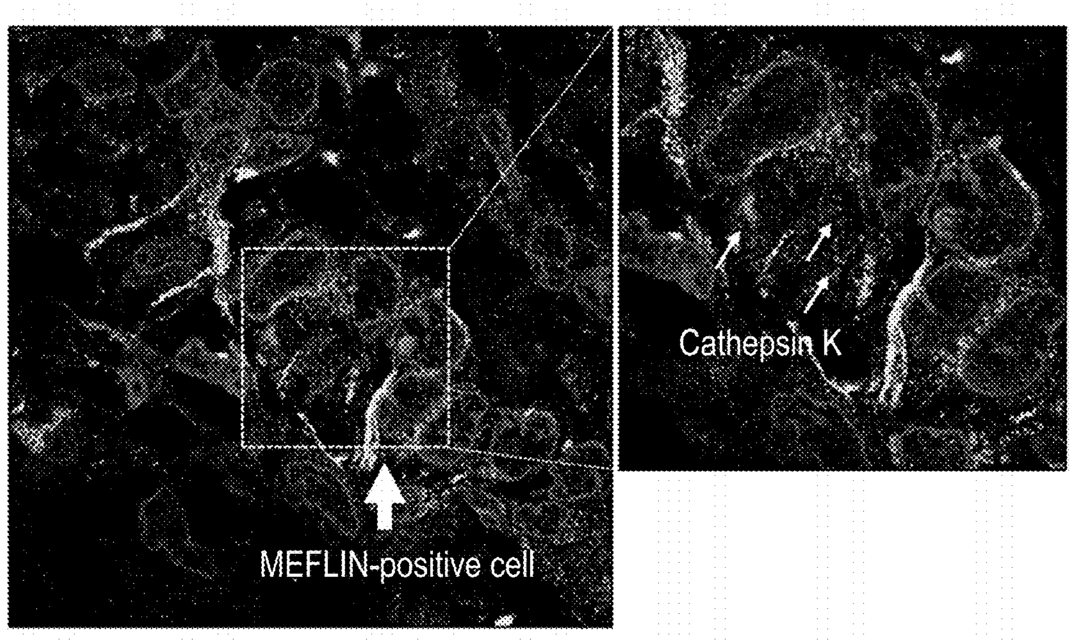
FIG. 18 shows results of performing an immunofluorescence double staining method using an anti-MEFLIN monoclonal antibody and an anti-cathepsin K antibody on the tumor tissues of cancer-bearing mouse models in which an osteosarcoma cell line (HsOs1) was subcutaneously transplanted. It is shown that cathepsin K (red) was secreted around MEFLIN-positive cells (green) (arrow).

FIG. 18 shows results of performing the immunofluorescence double staining method using an anti-MEFLIN monoclonal antibody and an anti-cathepsin K antibody on the tumor tissues of cancer-bearing mouse models in which an osteosarcoma cell line (HsOs1) was subcutaneously transplanted. It is shown that cathepsin K (red) was secreted around MEFLIN-positive cells (green) (arrow).

The results were as shown in FIG. 18. As shown in FIG. 18, it was possible to confirm the presence of cathepsin K (red) around MEFLIN-positive cells (green) (arrow in the enlarged view).

Immunofluorescence Double Staining Method of Pancreatic Cancer Tissue

Figure 19:
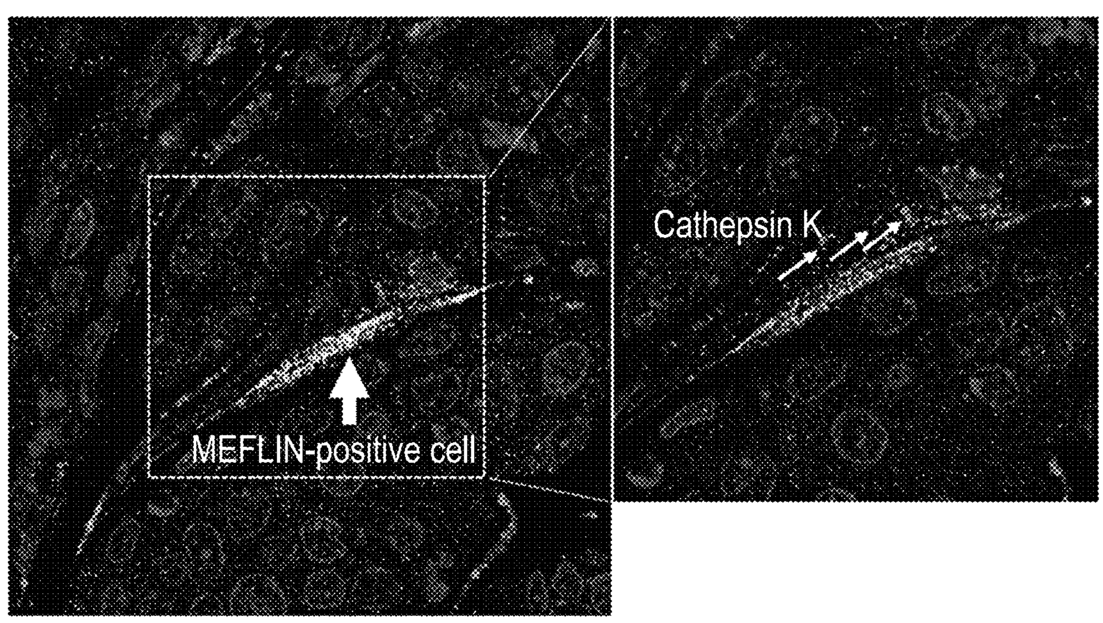
FIG. 19 shows results of performing an immunofluorescence double staining method using an anti-MEFLIN monoclonal antibody and an anti-cathepsin K antibody on the tumor tissues of cancer-bearing mouse models in which a pancreatic cancer cell line (BxPC-3) was subcutaneously transplanted. It is shown that cathepsin K (red) was secreted around MEFLIN-positive cells (green) (arrow).

FIG. 19 shows results of performing the immunofluorescence double staining method using an anti-MEFLIN monoclonal antibody and an anti-cathepsin K antibody on the tumor tissues of cancer-bearing mouse models in which a pancreatic cancer cell line (BxPC-3) was subcutaneously transplanted. It is shown that cathepsin K (red) was secreted around MEFLIN-positive cells (green) (arrow).

The results were as shown in FIG. 19. As shown in FIG. 19, it was possible to confirm the presence of cathepsin K (red) around MEFLIN-positive cells (green) (arrow in the enlarged view).

These results demonstrated that: when human MEFLIN-negative cancer cells are transplanted to mice, MEFLIN-positive cells are recruited into tissues containing the cancer cells; and ADC targeting the recruited MEFLIN-positive cells is beneficial for the treatment of the cancer. These results also demonstrated that ADC targeting the human MEFLIN protein is not necessarily required to have internalization activity. An enzyme, such as cathepsin, which cleaves a valine-citrulline linker resides in the stroma containing MEFLIN protein-positive cells, and this enzyme presumably allows ADC that is not internalized into cells to exhibit cytotoxicity.

Cytotoxicity of ADC in Model with Subcutaneously Transplanted Bile Duct Cancer Cell Line $1.0\times10^7$ cells of an endogenous Meflin-negative human bile duct cancer (HuCCT1) cell line were subcutaneously transplanted to the back of each female NOD SCID mouse (n=5 per group). ADC was administered to the tail vein of the mouse having a tumor volume of approximately 250 $mm^3$ (5 mg/kg body weight; a total of 3 doses were administered at 4-day intervals). The length (L) and width (W) of tumor were measured using electric calipers, and the volume was calculated according to $V=L\times W^2\times0.52$. The tumor formed by the transplantation of the HuCCT1 cell line was subjected to ISH staining.

Figure 20:
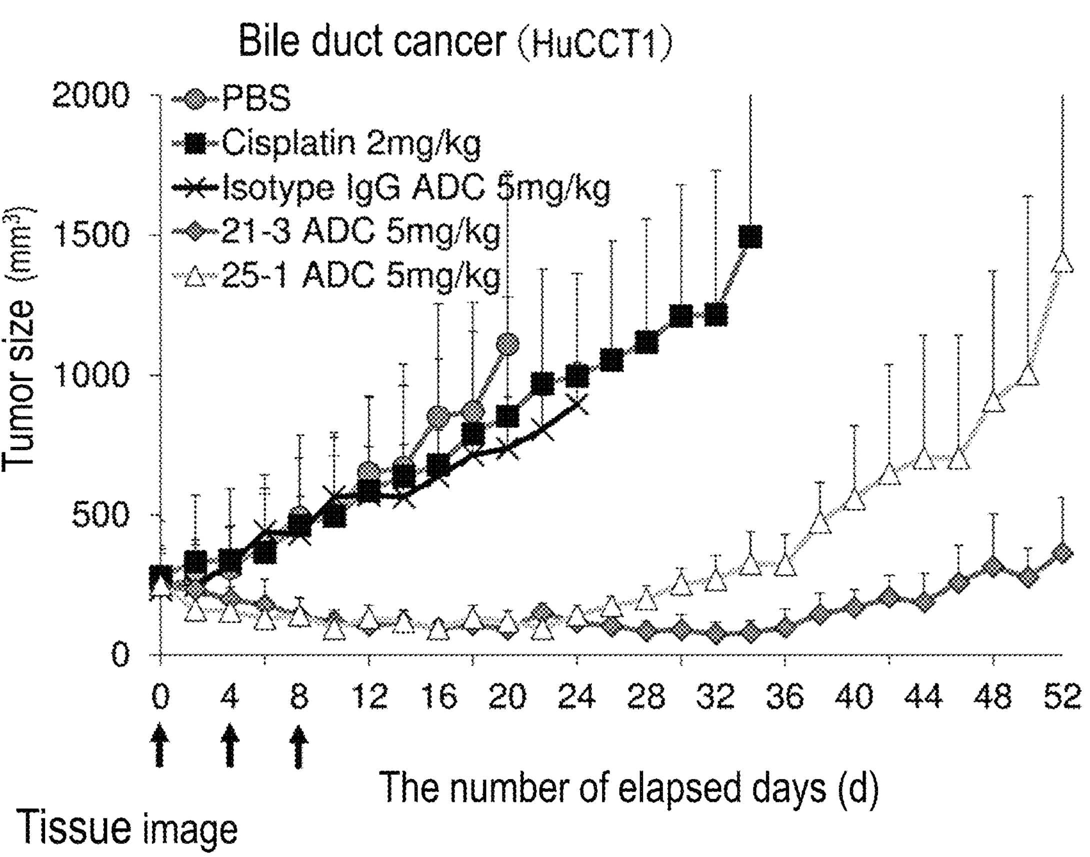
FIG. 20 shows the in-vivo antitumor effect of ADC against the tumor tissues of cancer-bearing mouse models in which a bile duct cancer cell line (HuCCT1) was subcutaneously transplanted. The arrows in the graph depict the timings of administration.
Figure 20:
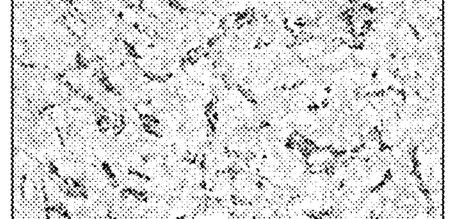

The results were as shown in FIG. 20. As shown in the tissue image of FIG. 20, mouse MEFLIN-positive cells were found in the stromal cells of the tumor though the bile duct cancer cells themselves were MEFLIN-negative. 21-3ADC and 25-1ADC were found to exert potent antitumor activity against bile duct cancer. The original tissues were MEFLIN-negative, demonstrating that the MEFLIN-positive cells were recruited to the vicinity of the tumor. It was also suggested that the ADC exerted antitumor activity against the tumor.

Cytotoxicity of ADC in Model with Subcutaneously Transplanted Bladder Cancer Cell Line $1.0\times10^7$ cells of an endogenous Meflin-negative human bladder cancer (T24) cell line were subcutaneously transplanted to the back of each female NOD SCID mouse (n=4 per group). ADC was administered to the tail vein of the mouse having a tumor volume of approximately 300 $mm^3$ (5 mg/kg body weight; a total of 5 doses were administered at 4-day intervals). The length (L) and width (W) of tumor were measured using electric calipers, and the volume was calculated according to $V=L\times W^2\times0.52$. The tumor formed by the transplantation of the T24 cell line was subjected to ISH staining.

The results were as shown in FIG. 21. As shown in the tissue image of FIG. 21, mouse MEFLIN-positive cells were found in the stromal cells of the tumor though the bladder cancer cells themselves were MEFLIN-negative. 21-3ADC and 25-1ADC were found to exert weak antitumor activity against bladder cancer. The original tissues were MEFLIN-negative, demonstrating that the MEFLIN-positive cells were recruited to the vicinity of the tumor. It was also suggested that the ADC exerted antitumor activity against the tumor.

Cytotoxicity of ADC in Model with Subcutaneously Transplanted Ovary Cancer Cell Line $1.0\times10^7$ cells of an endogenous Meflin-negative human ovary cancer (OV-90) cell line were subcutaneously transplanted to the back of each female NOD SCID mouse (n=5 per group). ADC was intraperitoneally administered to the mouse having a tumor volume of approximately 100 $mm^3$ (5 mg/kg body weight; a total of 5 doses were administered at 4-day intervals). The length (L) and width (W) of tumor were measured using electric calipers, and the volume was calculated according to $V=L\times W^2\times0.52$. The tumor formed by the transplantation of the OV-90 cell line was subjected to ISH staining.

Figure 22:
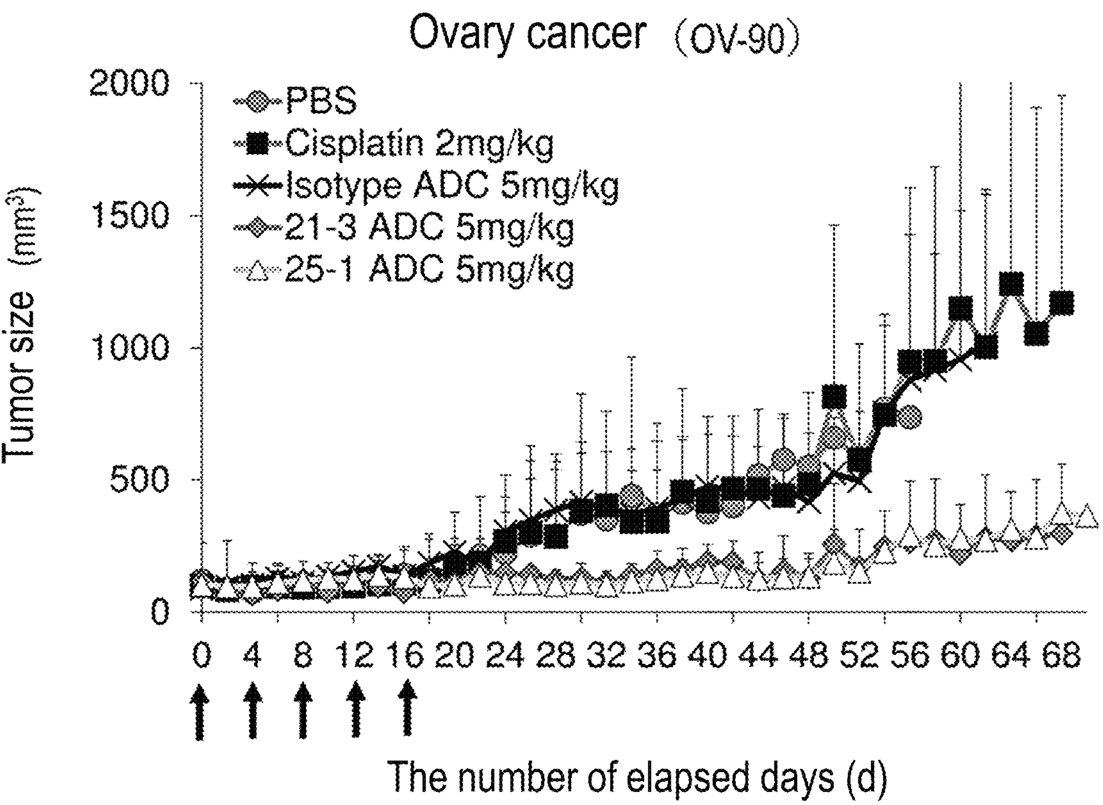
FIG. 22 shows the in-vivo antitumor effect of ADC against the tumor tissues of cancer-bearing mouse models in which an ovary cancer cell line (OV-90) was subcutaneously transplanted. The arrows in the graph depict the timings of administration.
Figure 22:
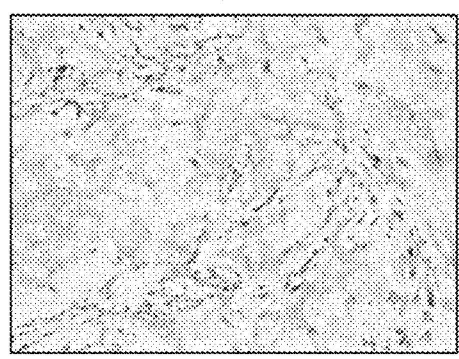

The results were as shown in FIG. 22. As shown in the tissue image of FIG. 22, mouse MEFLIN-positive cells were found in the stromal cells of the tumor though the ovary cancer cells themselves were MEFLIN-negative. 21-3ADC and 25-1ADC were found to exert potent antitumor activity against ovary cancer. The original tissues were MEFLIN-negative, demonstrating that the MEFLIN-positive cells were recruited to the vicinity of the tumor. It was also suggested that the ADC exerted antitumor activity against the tumor.

Cytotoxicity of ADC in Model with Subcutaneously Transplanted Esophageal Cancer Cell Line $1.0\times10^7$ cells of an endogenous Meflin-negative human esophageal cancer (KYSE) cell line were subcutaneously transplanted to the back of each female NOD SCID mouse (n=5 per group). ADC was intraperitoneally administered to the mouse having a tumor volume of approximately 200 $mm^3$ (5 mg/kg body weight; a total of 5 doses were administered at 4-day intervals). The length (L) and width (W) of tumor were measured using electric calipers, and the volume was calculated according to $V=L\times W^2\times0.52$. The tumor formed by the transplantation of the KYSE cell line was subjected to ISH staining.

Figure 23:
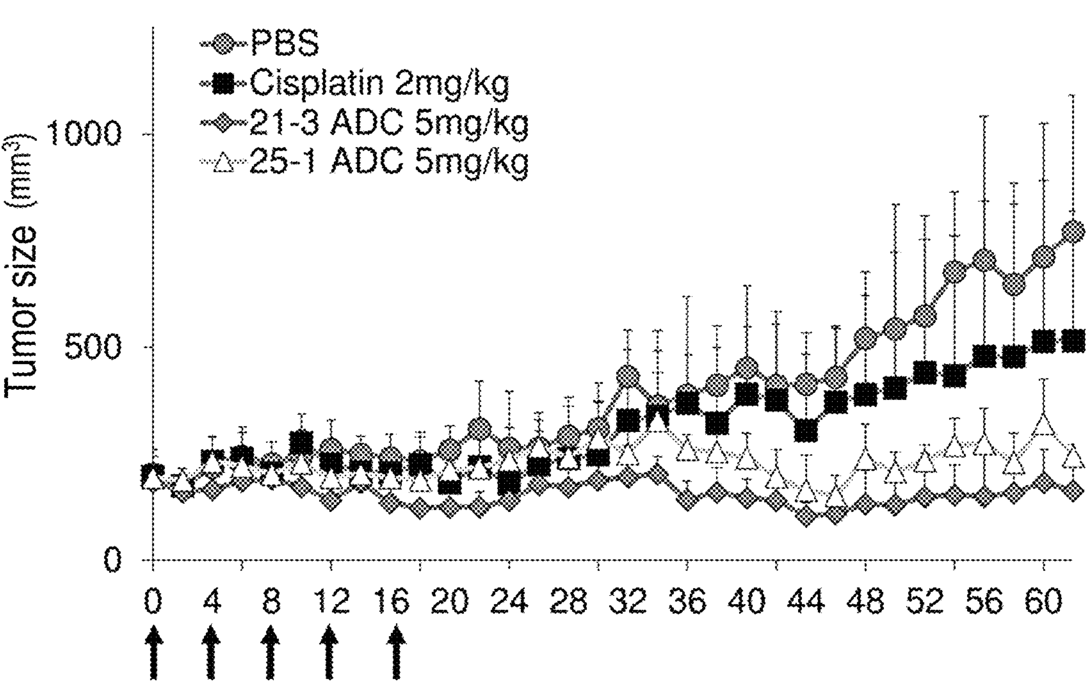
FIG. 23 shows the in-vivo antitumor effect of ADC against the tumor tissues of cancer-bearing mouse models in which an esophageal cancer cell line (KYSE) was subcutaneously transplanted. The arrows in the graph depict the timings of administration.
Figure 23:
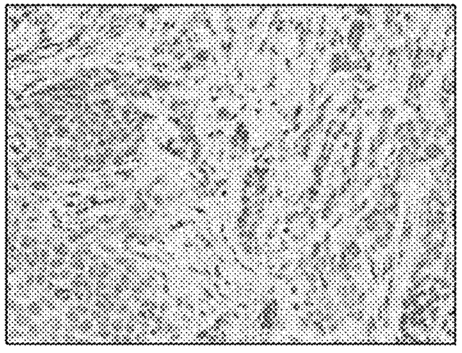

The results were as shown in FIG. 23. As shown in the tissue image of FIG. 23, mouse MEFLIN-positive cells were found in the stromal cells of the tumor though the esophageal cancer cells themselves were MEFLIN-negative. 21-3ADC and 25-1ADC were found to exert potent antitumor activity against esophageal cancer. The original tissues were MEFLIN-negative, demonstrating that the MEFLIN-positive cells were recruited to the vicinity of the tumor. It was also suggested that the ADC exerted antitumor activity against the tumor.

Cytotoxicity of ADC in Model with Subcutaneously Transplanted Osteosarcoma Cell Line $1.0\times10^7$ cells of an endogenous Meflin-positive osteosarcoma (HsOs1) cell line were subcutaneously transplanted to the back of each female NOD SCID mouse (n=4 per group). ADC was administered to the tail vein of the mouse having a tumor volume of approximately 250 $mm^3$ (5 mg/kg body weight; a total of 5 doses were administered at 4-day intervals). The length (L) and width (W) of tumor were measured using electric calipers, and the volume was calculated according to $V=L\times W^2\times0.52$. The tumor formed by the transplantation of the HsOs1 cell line was subjected to ISH staining.

Figure 24:
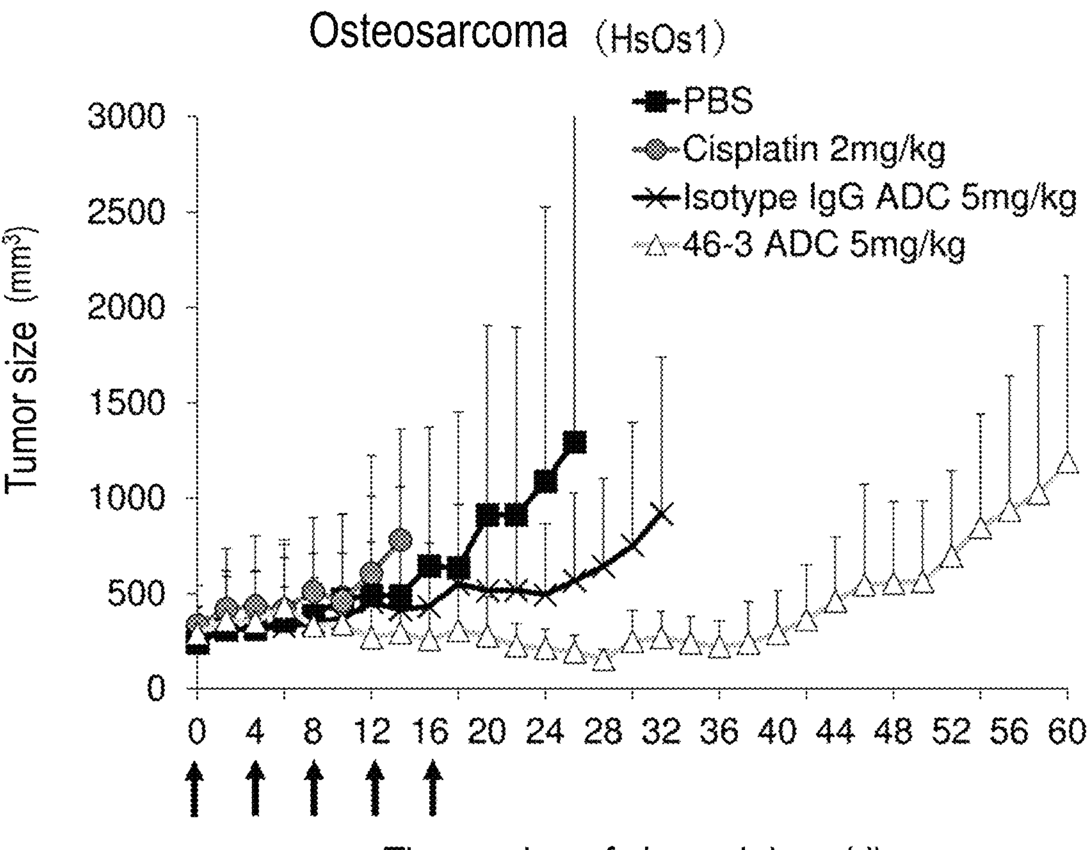
FIG. 24 shows the in-vivo antitumor effect of ADC against the tumor tissues of cancer-bearing mouse models in which an osteosarcoma cell line (HsOs1) was subcutaneously transplanted. The arrows in the graph depict the timings of administration.

The results were as shown in FIG. 24. As shown in FIG. 24, 46-3ADC was found to exert potent antitumor activity against osteosarcoma. The tumor moderately expressed human MEFLIN (see FIG. 9).

Cytotoxicity of ADC in Model with Subcutaneously Transplanted Breast Cancer Cell Line $1.0\times10^7$ cells of an endogenous Meflin-negative human breast cancer (MCF-7) cell line were subcutaneously transplanted to the back of each female nude mouse (BALB/cS1c nu/nu) (n=5 per group). ADC was administered to the tail vein of the mouse having a tumor volume of approximately 300 $mm^3$ (5 mg/kg body weight; a total of 5 doses were administered at 4-day intervals). The length (L) and width (W) of tumor were measured using electric calipers, and the volume was calculated according to $V=L\times W^2\times0.52$. The tumor formed by the transplantation of the MCF-7 cell line was subjected to ISH staining.

The results were as shown in FIG. 25. As shown in the tissue image of FIG. 25, mouse MEFLIN-positive cells were found in the stromal cells of the tumor though the breast cancer cells themselves were MEFLIN-negative. 21-3ADC and 25-1ADC were found to exert weak antitumor activity against breast cancer. The original tissues were MEFLIN-negative, demonstrating that the MEFLIN-positive cells were recruited to the vicinity of the tumor. It was also suggested that the ADC exerted antitumor activity against the tumor.

Evaluation of Validity of Immunohistochemical Staining of Human Pancreatic Cancer Tissue The subject samples used were serial sections of a surgical specimen of human pancreatic cancer. Immunohistochemical staining using an anti-MEFLIN antibody was carried out on the serial sections of a surgical specimen of human pancreatic cancer, and the expression of MEFLIN in the human tissues was confirmed using an anti-MEFLIN antibody. Also, the expression of human MEFLIN mRNA in these serial sections was confirmed by in situ hybridization.

Figure 26:
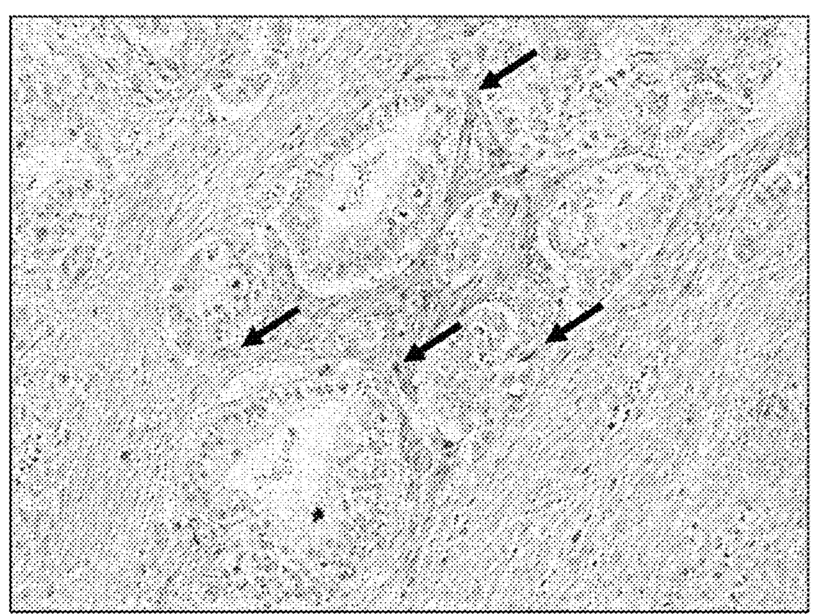
FIG. 26 shows a result of subjecting a tissue section of a surgical specimen of human pancreatic cancer to immunohistochemical (IHC) staining using an anti-MEFLIN antibody, and a result of staining the tissue section by in situ hybridization (ISH). The arrows in the drawing represent that the sites were the same between the upper and lower images.
Figure 26:
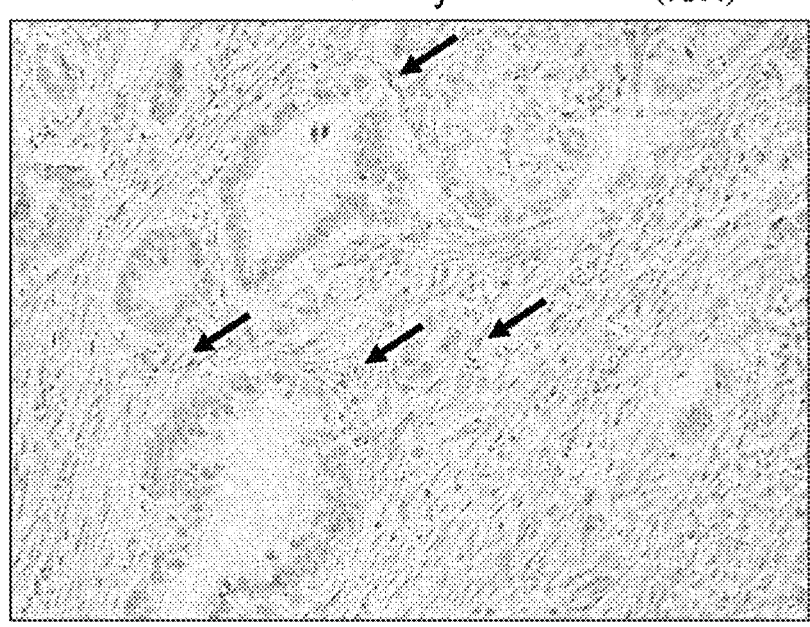

The results were as shown in FIG. 26. MEFLIN-positive cells by immunohistochemical staining and MEFLIN-positive cells by in situ hybridization were identical in the human pancreatic cancer tissues, and the immunohistochemical staining using an anti-MEFLIN antibody was able to confirm the expression of MEFLIN in the human tissues. The arrows respectively depict MEFLIN confirmed by the immunohistochemical staining (upper image in FIG. 26) and MEFLIN confirmed by the in situ hybridization (lower image in FIG. 26) in the human pancreatic cancer tissues. The positions of the arrows in the upper and lower images in FIG. 26 correspond to each other and refer to the same cells.

The invention claimed is:

1. An antibody that binds to MEFLIN, the antibody being selected from the group consisting of the following antibodies:

(1A) an antibody having a heavy chain variable region comprising heavy chain CDR1 having the amino acid sequence set forth in SEQ ID NO: 1, heavy chain CDR2 having the amino acid sequence set forth in SEQ ID NO: 2, and heavy chain CDR3 having the amino acid sequence set forth in SEQ ID NO: 3, and a light chain variable region comprising light chain CDR1 having the amino acid sequence set forth in SEQ ID NO: 4, light chain CDR2 having the amino acid sequence set forth in SEQ ID NO: 5, and light chain CDR3 having the amino acid sequence set forth in SEQ ID NO: 6;

(1B) an antibody having a heavy chain variable region having the amino acid sequence set forth in SEQ ID NO: 7 and a light chain variable region having the amino acid sequence set forth in SEQ ID NO: 8;

(2A) an antibody having a heavy chain variable region comprising the heavy chain CDR1 set forth in SEQ ID NO: 9, the heavy chain CDR2 set forth in SEQ ID NO: 10, and the heavy chain CDR3 set forth in SEQ ID NO: 11, and a light chain variable region comprising the light chain CDR1 set forth in SEQ ID NO: 12, the light chain CDR2 set forth in SEQ ID NO: 13, and the light chain CDR3 set forth in SEQ ID NO: 14;

(2B) an antibody having the heavy chain variable region set forth in SEQ ID NO: 15 and the light chain variable region set forth in SEQ ID NO: 16;

(3A) an antibody having a heavy chain variable region comprising the heavy chain CDR1 set forth in SEQ ID NO: 17, the heavy chain CDR2 set forth in SEQ ID NO: 18, and the heavy chain CDR3 set forth in SEQ ID NO: 19, and a light chain variable region comprising the light chain CDR1 set forth in SEQ ID NO: 20, the light chain CDR2 set forth in SEQ ID NO: 21, and the light chain CDR3 set forth in SEQ ID NO: 22;

(3B) an antibody having the heavy chain variable region set forth in SEQ ID NO: 23 and the light chain variable region set forth in SEQ ID NO: 24;

(4A) an antibody having a heavy chain variable region comprising the heavy chain CDR1 set forth in SEQ ID NO: 25, the heavy chain CDR2 set forth in SEQ ID NO: 26, and the heavy chain CDR3 set forth in SEQ ID NO: 27, and a light chain variable region comprising the light chain CDR1 set forth in SEQ ID NO: 28, the light chain CDR2 set forth in SEQ ID NO: 29, and the light chain CDR3 set forth in SEQ ID NO: 30;

(4B) an antibody having the heavy chain variable region set forth in SEQ ID NO: 31 and the light chain variable region set forth in SEQ ID NO: 32;

(5A) an antibody having a heavy chain variable region comprising the heavy chain CDR1 set forth in SEQ ID NO: 33, the heavy chain CDR2 set forth in SEQ ID NO: 34, and the heavy chain CDR3 set forth in SEQ ID NO: 35, and a light chain variable region comprising the light chain CDR1 set forth in SEQ ID NO: 36, the light chain CDR2 set forth in SEQ ID NO: 37, and the light chain CDR3 set forth in SEQ ID NO: 38;

(5B) an antibody having the heavy chain variable region set forth in SEQ ID NO: 39 and the light chain variable region set forth in SEQ ID NO: 40;

(6A) an antibody having a heavy chain variable region comprising the heavy chain CDR1 set forth in SEQ ID NO: 41, the heavy chain CDR2 set forth in SEQ ID NO: 42, and the heavy chain CDR3 set forth in SEQ ID NO: 43, and a light chain variable region comprising the light chain CDR1 set forth in SEQ ID NO: 44, the light chain CDR2 set forth in SEQ ID NO: 45, and the light chain CDR3 set forth in SEQ ID NO: 46;

(6B) an antibody having the heavy chain variable region set forth in SEQ ID NO: 47 and the light chain variable region set forth in SEQ ID NO: 48;

(7A) an antibody having a heavy chain variable region comprising the heavy chain CDR1 set forth in SEQ ID NO: 57, the heavy chain CDR2 set forth in SEQ ID NO: 58, and the heavy chain CDR3 set forth in SEQ ID NO: 59, and a light chain variable region comprising the light chain CDR1 set forth in SEQ ID NO: 60, the light chain CDR2 set forth in SEQ ID NO: 61, and the light chain CDR3 set forth in SEQ ID NO: 62;

(7B) an antibody having the heavy chain variable region set forth in SEQ ID NO: 63 and the light chain variable region set forth in SEQ ID NO: 64; and (8A) an antibody having a heavy chain variable region comprising the heavy chain CDR1 set forth in SEQ ID NO: 81, the heavy chain CDR2 set forth in SEQ ID NO: 82, and the heavy chain CDR3 set forth in SEQ ID NO: 83, and a light chain variable region comprising the light chain CDR1 set forth in SEQ ID NO: 84, the light chain CDR2 set forth in SEQ ID NO: 85, and the light chain CDR3 set forth in SEQ ID NO: 86;

(8B) an antibody having the heavy chain variable region set forth in SEQ ID NO: 87 and the light chain variable region set forth in SEQ ID NO: 88.

2. A pharmaceutical composition comprising an antibody-drug conjugate (ADC) of an antibody according to claim 1 and a cytotoxic agent.

3. A method for treating a cancer in a subject, comprising administering to the subject the pharmaceutical composition of claim 2.

4. The method according to claim 3, wherein the cancer is sarcoma.

5. The method according to claim 4, wherein the cancer is a MEFLIN-positive sarcoma.

6. The method according to claim 4, wherein the sarcoma is selected from the group consisting of myxofibrosarcoma, malignant fibrous histiocytoma, liposarcoma, leiomyosarcoma, rhabdomyosarcoma, neuroblastoma, malignant peripheral nerve sheath tumor, Ewing's sarcoma, epithelioid sarcoma, clear cell sarcoma, synovial sarcoma, and osteosarcoma.

7. The method according to claim 3, wherein the cancer is carcinoma.

8. The method according to claim 3, wherein the cancer is selected from the group consisting of breast cancer, pancreatic cancer, lung cancer, colorectal cancer, stomach cancer, bile duct cancer, ovary cancer, bladder cancer, and esophageal cancer.

9. The method according to claim 3, wherein the cancer is MEFLIN-negative, and a stroma surrounding the cancer contains MEFLIN-positive cells.

10. The method according to claim 7, wherein the antibody has no internalization activity.

11. The method according to claim 4, wherein the antibody has internalization activity.

12. The method according to claim 10, wherein the antibody and the cytotoxic agent of the ADC are connected to each other via a linker, and wherein the linker is a cleavable linker.

13. The method according to claim 12, wherein the linker is cleaved by cathepsin K.

14. The method according to claim 13, wherein the linker comprises a valine-citrulline dipeptide and is cleaved in the presence of cathepsin K.

15. The pharmaceutical composition according to claim 2, wherein the antibody and the cytotoxic agent of the ADC are connected to each other via a linker, and wherein the linker is a non-cleavable linker.

* * * * *

```
                           SEQUENCE LISTING

<160> NUMBER OF SEQ ID NOS: 136

<210> SEQ ID NO 1
<211> LENGTH: 5
<212> TYPE: PRT
<213> ORGANISM: Artificial Sequence
<220> FEATURE:
<223> OTHER INFORMATION: 27-7 HCDR1

<400> SEQUENCE: 1

Lys Tyr Trp Met Asp
1               5


<210> SEQ ID NO 2
<211> LENGTH: 17
<212> TYPE: PRT
<213> ORGANISM: Artificial Sequence
<220> FEATURE:
<223> OTHER INFORMATION: 27-7 HCDR2

<400> SEQUENCE: 2

Glu Ile Asn Thr Asp Gly Ser Lys Thr Asn Tyr Ala Pro Ser Ile Lys
1               5                   10                  15

Asp


<210> SEQ ID NO 3
<211> LENGTH: 4
<212> TYPE: PRT
<213> ORGANISM: Artificial Sequence
<220> FEATURE:
<223> OTHER INFORMATION: 27-7 HCDR3

<400> SEQUENCE: 3

Trp Glu Asp Tyr
1


<210> SEQ ID NO 4
<211> LENGTH: 16
<212> TYPE: PRT
<213> ORGANISM: Artificial Sequence
<220> FEATURE:
<223> OTHER INFORMATION: 27-7 LCDR1

<400> SEQUENCE: 4

Lys Ser Ser Gln Ser Leu Val Tyr Ser Asp Gly Lys Thr Tyr Leu His
1               5                   10                  15


<210> SEQ ID NO 5
<211> LENGTH: 7
<212> TYPE: PRT
<213> ORGANISM: Artificial Sequence
<220> FEATURE:
<223> OTHER INFORMATION: 27-7 LCDR2
```

<400> SEQUENCE: 5

Gln Val Ser Asn Leu Asp Ser
1               5

<210> SEQ ID NO 6
<211> LENGTH: 9
<212> TYPE: PRT
<213> ORGANISM: Artificial Sequence
<220> FEATURE:
<223> OTHER INFORMATION: 27-7 LCDR3

<400> SEQUENCE: 6

Ala Gln Thr Thr His Phe Pro Tyr Thr
1               5

<210> SEQ ID NO 7
<211> LENGTH: 113
<212> TYPE: PRT
<213> ORGANISM: Artificial Sequence
<220> FEATURE:
<223> OTHER INFORMATION: 27-7 heavy chain variable region

<400> SEQUENCE: 7

Glu Val Gln Leu Val Glu Ser Gly Gly Ser Leu Val Gln Pro Gly Gly
1               5                   10                  15

Ser Leu Lys Leu Ser Cys Val Ala Ser Gly Tyr Thr Phe Ser Lys Tyr
            20                  25                  30

Trp Met Asp Trp Val Arg Gln Thr Pro Gly Lys Ser Leu Glu Trp Ile
        35                  40                  45

Gly Glu Ile Asn Thr Asp Gly Ser Lys Thr Asn Tyr Ala Pro Ser Ile
    50                  55                  60

Lys Asp Arg Phe Thr Ile Ser Arg Asp Asn Ala Lys Ser Thr Leu Tyr
65                  70                  75                  80

Leu Gln Met Ser Asn Val Lys Ser Asp Asp Thr Ala Ile Tyr Tyr Cys
                85                  90                  95

Thr Asn Trp Glu Asp Tyr Trp Gly Gln Gly Val Met Val Thr Val Ser
            100                 105                 110

Ser

<210> SEQ ID NO 8
<211> LENGTH: 112
<212> TYPE: PRT
<213> ORGANISM: Artificial Sequence
<220> FEATURE:
<223> OTHER INFORMATION: 27-7 light chain variable region

<400> SEQUENCE: 8

Asp Val Val Met Thr Gln Thr Pro Pro Ser Leu Ser Val Ala Ile Gly
1               5                   10                  15

Gln Ser Val Ser Ile Ser Cys Lys Ser Ser Gln Ser Leu Val Tyr Ser
            20                  25                  30

Asp Gly Lys Thr Tyr Leu His Trp Leu Leu Gln Ser Ser Gly Arg Ser
        35                  40                  45

Pro Lys Arg Leu Ile Tyr Gln Val Ser Asn Leu Asp Ser Gly Val Pro
    50                  55                  60

Asp Arg Phe Ser Gly Thr Gly Ser Gln Lys Asp Phe Thr Leu Lys Ile
65                  70                  75                  80

Ser Arg Val Glu Ala Lys Asp Leu Gly Val Tyr Tyr Cys Ala Gln Thr
                85                  90                  95

Thr His Phe Pro Tyr Thr Phe Gly Ala Gly Thr Lys Leu Glu Leu Lys
100 105 110

<210> SEQ ID NO 9
<211> LENGTH: 8
<212> TYPE: PRT
<213> ORGANISM: Artificial Sequence
<220> FEATURE:
<223> OTHER INFORMATION: 34-4 HCDR1

<400> SEQUENCE: 9

Gly Phe Ser Leu Thr Ser Tyr Asp
1 5

<210> SEQ ID NO 10
<211> LENGTH: 7
<212> TYPE: PRT
<213> ORGANISM: Artificial Sequence
<220> FEATURE:
<223> OTHER INFORMATION: 34-4 HCDR2

<400> SEQUENCE: 10

Ile Trp Gly Asn Gly Asn Thr
1 5

<210> SEQ ID NO 11
<211> LENGTH: 6
<212> TYPE: PRT
<213> ORGANISM: Artificial Sequence
<220> FEATURE:
<223> OTHER INFORMATION: 34-4 HCDR3

<400> SEQUENCE: 11

Thr Gly Gly Tyr Phe Tyr
1 5

<210> SEQ ID NO 12
<211> LENGTH: 11
<212> TYPE: PRT
<213> ORGANISM: Artificial Sequence
<220> FEATURE:
<223> OTHER INFORMATION: 34-4 LCDR1

<400> SEQUENCE: 12

Gln Ser Leu Val Gly Thr Gly Gly Lys Thr Tyr
1 5 10

<210> SEQ ID NO 13
<211> LENGTH: 3
<212> TYPE: PRT
<213> ORGANISM: Artificial Sequence
<220> FEATURE:
<223> OTHER INFORMATION: 34-4 LCDR2

<400> SEQUENCE: 13

Leu Val Ser
1

<210> SEQ ID NO 14
<211> LENGTH: 9
<212> TYPE: PRT
<213> ORGANISM: Artificial Sequence
<220> FEATURE:
<223> OTHER INFORMATION: 34-4 LCDR3

<400> SEQUENCE: 14

```
Leu Gln Gly Thr His Phe Pro Phe Thr
1               5


<210> SEQ ID NO 15
<211> LENGTH: 112
<212> TYPE: PRT
<213> ORGANISM: Artificial Sequence
<220> FEATURE:
<223> OTHER INFORMATION: 34-4 heavy chain variable region

<400> SEQUENCE: 15

Gln Val Gln Leu Met Glu Ser Gly Pro Gly Leu Val Gln Pro Ser Gln
1               5                   10                  15

Thr Leu Ser Leu Thr Cys Thr Val Ser Gly Phe Ser Leu Thr Ser Tyr
            20                  25                  30

Asp Met His Trp Val Arg Gln Pro Pro Gly Lys Gly Leu Glu Trp Met
        35                  40                  45

Gly Val Ile Trp Gly Asn Gly Asn Thr His Tyr Asn Ser Ala Leu Lys
    50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asn Thr Ala Ile Tyr Phe Cys Thr
                85                  90                  95

Gly Gly Tyr Phe Tyr Trp Gly Gln Gly Val Thr Val Thr Val Ser Ser
            100                 105                 110


<210> SEQ ID NO 16
<211> LENGTH: 112
<212> TYPE: PRT
<213> ORGANISM: Artificial Sequence
<220> FEATURE:
<223> OTHER INFORMATION: 34-4 light chain variable region

<400> SEQUENCE: 16

Asp Val Val Met Thr Gln Thr Pro Val Ser Leu Ser Val Ala Ile Gly
1               5                   10                  15

His Pro Ala Ser Ile Ser Cys Lys Ser Ser Gln Ser Leu Val Gly Thr
            20                  25                  30

Gly Gly Lys Thr Tyr Leu Ser Trp Leu Leu Gln Arg Pro Gly Gln Ser
        35                  40                  45

Pro Lys Arg Leu Ile Tyr Leu Val Ser Lys Leu Asp Ser Gly Ile Pro
    50                  55                  60

Asp Arg Phe Ser Gly Ser Gly Ser Glu Thr Asp Phe Thr Leu Lys Ile
65                  70                  75                  80

Ser Arg Val Glu Ala Asp Asp Leu Gly Val Tyr Tyr Cys Leu Gln Gly
                85                  90                  95

Thr His Phe Pro Phe Thr Phe Gly Ser Gly Thr Gln Leu Glu Met Lys
            100                 105                 110


<210> SEQ ID NO 17
<211> LENGTH: 8
<212> TYPE: PRT
<213> ORGANISM: Artificial Sequence
<220> FEATURE:
<223> OTHER INFORMATION: 27-8 HCDR1

<400> SEQUENCE: 17

Gly Tyr Thr Ile Thr Ser Gly Tyr
1               5
```

<210> SEQ ID NO 18
<211> LENGTH: 7
<212> TYPE: PRT
<213> ORGANISM: Artificial Sequence
<220> FEATURE:
<223> OTHER INFORMATION: 27-8 HCDR2

<400> SEQUENCE: 18

```
Ile Thr Tyr Ser Gly Ser Thr
1               5
```

<210> SEQ ID NO 19
<211> LENGTH: 11
<212> TYPE: PRT
<213> ORGANISM: Artificial Sequence
<220> FEATURE:
<223> OTHER INFORMATION: 27-8 HCDR3

<400> SEQUENCE: 19

```
Ser Arg Asp Ile Ala Ala Ile Ser Phe Ala Tyr
1               5                   10
```

<210> SEQ ID NO 20
<211> LENGTH: 11
<212> TYPE: PRT
<213> ORGANISM: Artificial Sequence
<220> FEATURE:
<223> OTHER INFORMATION: 27-8 LCDR1

<400> SEQUENCE: 20

```
Gln Ser Leu Val His Ser Asn Gly Asn Thr Tyr
1               5                   10
```

<210> SEQ ID NO 21
<211> LENGTH: 3
<212> TYPE: PRT
<213> ORGANISM: Artificial Sequence
<220> FEATURE:
<223> OTHER INFORMATION: 27-8 LCDR2

<400> SEQUENCE: 21

```
Lys Val Ser
1
```

<210> SEQ ID NO 22
<211> LENGTH: 9
<212> TYPE: PRT
<213> ORGANISM: Artificial Sequence
<220> FEATURE:
<223> OTHER INFORMATION: 27-8 LCDR3

<400> SEQUENCE: 22

```
Phe Gln Ala Thr His Val Pro Leu Thr
1               5
```

<210> SEQ ID NO 23
<211> LENGTH: 117
<212> TYPE: PRT
<213> ORGANISM: Artificial Sequence
<220> FEATURE:
<223> OTHER INFORMATION: 27-8 variable heavy chain

<400> SEQUENCE: 23

```
Val Gln Leu Thr Glu Ser Gly Pro Gly Leu Val Lys Pro Ser Gln Ser
1               5                   10                  15

Leu Ser Leu Thr Cys Ser Val Thr Gly Tyr Thr Ile Thr Ser Gly Tyr
            20                  25                  30
```

Asp Trp Ser Trp Ile Arg Lys Phe Pro Gly Asn Lys Met Glu Trp Met
35 40 45

Gly Tyr Ile Thr Tyr Ser Gly Ser Thr Asn Tyr Asn Pro Ser Leu Lys
50 55 60

Ser Arg Ile Ser Ile Thr Arg Asp Thr Ser Lys Asn Gln Phe Phe Leu
65 70 75 80

Gln Leu Asn Ser Val Thr Thr Glu Asp Thr Ala Thr Tyr Tyr Cys Ser
85 90 95

Arg Asp Ile Ala Ala Ile Ser Phe Ala Tyr Trp Gly Gln Gly Thr Leu
100 105 110

Val Thr Val Ser Ser
115

<210> SEQ ID NO 24
<211> LENGTH: 112
<212> TYPE: PRT
<213> ORGANISM: Artificial Sequence
<220> FEATURE:
<223> OTHER INFORMATION: 27-8 variable light chain

<400> SEQUENCE: 24

Asp Val Val Met Thr Gln Thr Pro Val Ala Gln Pro Val Thr Leu Gly
1 5 10 15

Asp Gln Ala Ser Ile Ser Cys Arg Ser Ser Gln Ser Leu Val His Ser
20 25 30

Asn Gly Asn Thr Tyr Leu Glu Trp Tyr Leu Gln Lys Pro Gly Gln Ser
35 40 45

Pro Gln Leu Leu Ile Tyr Lys Val Ser Asn Arg Phe Ser Gly Val Pro
50 55 60

Asp Arg Phe Ile Gly Ser Gly Ser Gly Ser Asp Phe Thr Leu Lys Ile
65 70 75 80

Ser Arg Val Glu Pro Glu Asp Leu Gly Val Tyr Tyr Cys Phe Gln Ala
85 90 95

Thr His Val Pro Leu Thr Phe Gly Ser Gly Thr Lys Leu Glu Ile Lys
100 105 110

<210> SEQ ID NO 25
<211> LENGTH: 8
<212> TYPE: PRT
<213> ORGANISM: Artificial Sequence
<220> FEATURE:
<223> OTHER INFORMATION: 46-3 HCDR1

<400> SEQUENCE: 25

Gly Tyr Thr Ile Thr Ser Gly Tyr
1 5

<210> SEQ ID NO 26
<211> LENGTH: 7
<212> TYPE: PRT
<213> ORGANISM: Artificial Sequence
<220> FEATURE:
<223> OTHER INFORMATION: 46-3 HCDR2

<400> SEQUENCE: 26

Ile Thr Tyr Ser Gly Ser Thr
1 5

<210> SEQ ID NO 27
<211> LENGTH: 11

<212> TYPE: PRT
<213> ORGANISM: Artificial Sequence
<220> FEATURE:
<223> OTHER INFORMATION: 46-3 HCDR3

<400> SEQUENCE: 27

Ala Arg Asp Phe Ser Gly Ile Ser Phe Ala Tyr
1               5                   10

<210> SEQ ID NO 28
<211> LENGTH: 11
<212> TYPE: PRT
<213> ORGANISM: Artificial Sequence
<220> FEATURE:
<223> OTHER INFORMATION: 46-3 LCDR1

<400> SEQUENCE: 28

Gln Ser Leu Val His Ser Asn Gly Asn Thr Tyr
1               5                   10

<210> SEQ ID NO 29
<211> LENGTH: 3
<212> TYPE: PRT
<213> ORGANISM: Artificial Sequence
<220> FEATURE:
<223> OTHER INFORMATION: 46-3 LCDR2

<400> SEQUENCE: 29

Lys Val Ser
1

<210> SEQ ID NO 30
<211> LENGTH: 9
<212> TYPE: PRT
<213> ORGANISM: Artificial Sequence
<220> FEATURE:
<223> OTHER INFORMATION: 46-3 LCDR3

<400> SEQUENCE: 30

Phe Gln Ala Thr His Asp Pro Leu Thr
1               5

<210> SEQ ID NO 31
<211> LENGTH: 117
<212> TYPE: PRT
<213> ORGANISM: Artificial Sequence
<220> FEATURE:
<223> OTHER INFORMATION: 46-3 heavy chain variable region

<400> SEQUENCE: 31

Val Gln Leu Lys Glu Ser Gly Pro Gly Leu Val Lys Pro Ser Gln Ser
1               5                   10                  15

Leu Ser Leu Thr Cys Ser Val Thr Gly Tyr Thr Ile Thr Ser Gly Tyr
            20                  25                  30

Asp Trp Ser Trp Ile Arg Lys Phe Pro Gly Asn Lys Met Glu Trp Met
        35                  40                  45

Gly Phe Ile Thr Tyr Ser Gly Ser Thr His His Asn Pro Ser Leu Lys
    50                  55                  60

Ser Arg Ile Ser Ile Thr Arg Asp Thr Ser Arg Asn Gln Phe Phe Leu
65                  70                  75                  80

Gln Leu Asn Ser Val Thr Thr Glu Asp Ser Ala Thr Tyr Tyr Cys Ala
                85                  90                  95

Arg Asp Phe Ser Gly Ile Ser Phe Ala Tyr Trp Gly Gln Gly Thr Leu
            100                 105                 110

Val Ser Val Ser Ser
        115

<210> SEQ ID NO 32
<211> LENGTH: 112
<212> TYPE: PRT
<213> ORGANISM: Artificial Sequence
<220> FEATURE:
<223> OTHER INFORMATION: 46-3 light chain variable region

<400> SEQUENCE: 32

Asp Val Val Leu Thr Gln Thr Pro Val Ala Gln Pro Val Thr Leu Gly
1               5                   10                  15

Asp Gln Val Ser Ile Ser Cys Arg Ser Ser Gln Ser Leu Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ile Gly Ser Gly Ser Gly Ser Asp Phe Thr Leu Lys Ile
65                  70                  75                  80

Ser Arg Val Glu Pro Glu Asp Leu Gly Ile Tyr Tyr Cys Phe Gln Ala
                85                  90                  95

Thr His Asp Pro Leu Thr Phe Gly Ser Gly Thr Lys Leu Glu Ile Lys
            100                 105                 110

<210> SEQ ID NO 33
<211> LENGTH: 8
<212> TYPE: PRT
<213> ORGANISM: Artificial Sequence
<220> FEATURE:
<223> OTHER INFORMATION: 21-3 HCDR1

<400> SEQUENCE: 33

Gly Phe Thr Phe Ser Asn Tyr Gly
1               5

<210> SEQ ID NO 34
<211> LENGTH: 8
<212> TYPE: PRT
<213> ORGANISM: Artificial Sequence
<220> FEATURE:
<223> OTHER INFORMATION: 21-3 HCDR2

<400> SEQUENCE: 34

Ile Asn Tyr Asp Gly Ser Ser Thr
1               5

<210> SEQ ID NO 35
<211> LENGTH: 12
<212> TYPE: PRT
<213> ORGANISM: Artificial Sequence
<220> FEATURE:
<223> OTHER INFORMATION: 21-3 HCDR3

<400> SEQUENCE: 35

Ala Arg Val Glu Tyr Arg Phe Ser Pro Phe Asp Tyr
1               5                   10

<210> SEQ ID NO 36
<211> LENGTH: 6
<212> TYPE: PRT
<213> ORGANISM: Artificial Sequence

<220> FEATURE:
<223> OTHER INFORMATION: 21-3 LCDR1

<400> SEQUENCE: 36

Gln Asn Ile Asn Lys Tyr
1 5

<210> SEQ ID NO 37
<211> LENGTH: 3
<212> TYPE: PRT
<213> ORGANISM: Artificial Sequence
<220> FEATURE:
<223> OTHER INFORMATION: 21-3 LCDR2

<400> SEQUENCE: 37

Asn Thr Asn
1

<210> SEQ ID NO 38
<211> LENGTH: 8
<212> TYPE: PRT
<213> ORGANISM: Artificial Sequence
<220> FEATURE:
<223> OTHER INFORMATION: 21-3 LCDR3

<400> SEQUENCE: 38

Leu Gln Arg Asn Ser Trp Leu Thr
1 5

<210> SEQ ID NO 39
<211> LENGTH: 118
<212> TYPE: PRT
<213> ORGANISM: Artificial Sequence
<220> FEATURE:
<223> OTHER INFORMATION: 21-3 heavy chain variable region

<400> SEQUENCE: 39

Val Gln Leu Met Glu Ser Gly Gly Gly Leu Val Gln Pro Gly Arg Ser
1 5 10 15

Leu Lys Leu Ser Cys Ala Ala Ser Gly Phe Thr Phe Ser Asn Tyr Gly
20 25 30

Met Ala Trp Val Arg Gln Ala Pro Thr Lys Gly Leu Glu Trp Val Ala
35 40 45

Thr Ile Asn Tyr Asp Gly Ser Ser Thr Tyr Tyr Arg Asp Ser Val Lys
50 55 60

Gly Arg Phe Thr Ile Ser Arg Asp Asn Ala Lys Ser Thr Leu Tyr Leu
65 70 75 80

Gln Met Asp Ser Leu Arg Ser Glu Asp Thr Ala Thr Tyr Tyr Cys Ala
85 90 95

Arg Val Glu Tyr Arg Phe Ser Pro Phe Asp Tyr Trp Gly Gln Gly Val
100 105 110

Thr Ala Thr Val Ser Ser
115

<210> SEQ ID NO 40
<211> LENGTH: 106
<212> TYPE: PRT
<213> ORGANISM: Artificial Sequence
<220> FEATURE:
<223> OTHER INFORMATION: 21-3 light chain variable region

<400> SEQUENCE: 40

Asp Val Gln Leu Thr Gln Ser Pro Ser Phe Leu Ser Ala Ser Val Gly

-continued

```
1               5                   10                  15

Glu Arg Val Thr Leu Ser Cys Lys Ala Ser Gln Asn Ile Asn Lys Tyr
            20                  25                  30

Leu Asp Trp Tyr Gln Gln Lys Leu Gly Glu Ala Pro Lys Leu Leu Ile
        35                  40                  45

Tyr Asn Thr Asn Asn Leu His Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Leu Gln Arg Asn Ser Trp Leu Thr
                85                  90                  95

Phe Gly Ser Gly Thr Lys Leu Glu Ile Lys
            100                 105


<210> SEQ ID NO 41
<211> LENGTH: 8
<212> TYPE: PRT
<213> ORGANISM: Artificial Sequence
<220> FEATURE:
<223> OTHER INFORMATION: 25-1 HCDR1

<400> SEQUENCE: 41

Gly Phe Asp Phe Lys Thr Tyr Ala
1               5


<210> SEQ ID NO 42
<211> LENGTH: 10
<212> TYPE: PRT
<213> ORGANISM: Artificial Sequence
<220> FEATURE:
<223> OTHER INFORMATION: 25-1 HCDR2

<400> SEQUENCE: 42

Ile Ser Ile Lys Thr Gln Asn Tyr Pro Thr
1               5                   10


<210> SEQ ID NO 43
<211> LENGTH: 6
<212> TYPE: PRT
<213> ORGANISM: Artificial Sequence
<220> FEATURE:
<223> OTHER INFORMATION: 25-1 HCDR3

<400> SEQUENCE: 43

Thr Val Gly Ala Arg Tyr
1               5


<210> SEQ ID NO 44
<211> LENGTH: 11
<212> TYPE: PRT
<213> ORGANISM: Artificial Sequence
<220> FEATURE:
<223> OTHER INFORMATION: 25-1 LCDR1

<400> SEQUENCE: 44

Gln Ser Leu Leu His Ser Asn Gly Asn Thr Tyr
1               5                   10


<210> SEQ ID NO 45
<211> LENGTH: 3
<212> TYPE: PRT
<213> ORGANISM: Artificial Sequence
<220> FEATURE:
<223> OTHER INFORMATION: 25-1 LCDR2
```

<400> SEQUENCE: 45

Leu Val Ser
1

<210> SEQ ID NO 46
<211> LENGTH: 9
<212> TYPE: PRT
<213> ORGANISM: Artificial Sequence
<220> FEATURE:
<223> OTHER INFORMATION: 25-1 LCDR3

<400> SEQUENCE: 46

Val Gln Ser Thr His Ala Pro Leu Thr
1 5

<210> SEQ ID NO 47
<211> LENGTH: 115
<212> TYPE: PRT
<213> ORGANISM: Artificial Sequence
<220> FEATURE:
<223> OTHER INFORMATION: 25-1 heavy chain variable region

<400> SEQUENCE: 47

Glu Val Gln Leu Val Glu Ser Gly Gly Gly Leu Val Gln Pro Lys Gly
1 5 10 15

Ser Leu Lys Leu Ser Cys Ala Ala Ser Gly Phe Asp Phe Lys Thr Tyr
20 25 30

Ala Met Ser Trp Val Arg Gln Ala Pro Gly Lys Gly Leu Asp Trp Val
35 40 45

Ala Ser Ile Ser Ile Lys Thr Gln Asn Tyr Pro Thr Leu Tyr Ala Asp
50 55 60

Ser Val Lys Glu Arg Phe Thr Ile Ser Arg Asp Asp Ser Gln Ser Met
65 70 75 80

Val Tyr Leu His Met Asn Asn Leu Lys Thr Glu Asp Thr Ala Leu Tyr
85 90 95

Tyr Cys Thr Val Gly Ala Arg Tyr Trp Gly Gln Gly Val Met Thr Thr
100 105 110

Val Ser Ser
115

<210> SEQ ID NO 48
<211> LENGTH: 112
<212> TYPE: PRT
<213> ORGANISM: Artificial Sequence
<220> FEATURE:
<223> OTHER INFORMATION: 25-1 light chain variable region

<400> SEQUENCE: 48

Asp Val Val Met Thr Gln Thr Pro Pro Thr Leu Ser Ala Thr Ile Gly
1 5 10 15

Gln Ser Val Ser Ile Ser Cys Arg Ser Ser Gln Ser Leu Leu His Ser
20 25 30

Asn Gly Asn Thr Tyr Leu Asn Trp Leu Leu Gln Arg Pro Gly Gln Pro
35 40 45

Pro Gln Val Leu Ile Tyr Leu Val Ser Arg Leu Glu Ser Gly Val Pro
50 55 60

Asn Arg Phe Ser Gly Ser Gly Ser Gly Thr Asp Phe Thr Leu Lys Ile
65 70 75 80

Ser Gly Val Glu Ala Glu Asp Leu Gly Val Tyr Tyr Cys Val Gln Ser

-continued

```
                85                  90                  95

Thr His Ala Pro Leu Thr Phe Gly Ser Gly Thr Lys Leu Glu Ile Lys
            100                 105                 110


<210> SEQ ID NO 49
<211> LENGTH: 8
<212> TYPE: PRT
<213> ORGANISM: Artificial Sequence
<220> FEATURE:
<223> OTHER INFORMATION: 41-10 HCDR1

<400> SEQUENCE: 49

Gly Phe Ser Leu Thr Ser Tyr Asp
1               5


<210> SEQ ID NO 50
<211> LENGTH: 7
<212> TYPE: PRT
<213> ORGANISM: Artificial Sequence
<220> FEATURE:
<223> OTHER INFORMATION: 41-10 HCDR2

<400> SEQUENCE: 50

Ile Trp Gly Asn Gly Asn Thr
1               5


<210> SEQ ID NO 51
<211> LENGTH: 7
<212> TYPE: PRT
<213> ORGANISM: Artificial Sequence
<220> FEATURE:
<223> OTHER INFORMATION: 41-10 HCDR3

<400> SEQUENCE: 51

Thr Arg Ser Leu Gly Val Gly
1               5


<210> SEQ ID NO 52
<211> LENGTH: 6
<212> TYPE: PRT
<213> ORGANISM: Artificial Sequence
<220> FEATURE:
<223> OTHER INFORMATION: 41-10 LCDR1

<400> SEQUENCE: 52

Gln Asp Ile Gly Asp Tyr
1               5


<210> SEQ ID NO 53
<211> LENGTH: 3
<212> TYPE: PRT
<213> ORGANISM: Artificial Sequence
<220> FEATURE:
<223> OTHER INFORMATION: 41-10 LCDR2

<400> SEQUENCE: 53

Gly Ala Thr
1


<210> SEQ ID NO 54
<211> LENGTH: 10
<212> TYPE: PRT
<213> ORGANISM: Artificial Sequence
<220> FEATURE:
<223> OTHER INFORMATION: 41-10 LCDR3

<400> SEQUENCE: 54
```

```
Leu Gln Ser Lys Glu Ser Pro Cys Ser Arg
1               5                   10


<210> SEQ ID NO 55
<211> LENGTH: 113
<212> TYPE: PRT
<213> ORGANISM: Artificial Sequence
<220> FEATURE:
<223> OTHER INFORMATION: 41-10 heavy chain variable region

<400> SEQUENCE: 55

Gln Val Gln Leu Thr Glu Ser Gly Pro Gly Leu Val Gln Pro Ser Gln
1               5                   10                  15

Thr Leu Ser Leu Thr Cys Thr Val Ser Gly Phe Ser Leu Thr Ser Tyr
            20                  25                  30

Asp Met His Trp Val Arg Gln Pro Pro Gly Lys Gly Leu Glu Trp Met
        35                  40                  45

Gly Val Ile Trp Gly Asn Gly Asn Thr His Tyr Asn Ser Ala Leu Lys
    50                  55                  60

Ser Arg Leu Ser Ile Ser Arg Asp Thr Ser Lys Arg Gln Val Phe Leu
65                  70                  75                  80

Lys Met Asn Ser Leu Gln Thr Glu Asp Thr Ala Ile Tyr Phe Cys Thr
                85                  90                  95

Arg Ser Leu Gly Val Gly Trp Gly Gln Gly Val Met Ile Ile Val Ser
            100                 105                 110

Ser


<210> SEQ ID NO 56
<211> LENGTH: 107
<212> TYPE: PRT
<213> ORGANISM: Artificial Sequence
<220> FEATURE:
<223> OTHER INFORMATION: 41-10 light chain variable region

<400> SEQUENCE: 56

Val Gln Met Thr Gln Ala Pro Ser Ser Leu Pro Ala Ser Leu Gly Asp
1               5                   10                  15

Arg Val Thr Ile Thr Cys Arg Ala Ser Gln Asp Ile Gly Asp Tyr Leu
            20                  25                  30

Arg Trp Phe Gln Gln Lys Pro Gly Lys Ser Pro Arg Leu Met Ile Tyr
        35                  40                  45

Gly Ala Thr Asn Leu Ala Ala Gly Val Pro Ser Arg Phe Ser Gly Ser
    50                  55                  60

Arg Ser Gly Ser Asp Tyr Ser Leu Thr Ile Ser Ser Leu Glu Ser Glu
65                  70                  75                  80

Asp Met Ala Asp Tyr Tyr Cys Leu Gln Ser Lys Glu Ser Pro Cys Ser
                85                  90                  95

Arg Ser Val Leu Gly Pro Asn Trp Arg Ser Asn
            100                 105


<210> SEQ ID NO 57
<211> LENGTH: 8
<212> TYPE: PRT
<213> ORGANISM: Artificial Sequence
<220> FEATURE:
<223> OTHER INFORMATION: 35-9 HCDR1

<400> SEQUENCE: 57

Gly Phe Ser Leu Ser Ser Tyr Gly
```

1 5

<210> SEQ ID NO 58
<211> LENGTH: 7
<212> TYPE: PRT
<213> ORGANISM: Artificial Sequence
<220> FEATURE:
<223> OTHER INFORMATION: 35-9 HCDR2

<400> SEQUENCE: 58

Ile Trp Gly Asn Gly Asn Thr
1 5

<210> SEQ ID NO 59
<211> LENGTH: 8
<212> TYPE: PRT
<213> ORGANISM: Artificial Sequence
<220> FEATURE:
<223> OTHER INFORMATION: 35-9 HCDR3

<400> SEQUENCE: 59

Ala Arg Trp Glu Ser Gly Asp Tyr
1 5

<210> SEQ ID NO 60
<211> LENGTH: 11
<212> TYPE: PRT
<213> ORGANISM: Artificial Sequence
<220> FEATURE:
<223> OTHER INFORMATION: 35-9 LCDR1

<400> SEQUENCE: 60

Gln Ser Leu Val Gly Ser Gly Gly Lys Thr Tyr
1 5 10

<210> SEQ ID NO 61
<211> LENGTH: 3
<212> TYPE: PRT
<213> ORGANISM: Artificial Sequence
<220> FEATURE:
<223> OTHER INFORMATION: 35-9 LCDR2

<400> SEQUENCE: 61

Leu Val Ser
1

<210> SEQ ID NO 62
<211> LENGTH: 9
<212> TYPE: PRT
<213> ORGANISM: Artificial Sequence
<220> FEATURE:
<223> OTHER INFORMATION: 35-9 LCDR3

<400> SEQUENCE: 62

Leu Gln Gly Thr His Phe Pro Trp Thr
1 5

<210> SEQ ID NO 63
<211> LENGTH: 114
<212> TYPE: PRT
<213> ORGANISM: Artificial Sequence
<220> FEATURE:
<223> OTHER INFORMATION: 35-9 variable heavy chain

<400> SEQUENCE: 63

Gln Val Gln Leu Thr Glu Ser Gly Pro Gly Leu Val Gln Pro Ser Gln
1 5 10 15

Thr Leu Ser Leu Thr Cys Thr Val Ser Gly Phe Ser Leu Ser Ser Tyr
20 25 30

Gly Val Ile Trp Val Arg Gln Pro Pro Gly Lys Gly Leu Glu Trp Met
35 40 45

Gly Val Ile Trp Gly Asn Gly Asn Thr Asn Tyr Asn Ser Thr Leu Lys
50 55 60

Ser Arg Leu Ser Ile Ser Arg Asp Thr Ser Lys Ser Gln Val Phe Leu
65 70 75 80

Lys Met Asn Ile Leu Gln Thr Glu Asp Thr Ala Met Tyr Phe Cys Ala
85 90 95

Arg Trp Glu Ser Gly Asp Tyr Trp Gly Gln Gly Val Thr Val Thr Val
100 105 110

Ser Ser

<210> SEQ ID NO 64
<211> LENGTH: 112
<212> TYPE: PRT
<213> ORGANISM: Artificial Sequence
<220> FEATURE:
<223> OTHER INFORMATION: 35-9 variable light chain

<400> SEQUENCE: 64

Asp Val Val Met Thr Gln Thr Pro Val Ser Leu Ser Val Ala Val Gly
1 5 10 15

Gln Pro Ala Ser Ile Ser Cys Thr Ser Ser Gln Ser Leu Val Gly Ser
20 25 30

Gly Gly Lys Thr Tyr Leu Asn Trp Phe Leu Gln Arg Pro Gly Gln Ser
35 40 45

Pro Lys Arg Leu Ile Ser Leu Val Ser Lys Leu Asp Ser Gly Ile Pro
50 55 60

Asp Arg Phe Ser Gly Ser Gly Ser Glu Thr Asp Phe Thr Leu Lys Ile
65 70 75 80

Ser Arg Val Glu Ala Asp Asp Leu Gly Val Tyr Tyr Cys Leu Gln Gly
85 90 95

Thr His Phe Pro Trp Thr Phe Gly Gly Gly Thr Lys Gln Glu Leu Lys
100 105 110

<210> SEQ ID NO 65
<211> LENGTH: 8
<212> TYPE: PRT
<213> ORGANISM: Artificial Sequence
<220> FEATURE:
<223> OTHER INFORMATION: 3-2 HCDR1

<400> SEQUENCE: 65

Gly Phe Thr Phe Ser Asp Tyr Gly
1 5

<210> SEQ ID NO 66
<211> LENGTH: 8
<212> TYPE: PRT
<213> ORGANISM: Artificial Sequence
<220> FEATURE:
<223> OTHER INFORMATION: 3-2 HCDR2

<400> SEQUENCE: 66

Ile Ser Ser Leu Ala Tyr Thr Val
1 5

<210> SEQ ID NO 67
<211> LENGTH: 10
<212> TYPE: PRT
<213> ORGANISM: Artificial Sequence
<220> FEATURE:
<223> OTHER INFORMATION: 3-2 HCDR3

<400> SEQUENCE: 67

```
Ala Arg Phe Pro Val Glu Ala Met Asp Tyr
1               5                   10
```

<210> SEQ ID NO 68
<211> LENGTH: 10
<212> TYPE: PRT
<213> ORGANISM: Artificial Sequence
<220> FEATURE:
<223> OTHER INFORMATION: 3-2 LCDR1

<400> SEQUENCE: 68

```
Glu Ser Val Asp Asn Tyr Gly Ile Ser Phe
1               5                   10
```

<210> SEQ ID NO 69
<211> LENGTH: 3
<212> TYPE: PRT
<213> ORGANISM: Artificial Sequence
<220> FEATURE:
<223> OTHER INFORMATION: 3-2 LCDR2

<400> SEQUENCE: 69

```
Ala Ala Ser
1
```

<210> SEQ ID NO 70
<211> LENGTH: 9
<212> TYPE: PRT
<213> ORGANISM: Artificial Sequence
<220> FEATURE:
<223> OTHER INFORMATION: 3-2 LCDR3

<400> SEQUENCE: 70

```
Gln Gln Ser Lys Glu Val Pro Pro Thr
1               5
```

<210> SEQ ID NO 71
<211> LENGTH: 116
<212> TYPE: PRT
<213> ORGANISM: Artificial Sequence
<220> FEATURE:
<223> OTHER INFORMATION: 3-2 heavy chain variable region

<400> SEQUENCE: 71

```
Val Gln Leu Gln Glu Ser Gly Gly Gly Leu Val Gln Pro Gly Gly Ser
1               5                   10                  15

Arg Lys Leu Ser Cys Ala Ala Ser Gly Phe Thr Phe Ser Asp Tyr Gly
            20                  25                  30

Met Ala Trp Val Arg Gln Ala Pro Gly Lys Gly Pro Glu Trp Val Ala
        35                  40                  45

Phe Ile Ser Ser Leu Ala Tyr Thr Val Tyr Tyr Ala Asp Thr Val Thr
    50                  55                  60

Gly Arg Phe Thr Ile Ser Arg Glu Asn Ala Lys Asn Thr Leu Phe Leu
65                  70                  75                  80

Glu Met Ser Ser Leu Arg Ser Glu Asp Thr Ala Met Tyr Tyr Cys Ala
                85                  90                  95
```

```
Arg Phe Pro Val Glu Ala Met Asp Tyr Trp Gly Gln Gly Thr Ser Val
            100                 105                 110

Thr Val Ser Ser
        115


<210> SEQ ID NO 72
<211> LENGTH: 97
<212> TYPE: PRT
<213> ORGANISM: Artificial Sequence
<220> FEATURE:
<223> OTHER INFORMATION: 3-2 light chain variable region

<400> SEQUENCE: 72

Ile Gly Gln Arg Ala Thr Ile Ser Cys Arg Ala Ser Glu Ser Val Asp
1               5                   10                  15

Asn Tyr Gly Ile Ser Phe Met Asn Trp Phe Gln Gln Lys Pro Gly Gln
            20                  25                  30

Pro Pro Lys Leu Leu Ile Tyr Ala Ala Ser Asn Gln Gly Ser Gly Val
        35                  40                  45

Pro Ala Arg Phe Ser Gly Ser Gly Ser Gly Thr Asp Phe Ser Leu Asn
    50                  55                  60

Ile His Pro Met Glu Glu Asp Asp Thr Ala Met Tyr Phe Cys Gln Gln
65                  70                  75                  80

Ser Lys Glu Val Pro Pro Thr Phe Gly Gly Gly Thr Lys Leu Glu Ile
                85                  90                  95

Lys


<210> SEQ ID NO 73
<211> LENGTH: 8
<212> TYPE: PRT
<213> ORGANISM: Artificial Sequence
<220> FEATURE:
<223> OTHER INFORMATION: 11-8 HCDR1

<400> SEQUENCE: 73

Gly Tyr Ser Phe Thr Asp Tyr Ile
1               5


<210> SEQ ID NO 74
<211> LENGTH: 8
<212> TYPE: PRT
<213> ORGANISM: Artificial Sequence
<220> FEATURE:
<223> OTHER INFORMATION: 11-8 HCDR2

<400> SEQUENCE: 74

Ile Asn Pro Tyr Ser Gly Asn Thr
1               5


<210> SEQ ID NO 75
<211> LENGTH: 11
<212> TYPE: PRT
<213> ORGANISM: Artificial Sequence
<220> FEATURE:
<223> OTHER INFORMATION: 11-8 HCDR3

<400> SEQUENCE: 75

Ala Arg Asp Gly Asp Asp Tyr Ala Met Asp Tyr
1               5                   10


<210> SEQ ID NO 76
<211> LENGTH: 10
<212> TYPE: PRT
```

-continued

<213> ORGANISM: Artificial Sequence
<220> FEATURE:
<223> OTHER INFORMATION: 11-8 LCDR1

<400> SEQUENCE: 76

Ser Ile Val His Ser Asn Gly Asn Thr Tyr
1               5                   10

<210> SEQ ID NO 77
<211> LENGTH: 3
<212> TYPE: PRT
<213> ORGANISM: Artificial Sequence
<220> FEATURE:
<223> OTHER INFORMATION: 11-8 LCDR2

<400> SEQUENCE: 77

Lys Val Ser
1

<210> SEQ ID NO 78
<211> LENGTH: 9
<212> TYPE: PRT
<213> ORGANISM: Artificial Sequence
<220> FEATURE:
<223> OTHER INFORMATION: 11-8 LCDR3

<400> SEQUENCE: 78

Phe Gln Gly Ser His Val Pro Trp Thr
1               5

<210> SEQ ID NO 79
<211> LENGTH: 117
<212> TYPE: PRT
<213> ORGANISM: Artificial Sequence
<220> FEATURE:
<223> OTHER INFORMATION: 11-8 heavy chain variable region

<400> SEQUENCE: 79

Val Gln Leu Gln Glu Ser Gly Pro Glu Leu Val Lys Pro Gly Ala Ser
1               5                   10                  15

Val Lys Ile Ser Cys Lys Ala Ser Gly Tyr Ser Phe Thr Asp Tyr Ile
            20                  25                  30

Ile Leu Trp Val Lys Gln Ser His Gly Lys Ser Leu Glu Trp Ile Gly
        35                  40                  45

Asn Ile Asn Pro Tyr Ser Gly Asn Thr Arg Tyr Asn Leu Lys Phe Lys
    50                  55                  60

Gly Lys Ala Thr Leu Thr Val Asp Lys Ser Ser Ser Thr Ala Tyr Met
65                  70                  75                  80

Gln Leu Asn Ser Leu Thr Ser Glu Asp Ser Ala Val Tyr Tyr Cys Ala
                85                  90                  95

Arg Asp Gly Asp Asp Tyr Ala Met Asp Tyr Trp Gly Gln Gly Thr Ser
            100                 105                 110

Val Thr Val Ser Ser
        115

<210> SEQ ID NO 80
<211> LENGTH: 112
<212> TYPE: PRT
<213> ORGANISM: Artificial Sequence
<220> FEATURE:
<223> OTHER INFORMATION: 11-8 light chain variable region

<400> SEQUENCE: 80

```
Asp Ile Val Ile Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Thr Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110


<210> SEQ ID NO 81
<211> LENGTH: 8
<212> TYPE: PRT
<213> ORGANISM: Artificial Sequence
<220> FEATURE:
<223> OTHER INFORMATION: 16-5 HCDR1

<400> SEQUENCE: 81

Gly Phe Thr Phe Ser Asp Tyr Gly
1               5


<210> SEQ ID NO 82
<211> LENGTH: 8
<212> TYPE: PRT
<213> ORGANISM: Artificial Sequence
<220> FEATURE:
<223> OTHER INFORMATION: 16-5 HCDR2

<400> SEQUENCE: 82

Ile Ser Ser Leu Ala Tyr Thr Val
1               5


<210> SEQ ID NO 83
<211> LENGTH: 10
<212> TYPE: PRT
<213> ORGANISM: Artificial Sequence
<220> FEATURE:
<223> OTHER INFORMATION: 16-5 HCDR3

<400> SEQUENCE: 83

Ala Arg Phe Pro Val Glu Ala Met Asp Tyr
1               5                   10


<210> SEQ ID NO 84
<211> LENGTH: 11
<212> TYPE: PRT
<213> ORGANISM: Artificial Sequence
<220> FEATURE:
<223> OTHER INFORMATION: 16-5 LCDR1

<400> SEQUENCE: 84

Gln Ser Leu Val His Ser Asn Gly Asn Thr Tyr
1               5                   10


<210> SEQ ID NO 85
<211> LENGTH: 3
<212> TYPE: PRT
<213> ORGANISM: Artificial Sequence
<220> FEATURE:
```

<223> OTHER INFORMATION: 16-5 LCDR2

<400> SEQUENCE: 85

Lys Val Ser
1

<210> SEQ ID NO 86
<211> LENGTH: 8
<212> TYPE: PRT
<213> ORGANISM: Artificial Sequence
<220> FEATURE:
<223> OTHER INFORMATION: 16-5 LCDR3

<400> SEQUENCE: 86

Ser Gln Ser Thr His Phe Leu Thr
1 5

<210> SEQ ID NO 87
<211> LENGTH: 116
<212> TYPE: PRT
<213> ORGANISM: Artificial Sequence
<220> FEATURE:
<223> OTHER INFORMATION: 16-5 heavy chain variable region

<400> SEQUENCE: 87

Val Lys Leu Gln Gln Ser Gly Gly Gly Leu Val Gln Pro Gly Gly Ser
1 5 10 15

Arg Lys Leu Ser Cys Ala Ala Ser Gly Phe Thr Phe Ser Asp Tyr Gly
20 25 30

Met Ala Trp Val Arg Gln Ala Pro Gly Lys Gly Pro Glu Trp Val Ala
35 40 45

Phe Ile Ser Ser Leu Ala Tyr Thr Val Tyr Tyr Ala Asp Thr Val Thr
50 55 60

Gly Arg Phe Thr Ile Ser Arg Glu Asn Ala Lys Asn Thr Leu Phe Leu
65 70 75 80

Glu Met Ser Ser Leu Arg Ser Glu Asp Thr Ala Met Tyr Tyr Cys Ala
85 90 95

Arg Phe Pro Val Glu Ala Met Asp Tyr Trp Gly Gln Gly Thr Ser Val
100 105 110

Thr Val Ser Ser
115

<210> SEQ ID NO 88
<211> LENGTH: 111
<212> TYPE: PRT
<213> ORGANISM: Artificial Sequence
<220> FEATURE:
<223> OTHER INFORMATION: 16-5 light chain variable region

<400> SEQUENCE: 88

Asp Ile Val Met Thr Gln Thr Pro Leu Ser Leu Pro Val Ser Leu Gly
1 5 10 15

Asp Gln Ala Ser Ile Ser Cys Arg Ser Ser Gln Ser Leu Val His Ser
20 25 30

Asn Gly Asn Thr Tyr Leu His Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

-continued

```
Ser Arg Val Glu Ala Glu Asp Leu Gly Val Tyr Phe Cys Ser Gln Ser
                85                  90                  95

Thr His Phe Leu Thr Phe Gly Ser Gly Thr Lys Leu Glu Ile Lys
            100                 105                 110


<210> SEQ ID NO 89
<211> LENGTH: 8
<212> TYPE: PRT
<213> ORGANISM: Artificial Sequence
<220> FEATURE:
<223> OTHER INFORMATION: 19-7 HCDR1

<400> SEQUENCE: 89

Gly Tyr Thr Phe Thr Ser Tyr Trp
1               5


<210> SEQ ID NO 90
<211> LENGTH: 8
<212> TYPE: PRT
<213> ORGANISM: Artificial Sequence
<220> FEATURE:
<223> OTHER INFORMATION: 19-7 HCDR2

<400> SEQUENCE: 90

Ile Tyr Pro Cys Asn Gly Arg Thr
1               5


<210> SEQ ID NO 91
<211> LENGTH: 9
<212> TYPE: PRT
<213> ORGANISM: Artificial Sequence
<220> FEATURE:
<223> OTHER INFORMATION: 19-7 HCDR3

<400> SEQUENCE: 91

Ala Arg Trp Asp Trp Val Phe Asp Tyr
1               5


<210> SEQ ID NO 92
<211> LENGTH: 10
<212> TYPE: PRT
<213> ORGANISM: Artificial Sequence
<220> FEATURE:
<223> OTHER INFORMATION: 19-7 LCDR1

<400> SEQUENCE: 92

Lys Ser Val Ser Thr Ser Gly Tyr Ser Tyr
1               5                   10


<210> SEQ ID NO 93
<211> LENGTH: 3
<212> TYPE: PRT
<213> ORGANISM: Artificial Sequence
<220> FEATURE:
<223> OTHER INFORMATION: 19-7 LCDR2

<400> SEQUENCE: 93

Leu Val Ser
1


<210> SEQ ID NO 94
<211> LENGTH: 8
<212> TYPE: PRT
<213> ORGANISM: Artificial Sequence
<220> FEATURE:
<223> OTHER INFORMATION: 19-7 LCDR3
```

<400> SEQUENCE: 94

Gln His Ile Arg Glu Leu Thr Arg
1               5

<210> SEQ ID NO 95
<211> LENGTH: 116
<212> TYPE: PRT
<213> ORGANISM: Artificial Sequence
<220> FEATURE:
<223> OTHER INFORMATION: 19-7 heavy chain variable region

<400> SEQUENCE: 95

Gln Val Lys Leu Gln Glu Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Asp Trp Ile
        35                  40                  45

Gly Glu Ile Tyr Pro Cys Asn Gly Arg Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Trp Asp Trp Val Phe Asp Tyr Trp Gly Gln Gly Thr Thr Leu
            100                 105                 110

Thr Val Ser Ser
        115

<210> SEQ ID NO 96
<211> LENGTH: 85
<212> TYPE: PRT
<213> ORGANISM: Artificial Sequence
<220> FEATURE:
<223> OTHER INFORMATION: 19-7 light chain variable region

<400> SEQUENCE: 96

Arg Ala Ser Lys Ser Val Ser Thr Ser Gly Tyr Ser Tyr Met His Trp
1               5                   10                  15

Asn Gln Gln Lys Pro Gly Gln Pro Pro Arg Leu Leu Ile Tyr Leu Val
            20                  25                  30

Ser Asn Pro Glu Ser Gly Val Pro Ala Arg Phe Ser Gly Ser Gly Ser
        35                  40                  45

Gly Thr Asp Phe Thr Leu Asn Ile His Pro Val Glu Glu Glu Asp Ala
    50                  55                  60

Ala Thr Tyr Tyr Cys Gln His Ile Arg Glu Leu Thr Arg Ser Glu Gly
65                  70                  75                  80

Gly Pro Ser Trp Lys
                85

<210> SEQ ID NO 97
<211> LENGTH: 8
<212> TYPE: PRT
<213> ORGANISM: Artificial Sequence
<220> FEATURE:
<223> OTHER INFORMATION: 22-3 HCDR1

<400> SEQUENCE: 97

Gly Phe Thr Phe Ser Asp Tyr Gly
1               5

<210> SEQ ID NO 98
<211> LENGTH: 8
<212> TYPE: PRT
<213> ORGANISM: Artificial Sequence
<220> FEATURE:
<223> OTHER INFORMATION: 22-3 HCDR2

<400> SEQUENCE: 98

Ile Ser Ser Leu Ala Tyr Thr Val
1               5

<210> SEQ ID NO 99
<211> LENGTH: 10
<212> TYPE: PRT
<213> ORGANISM: Artificial Sequence
<220> FEATURE:
<223> OTHER INFORMATION: 22-3 HCDR3

<400> SEQUENCE: 99

Ala Arg Phe Pro Val Glu Ala Met Asp Tyr
1               5                   10

<210> SEQ ID NO 100
<211> LENGTH: 10
<212> TYPE: PRT
<213> ORGANISM: Artificial Sequence
<220> FEATURE:
<223> OTHER INFORMATION: 22-3 LCDR1

<400> SEQUENCE: 100

Lys Ser Val Ser Thr Ser Gly Tyr Ser Tyr
1               5                   10

<210> SEQ ID NO 101
<211> LENGTH: 3
<212> TYPE: PRT
<213> ORGANISM: Artificial Sequence
<220> FEATURE:
<223> OTHER INFORMATION: 22-3 LCDR2

<400> SEQUENCE: 101

Leu Val Ser
1

<210> SEQ ID NO 102
<211> LENGTH: 8
<212> TYPE: PRT
<213> ORGANISM: Artificial Sequence
<220> FEATURE:
<223> OTHER INFORMATION: 22-3 LCDR3

<400> SEQUENCE: 102

Gln His Ile Arg Glu Leu Thr Arg
1               5

<210> SEQ ID NO 103
<211> LENGTH: 116
<212> TYPE: PRT
<213> ORGANISM: Artificial Sequence
<220> FEATURE:
<223> OTHER INFORMATION: 22-3 heavy chain variable region

<400> SEQUENCE: 103

Val Lys Leu Gln Glu Ser Gly Gly Gly Leu Val Gln Pro Gly Gly Ser
1               5                   10                  15

-continued

```
Arg Lys Leu Ser Cys Ala Ala Ser Gly Phe Thr Phe Ser Asp Tyr Gly
            20                  25                  30

Met Ala Trp Val Arg Gln Ala Pro Gly Lys Gly Pro Glu Trp Val Ala
        35                  40                  45

Phe Ile Ser Ser Leu Ala Tyr Thr Val Tyr Tyr Ala Asp Thr Val Thr
    50                  55                  60

Gly Arg Phe Thr Ile Ser Arg Glu Asn Ala Lys Asn Thr Leu Phe Leu
65                  70                  75                  80

Glu Met Ser Ser Leu Arg Ser Glu Asp Thr Ala Met Tyr Tyr Cys Ala
                85                  90                  95

Arg Phe Pro Val Glu Ala Met Asp Tyr Trp Gly Gln Gly Thr Ser Val
            100                 105                 110

Thr Val Ser Ser
        115
```

<210> SEQ ID NO 104
<211> LENGTH: 85
<212> TYPE: PRT
<213> ORGANISM: Artificial Sequence
<220> FEATURE:
<223> OTHER INFORMATION: 22-3 light chain variable region

<400> SEQUENCE: 104

```
Arg Ala Ser Lys Ser Val Ser Thr Ser Gly Tyr Ser Tyr Met His Trp
1               5                   10                  15

Asn Gln Gln Lys Pro Gly Gln Pro Pro Arg Leu Leu Ile Tyr Leu Val
            20                  25                  30

Ser Asn Leu Glu Ser Gly Val Pro Ala Arg Phe Ser Gly Ser Gly Ser
        35                  40                  45

Gly Thr Asp Phe Thr Leu Asn Ile His Pro Val Glu Glu Glu Asp Ala
    50                  55                  60

Ala Thr Tyr Tyr Cys Gln His Ile Arg Glu Leu Thr Arg Ser Glu Gly
65                  70                  75                  80

Gly Pro Ser Trp Lys
                85
```

<210> SEQ ID NO 105
<211> LENGTH: 8
<212> TYPE: PRT
<213> ORGANISM: Artificial Sequence
<220> FEATURE:
<223> OTHER INFORMATION: 23-1 HCDR1

<400> SEQUENCE: 105

```
Gly Tyr Ser Phe Thr Asp Tyr Ile
1               5
```

<210> SEQ ID NO 106
<211> LENGTH: 8
<212> TYPE: PRT
<213> ORGANISM: Artificial Sequence
<220> FEATURE:
<223> OTHER INFORMATION: 23-1 HCDR2

<400> SEQUENCE: 106

```
Ile Asn Pro Tyr Tyr Gly Ser Thr
1               5
```

<210> SEQ ID NO 107
<211> LENGTH: 11
<212> TYPE: PRT

<213> ORGANISM: Artificial Sequence
<220> FEATURE:
<223> OTHER INFORMATION: 23-1 HCDR3

<400> SEQUENCE: 107

Ala Arg Asp Gly Thr Asp Tyr Ala Met Asp Tyr
1 5 10

<210> SEQ ID NO 108
<211> LENGTH: 10
<212> TYPE: PRT
<213> ORGANISM: Artificial Sequence
<220> FEATURE:
<223> OTHER INFORMATION: 23-1 LCDR1

<400> SEQUENCE: 108

Lys Ser Val Ser Thr Ser Gly Tyr Ser Tyr
1 5 10

<210> SEQ ID NO 109
<211> LENGTH: 3
<212> TYPE: PRT
<213> ORGANISM: Artificial Sequence
<220> FEATURE:
<223> OTHER INFORMATION: 23-1 LCDR2

<400> SEQUENCE: 109

Leu Val Ser
1

<210> SEQ ID NO 110
<211> LENGTH: 8
<212> TYPE: PRT
<213> ORGANISM: Artificial Sequence
<220> FEATURE:
<223> OTHER INFORMATION: 23-1 LCDR3

<400> SEQUENCE: 110

Gln His Ile Arg Glu Leu Thr Arg
1 5

<210> SEQ ID NO 111
<211> LENGTH: 117
<212> TYPE: PRT
<213> ORGANISM: Artificial Sequence
<220> FEATURE:
<223> OTHER INFORMATION: 23-1 heavy chain variable region

<400> SEQUENCE: 111

Val Gln Leu Gln Glu Ser Gly Pro Glu Leu Val Lys Pro Gly Ala Ser
1 5 10 15

Val Lys Ile Ser Cys Lys Ala Ser Gly Tyr Ser Phe Thr Asp Tyr Ile
20 25 30

Met Leu Trp Leu Lys Gln Ser His Gly Lys Ser Leu Glu Trp Ile Gly
35 40 45

Asn Ile Asn Pro Tyr Tyr Gly Ser Thr Arg Tyr Asn Leu Lys Phe Lys
50 55 60

Gly Lys Ala Thr Leu Thr Val Asp Lys Ser Ser Ser Thr Ala Tyr Met
65 70 75 80

Gln Leu Asn Ser Leu Thr Ser Glu Asp Ser Ala Val Tyr Tyr Cys Ala
85 90 95

Arg Asp Gly Thr Asp Tyr Ala Met Asp Tyr Trp Gly Gln Gly Thr Ser
100 105 110

```
Val Thr Val Ser Ser
        115


<210> SEQ ID NO 112
<211> LENGTH: 85
<212> TYPE: PRT
<213> ORGANISM: Artificial Sequence
<220> FEATURE:
<223> OTHER INFORMATION: 23-1 light chain variable region

<400> SEQUENCE: 112

Arg Ala Ser Lys Ser Val Ser Thr Ser Gly Tyr Ser Tyr Met His Trp
1               5                   10                  15

Asn Gln Gln Lys Pro Gly Gln Pro Pro Arg Leu Leu Ile Tyr Leu Val
            20                  25                  30

Ser Asn Leu Glu Ser Gly Val Pro Ala Arg Phe Ser Gly Ser Gly Ser
        35                  40                  45

Gly Thr Asp Phe Thr Leu Asn Ile His Pro Val Glu Glu Glu Asp Ala
    50                  55                  60

Ala Thr Tyr Tyr Cys Gln His Ile Arg Glu Leu Thr Arg Ser Glu Gly
65                  70                  75                  80

Gly Pro Ser Trp Lys
                85


<210> SEQ ID NO 113
<211> LENGTH: 8
<212> TYPE: PRT
<213> ORGANISM: Artificial Sequence
<220> FEATURE:
<223> OTHER INFORMATION: 8-2 HCDR1

<400> SEQUENCE: 113

Gly Tyr Thr Ile Thr Asp Tyr Tyr
1               5


<210> SEQ ID NO 114
<211> LENGTH: 8
<212> TYPE: PRT
<213> ORGANISM: Artificial Sequence
<220> FEATURE:
<223> OTHER INFORMATION: 8-2 HCDR2

<400> SEQUENCE: 114

Ile Asn Pro Tyr Asn Gly Gly Thr
1               5


<210> SEQ ID NO 115
<211> LENGTH: 12
<212> TYPE: PRT
<213> ORGANISM: Artificial Sequence
<220> FEATURE:
<223> OTHER INFORMATION: 8-2 HCDR3

<400> SEQUENCE: 115

Ala Arg Ser Arg Thr Gly Gly Asn Gly Met Asp Tyr
1               5                   10


<210> SEQ ID NO 116
<211> LENGTH: 10
<212> TYPE: PRT
<213> ORGANISM: Artificial Sequence
<220> FEATURE:
<223> OTHER INFORMATION: 8-2 LCDR1

<400> SEQUENCE: 116
```

```
Lys Ser Val Ser Thr Ser Gly Tyr Ser Tyr
1               5                   10


<210> SEQ ID NO 117
<211> LENGTH: 3
<212> TYPE: PRT
<213> ORGANISM: Artificial Sequence
<220> FEATURE:
<223> OTHER INFORMATION: 8-2 LCDR2

<400> SEQUENCE: 117

Leu Val Ser
1


<210> SEQ ID NO 118
<211> LENGTH: 8
<212> TYPE: PRT
<213> ORGANISM: Artificial Sequence
<220> FEATURE:
<223> OTHER INFORMATION: 8-2 LCDR3

<400> SEQUENCE: 118

Gln His Ile Arg Glu Leu Thr Arg
1               5


<210> SEQ ID NO 119
<211> LENGTH: 118
<212> TYPE: PRT
<213> ORGANISM: Artificial Sequence
<220> FEATURE:
<223> OTHER INFORMATION: 8-2 Heavy chain variable region

<400> SEQUENCE: 119

Val Gln Leu Gln Glu Ser Gly Pro Val Leu Val Lys Pro Gly Ala Ser
1               5                   10                  15

Val Lys Met Ser Cys Lys Ala Ser Gly Tyr Thr Ile Thr Asp Tyr Tyr
            20                  25                  30

Met Asn Trp Val Lys Gln Ser His Gly Lys Ser Leu Glu Trp Ile Gly
        35                  40                  45

Val Ile Asn Pro Tyr Asn Gly Gly Thr Ser Tyr Asn Gln Lys Phe Lys
    50                  55                  60

Gly Lys Ala Thr Leu Thr Val Asp Lys Ser Ser Ser Thr Ala Tyr Met
65                  70                  75                  80

Glu Leu Asn Ser Leu Thr Ser Glu Asp Ser Ala Val Tyr Tyr Cys Ala
                85                  90                  95

Arg Ser Arg Thr Gly Gly Asn Gly Met Asp Tyr Trp Gly Gln Gly Thr
            100                 105                 110

Ser Val Thr Val Ser Ser
        115


<210> SEQ ID NO 120
<211> LENGTH: 108
<212> TYPE: PRT
<213> ORGANISM: Artificial Sequence
<220> FEATURE:
<223> OTHER INFORMATION: 8-2 Light chain variable region

<400> SEQUENCE: 120

Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30
```

Gly Tyr Ser Tyr Met His Trp Asn Gln Gln Lys Pro Gly Gln Pro Pro
35 40 45

Arg Leu Leu Ile Tyr Leu Val Ser Asn Leu Glu Ser Gly Val Pro Ala
50 55 60

Arg Phe Ser Gly Ser Gly Ser Gly Thr Asp Phe Thr Leu Asn Ile His
65 70 75 80

Pro Val Glu Glu Glu Asp Ala Ala Thr Tyr Tyr Cys Gln His Ile Arg
85 90 95

Glu Leu Thr Arg Ser Glu Gly Gly Pro Ser Trp Lys
100 105

<210> SEQ ID NO 121
<211> LENGTH: 8
<212> TYPE: PRT
<213> ORGANISM: Artificial Sequence
<220> FEATURE:
<223> OTHER INFORMATION: 13-1 HCDR1

<400> SEQUENCE: 121

Gly Tyr Ser Phe Thr Gly Tyr Phe
1 5

<210> SEQ ID NO 122
<211> LENGTH: 8
<212> TYPE: PRT
<213> ORGANISM: Artificial Sequence
<220> FEATURE:
<223> OTHER INFORMATION: 13-1 HCDR2

<400> SEQUENCE: 122

Ile Asn Pro Tyr Asn Gly Asp Thr
1 5

<210> SEQ ID NO 123
<211> LENGTH: 13
<212> TYPE: PRT
<213> ORGANISM: Artificial Sequence
<220> FEATURE:
<223> OTHER INFORMATION: 13-1 HCDR3

<400> SEQUENCE: 123

Ala Lys Trp Asp Leu Tyr Asp Gly Tyr Phe Arg Asp Tyr
1 5 10

<210> SEQ ID NO 124
<211> LENGTH: 10
<212> TYPE: PRT
<213> ORGANISM: Artificial Sequence
<220> FEATURE:
<223> OTHER INFORMATION: 13-1 LCDR1

<400> SEQUENCE: 124

Lys Ser Val Ser Thr Ser Gly Tyr Ser Tyr
1 5 10

<210> SEQ ID NO 125
<211> LENGTH: 3
<212> TYPE: PRT
<213> ORGANISM: Artificial Sequence
<220> FEATURE:
<223> OTHER INFORMATION: 13-1 LCDR2

<400> SEQUENCE: 125

Leu Val Ser

1

<210> SEQ ID NO 126
<211> LENGTH: 8
<212> TYPE: PRT
<213> ORGANISM: Artificial Sequence
<220> FEATURE:
<223> OTHER INFORMATION: 13-1 LCDR3

<400> SEQUENCE: 126

```
Gln His Ile Arg Glu Leu Thr Arg
1               5
```

<210> SEQ ID NO 127
<211> LENGTH: 119
<212> TYPE: PRT
<213> ORGANISM: Artificial Sequence
<220> FEATURE:
<223> OTHER INFORMATION: 13-1 Heavy chain variable region

<400> SEQUENCE: 127

```
Val Lys Leu Gln Glu Ser Gly Pro Glu Leu Val Lys Pro Gly Ala Ser
1               5                   10                  15

Val Lys Ile Ser Cys Lys Ala Ser Gly Tyr Ser Phe Thr Gly Tyr Phe
            20                  25                  30

Met Asn Trp Val Met Gln Ser His Gly Lys Ser Leu Glu Trp Ile Gly
        35                  40                  45

Arg Ile Asn Pro Tyr Asn Gly Asp Thr Phe Tyr Asn Gln Lys Phe Lys
    50                  55                  60

Gly Lys Ala Thr Leu Thr Val Asp Lys Ser Ser Ser Thr Ala His Met
65                  70                  75                  80

Glu Leu Arg Ser Leu Ala Ser Glu Asp Ser Ala Val Tyr Tyr Cys Ala
                85                  90                  95

Lys Trp Asp Leu Tyr Asp Gly Tyr Phe Arg Asp Tyr Trp Gly Gln Gly
            100                 105                 110

Thr Thr Leu Thr Val Ser Ser
        115
```

<210> SEQ ID NO 128
<211> LENGTH: 108
<212> TYPE: PRT
<213> ORGANISM: Artificial Sequence
<220> FEATURE:
<223> OTHER INFORMATION: 13-1 Light chain variable region

<400> SEQUENCE: 128

```
Asp Ile Val Met Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys
            100                 105
```

<210> SEQ ID NO 129
<211> LENGTH: 8
<212> TYPE: PRT
<213> ORGANISM: Artificial Sequence
<220> FEATURE:
<223> OTHER INFORMATION: 32-1 HCDR1

<400> SEQUENCE: 129

Gly Phe Thr Phe Ser Ser Tyr Gly
1               5

<210> SEQ ID NO 130
<211> LENGTH: 8
<212> TYPE: PRT
<213> ORGANISM: Artificial Sequence
<220> FEATURE:
<223> OTHER INFORMATION: 32-1 HCDR2

<400> SEQUENCE: 130

Ile Ser Ser Gly Gly Ser Tyr Thr
1               5

<210> SEQ ID NO 131
<211> LENGTH: 9
<212> TYPE: PRT
<213> ORGANISM: Artificial Sequence
<220> FEATURE:
<223> OTHER INFORMATION: 32-1 HCDR3

<400> SEQUENCE: 131

Val Ile Asp Tyr Asp Val Met Asp Tyr
1               5

<210> SEQ ID NO 132
<211> LENGTH: 12
<212> TYPE: PRT
<213> ORGANISM: Artificial Sequence
<220> FEATURE:
<223> OTHER INFORMATION: 32-1 LCDR1

<400> SEQUENCE: 132

Gln Ser Leu Leu Asn Ser Arg Thr Arg Lys Asn Tyr
1               5                   10

<210> SEQ ID NO 133
<211> LENGTH: 3
<212> TYPE: PRT
<213> ORGANISM: Artificial Sequence
<220> FEATURE:
<223> OTHER INFORMATION: 32-1 LCDR2

<400> SEQUENCE: 133

Trp Ala Ser
1

<210> SEQ ID NO 134
<211> LENGTH: 8
<212> TYPE: PRT
<213> ORGANISM: Artificial Sequence
<220> FEATURE:
<223> OTHER INFORMATION: 32-1 LCDR3

<400> SEQUENCE: 134

Lys Gln Ser Tyr Asn Leu Arg Thr
1               5

-continued

```
<210> SEQ ID NO 135
<211> LENGTH: 115
<212> TYPE: PRT
<213> ORGANISM: Artificial Sequence
<220> FEATURE:
<223> OTHER INFORMATION: 32-1 Heavy chain variable region

<400> SEQUENCE: 135

Val Gln Leu Gln Gln Ser Gly Gly Asp Leu Val Lys Pro Gly Gly Ser
1               5                   10                  15

Leu Lys Leu Ser Cys Ala Ala Ser Gly Phe Thr Phe Ser Ser Tyr Gly
            20                  25                  30

Met Ser Trp Val Arg Gln Thr Pro Asp Lys Arg Leu Glu Trp Val Ala
        35                  40                  45

Thr Ile Ser Ser Gly Gly Ser Tyr Thr Tyr Tyr Pro Asp Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Lys Ser Glu Asp Thr Ala Met Tyr Tyr Cys Val
                85                  90                  95

Ile Asp Tyr Asp Val Met Asp Tyr Trp Gly Gln Gly Thr Ser Val Thr
            100                 105                 110

Val Ser Ser
        115


<210> SEQ ID NO 136
<211> LENGTH: 112
<212> TYPE: PRT
<213> ORGANISM: Artificial Sequence
<220> FEATURE:
<223> OTHER INFORMATION: 32-1 Light chain variable region

<400> SEQUENCE: 136

Asp Ile Val Met Thr Gln Thr Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Arg Thr Phe Gly Gly Gly Thr Lys Leu Glu Ile Lys
            100                 105                 110
```